United States Patent
Zhong et al.

(10) Patent No.: US 11,692,020 B2
(45) Date of Patent: Jul. 4, 2023

(54) CYTOKINE FUSION PROTEINS, AND THEIR PHARMACEUTICAL COMPOSITIONS AND THERAPEUTIC APPLICATIONS

(71) Applicant: Anwita Biosciences, Inc., San Carlos, CA (US)

(72) Inventors: Ziyang Zhong, Belmont, CA (US); Fan Ye, Mountain View, CA (US); Matthew Siegel, Menlo Park, CA (US); Jianing Huang, San Mateo, CA (US)

(73) Assignee: Anwita Biosciences, Inc., San Carlos, CA (US)

( * ) Notice: Subject to any disclaimer, the term of this patent is extended or adjusted under 35 U.S.C. 154(b) by 222 days.

(21) Appl. No.: 16/952,079

(22) Filed: Nov. 19, 2020

(65) Prior Publication Data

US 2021/0163565 A1 Jun. 3, 2021

Related U.S. Application Data

(60) Provisional application No. 62/938,275, filed on Nov. 20, 2019.

(51) Int. Cl.
C07K 14/55 (2006.01)
C07K 16/00 (2006.01)
A61K 38/00 (2006.01)

(52) U.S. Cl.
CPC ............ *C07K 14/55* (2013.01); *C07K 16/00* (2013.01); *A61K 38/00* (2013.01); *C07K 2317/565* (2013.01); *C07K 2317/569* (2013.01); *C07K 2319/31* (2013.01); *C07K 2319/33* (2013.01)

(58) Field of Classification Search
CPC .................................................. C07K 14/55
See application file for complete search history.

(56) References Cited

U.S. PATENT DOCUMENTS

| | | |
|---|---|---|
| 7,569,215 B2 | 8/2009 | Wittrup et al. |
| 7,951,360 B2 | 5/2011 | Wittrup et al. |
| 8,349,311 B2 | 1/2013 | Wittrup et al. |
| 8,945,897 B2 | 2/2015 | Siekmann et al. |
| 9,732,134 B2 | 8/2017 | Gavin et al. |
| 9,957,323 B2 | 5/2018 | Sainson et al. |
| 10,035,836 B1 | 7/2018 | Greve |
| 10,143,726 B2 | 12/2018 | Oft |
| 10,604,576 B2 | 3/2020 | Campbell et al. |
| 10,851,144 B2 | 12/2020 | Butz et al. |
| 2010/0150939 A1 | 6/2010 | Blanchetot et al. |
| 2015/0093336 A1 | 4/2015 | Ginderachter et al. |
| 2015/0158929 A1 | 6/2015 | Schellenberger et al. |
| 2016/0207991 A1 | 7/2016 | Bloom et al. |
| 2017/0107302 A1 | 4/2017 | Silence et al. |
| 2017/0362339 A1 | 12/2017 | Liu et al. |
| 2018/0326010 A1 | 11/2018 | Deak et al. |
| 2018/0326060 A1 | 11/2018 | Wesche et al. |
| 2019/0016793 A1 | 1/2019 | Cini et al. |
| 2019/0031749 A1 | 1/2019 | Dubridge et al. |
| 2019/0046611 A1 | 2/2019 | Ali et al. |
| 2019/0202917 A1 | 7/2019 | Campbell et al. |
| 2019/0338032 A1 | 11/2019 | Campbell et al. |
| 2019/0352363 A1 | 11/2019 | Seidel, III et al. |
| 2020/0199181 A1 | 6/2020 | Seidel, III et al. |
| 2020/0207824 A1 | 7/2020 | Seidel, III et al. |

FOREIGN PATENT DOCUMENTS

| | | |
|---|---|---|
| CA | 3098765 A1 | 3/2020 |
| CA | 3098930 A1 | 3/2020 |
| CN | 110325205 A | 10/2019 |
| CN | 111647068 A | 9/2020 |
| WO | 2005005638 A2 | 1/2005 |
| WO | 2005007121 A2 | 1/2005 |
| WO | 2010085495 A1 | 7/2010 |
| WO | 2016164937 A2 | 10/2016 |
| WO | 2016196211 A1 | 12/2016 |
| WO | 2017158436 A1 | 9/2017 |
| WO | 2018071918 A1 | 4/2018 |
| WO | 2018104444 A1 | 6/2018 |
| WO | 2018119114 A1 | 6/2018 |
| WO | 2018151868 A2 | 8/2018 |
| WO | 2018170168 A1 | 9/2018 |
| WO | 2018184964 A1 | 10/2018 |
| WO | 2019051091 A1 | 3/2019 |
| WO | 2019051094 A1 | 3/2019 |
| WO | 2019125732 A1 | 6/2019 |
| WO | 2019139896 A1 | 7/2019 |
| WO | 2019246003 A1 | 12/2019 |
| WO | 2019246004 A1 | 12/2019 |
| WO | 2020057645 A1 | 3/2020 |
| WO | 2020057646 A1 | 3/2020 |
| WO | 2020125743 A1 | 6/2020 |
| WO | 2020172528 A1 | 8/2020 |

OTHER PUBLICATIONS

Abbas et al., "Revisiting IL-2: Biology and therapeutic prospects," Sci. Immunol. 2018, 3, eaat1482.
Adams et al., "Extending the half-life of a fab fragment through generation of a humanized anti-human serum albumin Fv domain: An investigation into the correlation between affinity and serum half-life," MAbs 2016, 8, 1336-46.
Atkins et al., "High-dose recombinant interleukin 2 therapy for patients with metastatic melanoma: analysis of 270 patients treated between 1985 and 1993," J. Clin. Oncol. 1999, 17, 2105-2116.
Bluestone, "The yin and yang of interleukin-2-mediated immunotherapy," N. Engl. J. Med. 2011, 365, 2129-31.

(Continued)

*Primary Examiner* — Prema M Mertz
(74) *Attorney, Agent, or Firm* — Lin Yu; Juniv LLP

(57) ABSTRACT

Provided herein are a fusion protein comprising first and second cytokine domains, and a half-life extension domain; and a pharmaceutical composition thereof. Also provided herein are methods of their use for treating, preventing, or ameliorating one or more symptoms of a proliferative disease.

34 Claims, 4 Drawing Sheets
Specification includes a Sequence Listing.

(56) References Cited

OTHER PUBLICATIONS

Boyman et al., "The role of interleukin-2 during homeostasis and activation of the immune system," Nat. Rev. Immunol. 2012, 12, 180-90.

Conlon et al., "Cytokines in the treatment of cancer," J. Interferon Cytokine Res. 2019, 39, 6-21.

Conlon et al., "Redistribution, hyperproliferation, activation of natural killer cells and CD8 T cells, and cytokine production during first-in-human clinical trial of recombinant human interleukin-15 in patients with cancer," J. Clin. Oncol. 2015, 33, 74-82.

Croce et al., "IL-21: a pleiotropic cytokine with potential applications in oncology," J. Immunol. Res. 2015, 696578.

Davis et al., "An open-label, two-arm, phase I trial of recombinant human interleukin-21 in patients with metastatic melanoma," Clin. Cancer Res. 2007, 13, 3630-36.

Dennis et al., "Albumin binding as a general strategy for improving the pharmacokinetics of proteins," J. Biol. Chem. 2002, 277, 35035-43.

Heaton et al., "Human interleukin 2 analogues that preferentially bind the intermediate-affinity interleukin 2 receptor lead to reduced secondary cytokine secretion: implications for the use of these interleukin 2 analogues in cancer immunotherapy," Cancer Res. 1993, 53, 2597-602.

Hu et al., "Generation of low-toxicity interleukin-2 fusion proteins devoid of vasopermeability activity," Blood 2002, 101, 4853-61.

Huang et al., "A novel strategy to produce high level and high purity of bioactive IL15 fusion proteins from mammalian cells," Protein Expr. Purifi. 2018, 148, 30-9.

Klapper et al., "High-dose interleukin-2 for the treatment of metastatic renal cell carcinoma : a retrospective analysis of response and survival in patients treated in the surgery branch at the National Cancer Institute between 1986 and 2006," Cancer 2008, 113, 293-301.

Leonard and Wan, "IL-21 signaling in immunity," F1000Res. 2016, 5(F1000 Faculty Rev), 224.

Liao et al., "IL-2 family cytokines: new insights into the complex roles of IL-2 as a broad regulator of T helper cell differentiation," Curr. Opin. Immunol. 2011, 23, 598-604.

Malek et al., "Interleukin-2 receptor signaling: at the interface between tolerance and immunity," Immunity 2010, 33, 153-165.

Proleukin® Label (2012).

Rham et al., "The proinflammatory cytokines IL-2, IL-15 and IL-21 modulate the repertoire of mature human natural killer cell receptors," Arthritis Res. Ther. 2007, 9, R125.

Richert et al., "Compensatory energetic mechanisms mediating the assembly of signaling complexes between Interleukin-2 and its alpha, beta, and gamma(c) receptors," J Mol. Biol. 2004, 339, 1115-9.

Ridgway et al., "'Knobs-into-holes' engineering of antibody CH3 domains for heavy chain heterodimerization," Protein Eng. 1996, 9, 617-21.

Robb et al., "Low and high affinity cellular receptors for interleukin 2. Implications for the level of Tac antigen," J. Exp. Med. 1984, 160, 1126-46.

Robinson and Schluns, "The potential and promise of IL-15 in immuno-oncogenic therapies," Immunol. Lett. 2017, 159-68.

Rosenberg, "IL-2: the first effective immunotherapy for human cancer," J. Immunol. 2014, 192, 5451-8.

Rosenberg, "Raising the bar: the curative potential of human cancer immunotherapy," Sci. Transl. Med. 2012, 4, 127ps8.

Schmidt et al., "Safety and clinical effect of subcutaneous human interieukin-21 in patients with metastatic melanoma or renal cell carcinoma: a phase I trial," Clin. Cancer Res. 2010, 16, 5312-9.

Skrombolas et al., "Challenges and developing solutions for increasing the benefits of IL-2 treatment in tumor therapy," Expert Rev. Clin. Immunol. 2014, 10, 207-17.

Sola and Griebenow, "Effects of glycosylation on the stability of protein pharmaceuticals," J. Pharm. Sci. 2009, 98, 1223-45.

Sola et al., "Modulation of protein biophysical properties by chemical glycosylation: biochemical insights and biomedical implications," Cell. Mol. Life Sci. 2007, 64, 2133-52.

Spangler et al., "Insights into cytokine-receptor interactions from cytokine engineering," Annu. Rev. Immunol. 2015, 33, 139-67.

Stauber et al., "Crystal structure of the IL-2 signaling complex: paradigm for a heterotrimeric cytokine receptor," Proc. Natl. Acad. Sci. U.S.A. 2006, 103, 2788-93.

Steel et al., "Interleukin-15 biology and its therapeutic implications in cancer," Trends Pharmacol. Sci 2012, 33, 35-41.

Szabo et al., "High Performance Anion Exchange and Hydrophilic Interaction Liquid Chromatography Approaches for Comprehensive Mass Spectrometry-Based Characterization of the N-Glycome of a Recombinant Human Erythropoietin," J. Proteome. Res. 2018, 17, 1559-1574.

Tang and Harding, "The challenges and molecular approaches surrounding interleukin-2-based therapeutics in cancer," Cytokine: X 2019, 1, 100001.

Waldmann et al., "The biology of interleukin-2 and interleukin-15: implications for cancer therapy and vaccine design," Nat. Rev. Immunol. 2006, 6, 595-601.

Waldmann, "The shared and contrasting roles of IL2 and IL15 in the life and death of normal and neoplastic lymphocytes: implications for cancer therapy," Cancer Immunol. Res. 2015, 3, 219-27.

Wang et al., "Structure of the quaternary complex of interleukin-2 with its α, β, and γc receptors," Science 2005, 310, 1159-1163.

CYTOKINE FUSION PROTEINS, AND THEIR PHARMACEUTICAL COMPOSITIONS AND THERAPEUTIC APPLICATIONS

CROSS REFERENCE TO RELATED APPLICATION

This application claims the benefit of U.S. Provisional Application No. 62/938,275, filed Nov. 20, 2019; the disclosure of which is incorporated herein by reference in its entirety.

FIELD

Provided herein are a fusion protein comprising first and second cytokine domains, and a half-life extension domain; and a pharmaceutical composition thereof. Also provided herein are methods of their use for treating, preventing, or ameliorating one or more symptoms of a proliferative disease.

REFERENCE TO A SEQUENCE LISTING

The present specification is being filed with a Sequence Listing in Computer Readable Form (CRF), which is entitled 216A005US01_SEQ_LISTING_ST25.txt of 203,407 bytes in size and created Nov. 18, 2020; the content of which is incorporated herein by reference in its entirety.

BACKGROUND

Cytokines regulate the innate and adaptive immune system, and control proliferation, differentiation, effector functions, and survival of leukocytes. Conlon et al., *J. Interferon Cytokine Res.* 2019, 39, 6-21. Because of the ability of the immune system to recognize and destroy cancer cells, cytokines have been explored as therapeutic agents for cancer treatment. Id.

An interleukin-2 (IL-2) is a pleiotropic cytokine that orchestrates the proliferation, survival, and function of both immune effector (Teff) cells and regulatory T (Treg) cells to maintain immune homeostasis. Bluestone, *N. Engl. J. Med.* 2011, 365, 2129-31; Boyman et al., *Nat. Rev. Immunol.* 2012, 12, 180-90. The IL-2 drives T-cell growth, augments natural killer (NK) cytolytic activity, induces the differentiation of regulatory T (Treg) cells, and mediates activation-induced cell death. Liao et al., *Curr. Opin. Immunol.* 2011, 23, 598-604.

An interleukin-2 receptor (IL-2R) exists in three different forms generated from three different interleukin-2 receptor chains: α chain (IL-2Rα or CD25), β chain (IL-2Rβ or CD122), and γ chain (IL-2Rγ, $γ_c$, or CD132). Wang et al., *Science* 2005, 310, 1159-63. The IL-2 binds the IL-2Rα with a low affinity ($K_d$≈10 nM). Id. From a crystal structure of a quaternary IL-2 signaling complex, fifteen amino acid residues (K35, T37, R38, T41, F42, K43, F44, Y45, E61, E62, K64, P65, E68, L72, and Y107) on the IL-2 are identified as interface residues between the IL-2 and IL-2Rα. Stauber et al., *Proc. Natl. Acad. Sci. U.S.A.* 2006, 103, 2788-93. The IL-2 binds a heterodimeric complex of the IL-2Rβ and IL-2Rγ, expressed on memory T cells and NK cells, with an intermediate affinity ($K_d$≈1 nM). Wang et al., *Science* 2005, 310, 1159-63. The IL-2 binds a heterotrimeric complex of the IL-2Rα, IL-2Rβ, and IL-2Rγ, expressed on Treg cells, with a high affinity ($K_d$≈10 pM). Id. The IL-2 binds the IL-2Rβ alone with a dissociation constant ($K_d$) of about 100 nM. Id. The IL-2Rα by itself has no signal-transducing activity. Id. The IL-2 signals through the intermediate-affinity heterodimeric IL-2Rβ/γ complex or the high-affinity heterotrimeric IL-2Rα/β/γ complex. Liao et al., *Curr. Opin. Immunol.* 2011, 23, 598-604. The binding of the IL-2 to the intermediate-affinity heterodimeric IL-2Rβ/γ complex leads to the activation and proliferation of immunostimulatory Teff cells, while the binding of the IL-2 to the high-affinity heterotrimeric IL-2Rα/β/γ complex results in the activation and proliferation of immunosuppressive Treg cells. Malek et al., *Immunity* 2010, 33, 153-65; Bluestone, *N. Engl. J. Med.* 2011, 365, 2129-2131; Boyman et al., *Nat. Rev. Immunol.* 2012, 12, 180-90; Spangler et al., *Annu. Rev. Immunol.* 2015, 33, 139-67. This dual opposing functions of immunostimulation and immunosuppression pose a major challenge in developing the IL-2 as a safe and effective therapeutic agent. Skrombolas et al., *Expert Rev. Clin. Immunol.* 2014, 10, 207-17; Abbas et al., *Sci. Immunol.* 2018, 3, eaat 1482.

Aldesleukin, a recombinant human IL-2, was approved by the FDA for metastatic renal cell carcinoma in 1992 and for metastatic melanoma in 1998. Rosenberg, *J. Immunol.* 2014, 192, 5451-8. Patients with metastatic melanoma or renal cancer experience a 5 to 10% rate of complete cancer regression, with an additional 10% experiencing a partial regression. Atkins et al., *J. Clin. Oncol.* 1999, 17, 2105-16; Klapper et al., *Cancer* 2008, 113, 293-301. Approximately 70% of complete responders to the IL-2 therapy do not recur. Rosenberg, *Sci. Transl. Med.* 2012, 4, 127ps8. However, the success of the IL-2 as an immunotherapy for cancer has been hampered by its severe toxicities and limited efficacy. One major limiting factor for its efficacy as an anticancer agent is immunosuppression resulting from the IL-2-driven preferential expansion of Treg cells. Abbas et al., *Sci. Immunol.* 2018, 3, eaat1482. Moreover, for the IL-2 to be effective in cancer treatment, a high dose therapeutic schedule is required. Bluestone, *N. Engl. J. Med.* 2011, 365, 2129-31; Abbas et al., *Sci. Immunol.* 2018, 3, eaat 1482. This dosing regimen, however, causes vascular leak syndrome and results in the limited application of IL-2 in cancer treatment. Abbas et al., *Sci. Immunol.* 2018, 3, eaat 1482. Moreover, aldesleukin has a half-life of only about 13 to 85 minutes in human following a 5-minute intravenous infusion. PROLEUKIN® Label (2012).

An interleukin-15 (IL-15) is a cytokine structurally similar to an IL-2. Waldmann, *Cancer Immunol. Res.* 2015, 3, 219-227. They also share two common receptor subunits: CD122 (IL-2Rβ/IL-15Rβ) and CD132 (IL-2Rγ). Waldmann et al., *Nat. Rev. Immunol.* 2006, 6, 595-601. An IL-15 plays pivotal roles in the control of the life and death of lymphocytes. Id. Like aldesleukin, however, the recombinant IL-2 used in a clinical trial for treating metastatic melanoma or metastatic renal cell cancer has a half-life of only about 2.5 hours in human following an intravenous infusion. Conlon et al., *J. Clin. Oncol.* 2015, 33, 74-82.

An interleukin-21 (IL-21) is a pleiotropic cytokine that regulates the activity of both innate and specific immunity. Croce et al., *J. Immunol. Res.* 2015, 696578. An IL-21 stimulates T and natural killer (NK) cell proliferation and function and regulates B cell survival and differentiation and the function of dendritic cells. Id. An interleukin-21 receptor (IL-21R) has been shown to be expressed in diverse hematopoietic malignancies, including chronic lymphocytic leukemia (CLL), follicular lymphoma, diffuse large B-cell lymphoma (DLBCL), and mantle cell lymphoma. Conlon et al., *J. Interferon Cytokine Res.* 2019, 39, 6-21. Several preclinical studies showed that IL-21 has antitumor activity in different tumor models, through mechanism involving the activation of NK and T or B cell responses. Croce et al., *J.*

*Immunol. Res.* 2015, 696578. However, just like aldesleukin, the recombinant IL-2 used in a clinical trial for treating metastatic melanoma has a half-life of only about 1 to 4 hours in human following an intravenous infusion. Davis et al., *Clin. Cancer Res.* 2007, 13, 3630-36.

Therefore, there is a need for an effective immunotherapy with an improved half-life for cancer treatment.

SUMMARY OF THE DISCLOSURE

Provided herein is a fusion protein comprising first and second cytokine domains, and a half-life extension domain; wherein the first and second cytokine domains are different. In one embodiment, the half-life extension domain is an albumin binding domain, a fragment crystallizable (Fc) domain, a serum albumin, a polyethylene glycol, or a fatty acyl group.

Also provided herein is a fusion protein comprising an interleukin domain that causes the fusion protein to signal through a receptor comprising CD122 (IL-2Rβ/IL-15Rβ) and CD132 (IL-2Rγ) subunits, an interleukin-21 domain, and a half-life extension domain.

Additionally, provided herein is a fusion protein comprising an interleukin-2 domain, an interleukin-21 domain, and a half-life extension domain.

Furthermore, provided herein is a fusion protein comprising an interleukin-2 domain, an interleukin-21 domain, and an albumin binding domain.

Provided herein is a fusion protein comprising an interleukin-2 domain, an interleukin-21 domain, an albumin binding domain, and optionally first and second peptide linkers; wherein the carboxy-terminus (C-terminus) of the interleukin-2 domain is connected to the amino-terminus (N-terminus) of the interleukin-21 domain directly or via the first peptide linker; and the C-terminus of the interleukin-21 domain is connected to the N-terminus of the albumin binding domain directly or via the second peptide linker.

Provided herein is a fusion protein comprising an interleukin-2 domain, an interleukin-21 domain, an albumin binding domain, and optionally first and second peptide linkers; wherein the C-terminus of the interleukin-21 domain is connected to the N-terminus of the interleukin-2 domain directly or via the first peptide linker; and the C-terminus of the interleukin-2 domain is connected to the N-terminus of the albumin binding domain directly or via the second peptide linker.

Provided herein is a fusion protein comprising an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker.

Provided herein is a fusion protein comprising an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker.

Provided herein is a fusion protein comprising an interleukin-2 domain, an interleukin-21 domain, an albumin binding domain, and optionally first and second peptide linkers; wherein the C-terminus of the albumin binding domain is connected to the N-terminus of the interleukin-2 domain directly or via the first peptide linker; and the C-terminus of the interleukin-2 domain is connected to the N-terminus of the interleukin-21 domain directly or via the second peptide linker.

Provided herein is a fusion protein comprising an interleukin-2 domain, an interleukin-21 domain, an albumin binding domain, and optionally first and second peptide linkers; wherein the C-terminus of the albumin binding domain is connected to the N-terminus of the interleukin-21 domain directly or via the first peptide linker; and the C-terminus of the interleukin-21 domain is connected to the N-terminus of the interleukin-2 domain directly or via the second peptide linker.

Provided herein is a fusion protein comprising an interleukin-2 domain, an interleukin-21 domain, and a fragment crystallizable (Fc) domain.

Provided herein is a fusion protein comprising an interleukin-2 domain, an interleukin-21 domain, an Fc domain having first and second peptide chains, and optionally first and second peptide linkers; wherein the C-terminus of the interleukin-2 domain is connected to the N-terminus of the first peptide chain of the Fc domain directly or via the first peptide linker; and the C-terminus of the interleukin-21 domain is connected to the N-terminus of the second peptide chain of the Fc domain directly or via the second peptide linker.

Provided herein is a fusion protein comprising an interleukin-2 domain, an interleukin-21 domain, an Fc domain having first and second peptide chains, and optionally first and second peptide linkers; wherein the N-terminus of the interleukin-2 domain is connected to the C-terminus of the first peptide chain of the Fc domain directly or via the first peptide linker; and the N-terminus of the interleukin-21 domain is connected to the C-terminus of the second peptide chain of the Fc domain directly or via the second peptide linker.

Provided herein is a fusion protein comprising an interleukin-2 domain, an interleukin-21 domain, an Fc domain having first and second peptide chains, and optionally first and second peptide linkers; wherein the C-terminus of the interleukin-2 domain is connected to the N-terminus of the first peptide chain of the Fc domain directly or via the first peptide linker; and the N-terminus of the interleukin-21 domain is connected to the C-terminus of the second peptide chain of the Fc domain directly or via the second peptide linker.

Provided herein is a fusion protein comprising an interleukin-2 domain, an interleukin-21 domain, an Fc domain having first and second peptide chains, and optionally first and second peptide linkers; wherein the N-terminus of the interleukin-2 domain is connected to the C-terminus of the first peptide chain of the Fc domain directly or via the first peptide linker; and the C-terminus of the interleukin-21 domain is connected to the N-terminus of the second peptide chain of the Fc domain directly or via the second peptide linker.

Provided herein is a fusion protein comprising first and second interleukin-2 domains, an interleukin-21 domain, an Fc domain having first and second peptide chains, and optionally a first, second, and third peptide linkers; wherein the C-terminus of the first interleukin-2 domain is connected to the N-terminus of the first peptide chain of the Fc domain directly or via the first peptide linker; the C-terminus of the second interleukin-2 domain is connected to the N-terminus of the second peptide chain of the Fc domain directly or via the second peptide linker; and the N-terminus of the interleukin-21 domain is connected to the C-terminus of the first peptide chain of the Fc domain directly or via the third peptide linker.

Provided herein is a fusion protein comprising first and second interleukin-2 domains, an interleukin-21 domain, an Fc domain having first and second peptide chains, and optionally a first, second, and third peptide linkers; wherein the N-terminus of the first interleukin-2 domain is connected to the C-terminus of the first peptide chain of the Fc domain directly or via the first peptide linker; the N-terminus of the second interleukin-2 domain is connected to the C-terminus of the second peptide chain of the Fc domain directly or via the second peptide linker; and the C-terminus of the interleukin-21 domain is connected to the N-terminus of the first peptide chain of the Fc domain directly or via the third peptide linker.

Provided herein is a fusion protein comprising first and second interleukin-2 domains, first and second interleukin-21 domains, an Fc domain having first and second peptide chains, and optionally a first, second, third, and fourth peptide linkers; wherein the C-terminus of the first interleukin-2 domain is connected to the N-terminus of the first peptide chain of the Fc domain directly or via the first peptide linker; the C-terminus of the second interleukin-2 domain is connected to the N-terminus of the second peptide chain of the Fc domain directly or via the second peptide linker; the N-terminus of the first interleukin-21 domain is connected to the C-terminus of the first peptide chain of the Fc domain directly or via the third peptide linker; and the N-terminus of the second interleukin-21 domain is connected to the C-terminus of the second peptide chain of the Fc domain directly or via the fourth peptide linker.

Provided herein is a fusion protein comprising first and second interleukin-2 domains, first and second interleukin-21 domains, an Fc domain having first and second peptide chains, and optionally a first, second, third, and fourth peptide linkers; wherein the N-terminus of the first interleukin-2 domain is connected to the C-terminus of the first peptide chain of the Fc domain directly or via the first peptide linker; the N-terminus of the second interleukin-2 domain is connected to the C-terminus of the second peptide chain of the Fc domain directly or via the second peptide linker; the C-terminus of the first interleukin-21 domain is connected to the N-terminus of the first peptide chain of the Fc domain directly or via the third peptide linker; and the C-terminus of the second interleukin-21 domain is connected to the N-terminus of the second peptide chain of the Fc domain directly or via the fourth peptide linker.

Provided herein is a fusion protein comprising first and second interleukin-2 domains, first and second interleukin-21 domains, an Fc domain having first and second peptide chains, and optionally a first, second, third, and fourth peptide linkers; wherein the N-terminus of the first interleukin-2 domain is connected to the C-terminus of the first peptide chain of the Fc domain directly or via the first peptide linker; the N-terminus of the second interleukin-2 domain is connected to the C-terminus of the second peptide chain of the Fc domain directly or via the second peptide linker; the N-terminus of the first interleukin-21 domain is connected to the C-terminus of the first peptide chain of the Fc domain directly or via the third peptide linker; and the C-terminus of the second interleukin-21 domain is connected to the N-terminus of the second peptide chain of the Fc domain directly or via the fourth peptide linker.

Provided herein is a pharmaceutical composition comprising a fusion protein provided herein and a pharmaceutically acceptable excipient.

Provided herein is a method of treating, preventing, or ameliorating one or more symptoms of a proliferative disease in a subject, comprising administering to the subject in need thereof a therapeutically effective amount of a fusion protein provided herein.

Provided herein is a method of activating an immune effector cell, comprising contacting the cell with an effective amount of a fusion protein provided herein.

DETAILED DESCRIPTION

Figure 1:
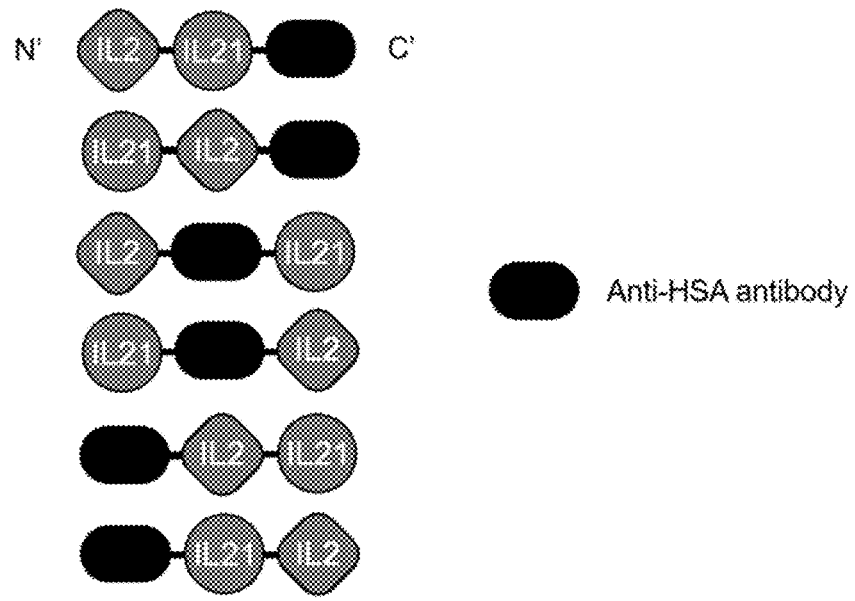
FIG. 1 shows the configurations of exemplary fusion proteins comprising an interleukin-2 (IL-2) domain, an interleukin-21 (IL-21) domain, and an anti-HSA antibody as an example of a half-life extension domain.
Figure 2:
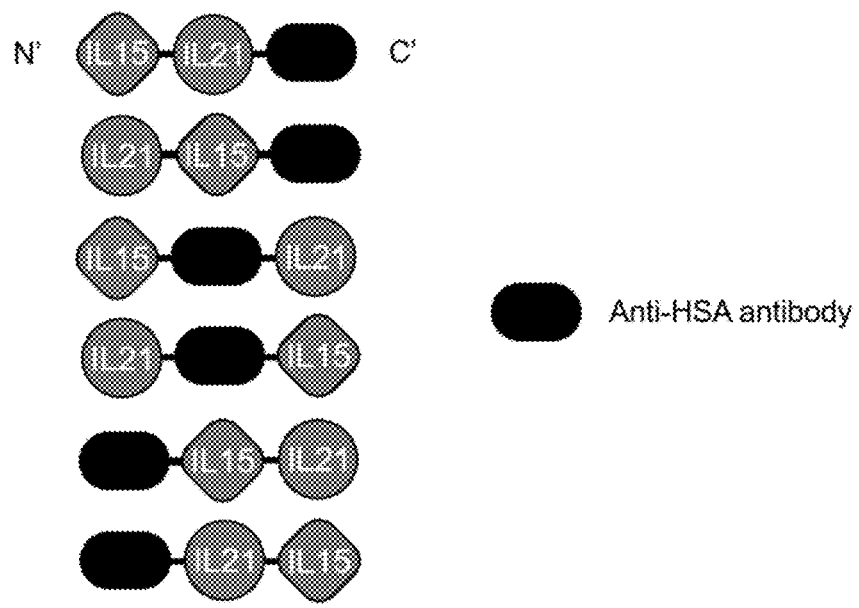
FIG. 2 shows the configurations of exemplary fusion proteins comprising an interleukin-15 (IL-15) domain, an IL-21 domain, and an anti-HSA antibody as an example of a half-life extension domain.
Figure 3:
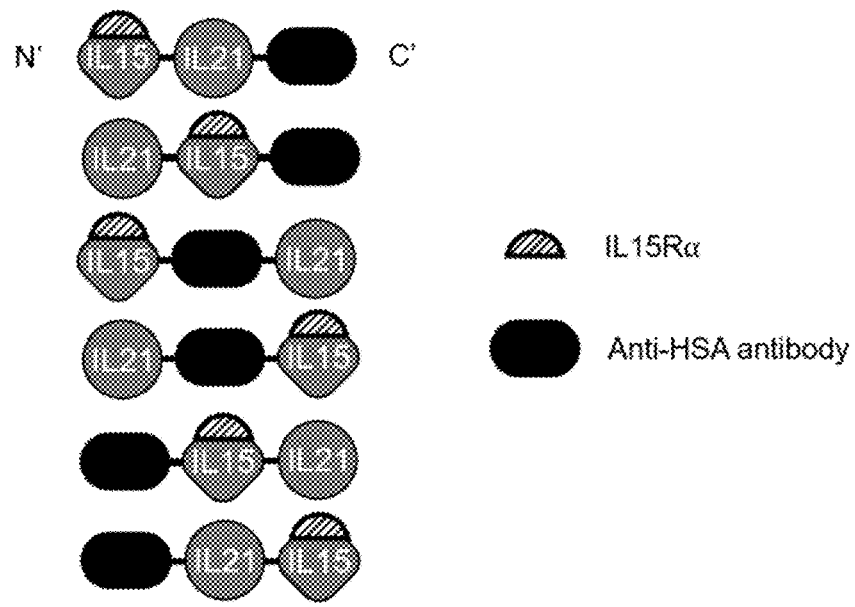
FIG. 3 shows the configurations of exemplary fusion proteins comprising an IL-15 variant domain, an IL-21 domain, and an anti-HSA antibody as an example of a half-life extension domain.

To facilitate understanding of the disclosure set forth herein, a number of terms are defined below.

Generally, the nomenclature used herein and the laboratory procedures in biochemistry, biology, cell biology, molecular biology, immunology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy,* 22nd ed.; Allen Ed.; The Pharmaceutical Press: 2012; *Handbook of Pharmaceutical Excipients,* 8th ed.; Sheskey et al., Eds.; The Pharmaceutical Press: 2017; *Handbook of Pharmaceutical Additives,* 3rd ed.; Ash and Ash Eds.; Synapse Information Resources, Inc.: 2007; *Pharmaceutical Preformulation and Formulation,* 2nd ed.; Gibson Ed.; CRC Press: 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "substantially pure" and "substantially homogeneous" mean sufficiently homogeneous to appear free of readily detectable impurities as determined by standard analytical methods used by one of ordinary skill in the art, including, but not limited to, gel electrophoresis, high performance liquid chromatography (HPLC), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound as determined by standard analytical methods.

Cytokine Fusion Proteins

In one embodiment, provided herein is a fusion protein comprising first and second cytokine domains, and a half-life extension domain; wherein the first and second cytokine domains are different.

In one embodiment, the first cytokine domain is an interleukin domain. In another embodiment, the second cytokine domain is an interleukin domain. In yet another embodiment, the first and second cytokine domains are each an interleukin domain.

In certain embodiments, the half-life extension domain extends the half-life of the first and/or second cytokine domains in vivo as compared to the corresponding free wild-type cytokines. In certain embodiments, the half-life extension domain extends the half-life of the first cytokine domain in vivo as compared to the corresponding free wild-type cytokine. In certain embodiments, the half-life extension domain extends the half-life of the second cytokine domain in vivo as compared to the corresponding free wild-type cytokine.

In certain embodiments, the half-life extension domain comprises an albumin binding domain, a fragment crystallizable (Fc) domain, a serum albumin, a polyethylene glycol (PEG), or a fatty acyl group. In one embodiment, the half-life extension domain is an albumin binding domain. In another embodiment, the half-life extension domain is an Fc domain. In yet another embodiment, the half-life extension domain is an Fc domain having first and second peptide chains. In yet another embodiment, the half-life extension domain is a serum albumin. In yet another embodiment, the half-life extension domain comprises a PEG. In still another embodiment, the half-life extension domain comprises a fatty acyl group.

In certain embodiments, the fusion protein provided herein has an affinity to the receptor of the first cytokine domain that is lower than that to the receptor of the second cytokine domain. In certain embodiments, the fusion protein provided herein has an affinity to the receptor of the first cytokine domain that is no less than about 2-fold, no less than about 5-fold, no less than about 10-fold, no less than about 20-fold, or no less than about 50-fold lower than that to the receptor of the second cytokine domain. In certain embodiments, the fusion protein provided herein has an affinity to the receptor of the first cytokine domain that is no less than about 2-fold lower than that to the receptor of the second cytokine domain. In certain embodiments, the fusion protein provided herein has an affinity to the receptor of the first cytokine domain that is no less than about 5-fold lower than that to the receptor of the second cytokine domain. In certain embodiments, the fusion protein provided herein has an affinity to the receptor of the first cytokine domain that is no less than about 10-fold lower than that to the receptor of the second cytokine domain. In certain embodiments, the fusion protein provided herein has an affinity to the receptor of the first cytokine domain that is no less than about 20-fold lower than that to the receptor of the second cytokine domain. In certain embodiments, the fusion protein provided herein has an affinity to the receptor of the first cytokine domain that is no less than about 50-fold lower than that to the receptor of the second cytokine domain.

In certain embodiments, the first cytokine domain comprises an amino acid sequence of an interleukin-2, or a variant or mutein thereof; or interleukin-15, or a variant or mutein thereof. In certain embodiments, the first cytokine domain comprises an amino acid sequence of an interleukin-2, or a variant or mutein thereof. In certain embodiments, the first cytokine domain comprises an amino acid sequence of an interleukin-15, or a variant or mutein thereof. In certain embodiments, the second cytokine domain comprises an amino acid sequence of an interleukin-21, or a variant or mutein thereof.

In one embodiment, the fusion protein provided herein has a biological activity of the corresponding cytokine of the first cytokine domain that is no less than about 2-fold, no less than about 5-fold, no less than about 10-fold, no less than about 20-fold, or no less than about 50-fold higher than that of the corresponding free cytokine. In another embodiment, the fusion protein provided herein has a biological activity of the corresponding cytokine of the first cytokine domain that is no less than about 2-fold higher than that of the corresponding free cytokine. In yet another embodiment, the fusion protein provided herein has a biological activity of the corresponding cytokine of the first cytokine domain that is no less than about 5-fold higher than that of the corresponding free cytokine. In yet another embodiment, the fusion protein provided herein has a biological activity of the corresponding cytokine of the first cytokine domain that is no less than about 10-fold higher than that of the corresponding free cytokine. In yet another embodiment, the fusion protein provided herein has a biological activity of the corresponding cytokine of the first cytokine domain that is no less than about 20-fold higher than that of the corresponding free cytokine. In still another embodiment, the fusion protein provided herein has a biological activity of the corresponding cytokine of the first cytokine domain that is no less than about 50-fold higher than that of the corresponding free cytokine.

In certain embodiments, the biological activity is STAT5 phosphorylation in a human T cell. In certain embodiments, the biological activity is proliferation of an activated human T cell. In certain embodiments, the biological activity is secretion of pro-inflammatory cytokines from a human T cell.

In another embodiment, provided herein is a fusion protein comprising a first interleukin domain that causes the fusion protein to signal through a receptor comprising an CD122 (IL-2Rβ/IL-15Rβ) and CD132 (IL-2Rγ) subunits, an interleukin-21 domain, and a half-life extension domain.

In one embodiment, the first interleukin domain comprises an amino acid sequence of an interleukin-2, or a variant or mutein thereof; or interleukin-15, or a variant or mutein thereof. In another embodiment, the first interleukin domain comprises an amino acid sequence of an interleukin-2, or a variant or mutein thereof. In yet another embodiment, the first interleukin domain comprises an amino acid sequence of an interleukin-15, or a variant or mutein thereof.

In one embodiment, the interleukin-15 domain in the fusion protein provided herein is a wide-type interleukin-15 domain. In another embodiment, the interleukin-15 domain in the fusion protein provided herein is a wild-type human interleukin-15 domain. In yet another embodiment, the interleukin-15 domain in the fusion protein provided herein is an interleukin-15 variant. In still another embodiment, the interleukin-15 domain in the fusion protein provided herein is an interleukin-15 mutein.

In certain embodiments, the interleukin-15 domain in the fusion protein provided herein comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 172.

In certain embodiments, the interleukin-15 domain in the fusion protein provided herein comprises an amino acid sequence that is no less than about 70% identical to an amino acid sequence of SEQ ID NO: 172. In certain embodiments, the interleukin-15 domain in the fusion protein provided herein comprises an amino acid sequence that is no less than about 75% identical to an amino acid sequence of SEQ ID NO: 172. In certain embodiments, the interleukin-15 domain in the fusion protein provided herein comprises an amino acid sequence that is no less than about 80% identical to an amino acid sequence of SEQ ID NO: 172. In certain embodiments, the interleukin-15 domain in the fusion protein provided herein comprises an amino acid sequence that is no less than about 85% identical to an amino acid sequence of SEQ ID NO: 172. In certain embodiments, the interleukin-15 domain in the fusion protein provided herein comprises an amino acid sequence that is no less than about 90% identical to an amino acid sequence of SEQ ID NO: 172. In certain embodiments, the interleukin-15 domain in the fusion protein provided herein comprises an amino acid sequence that is no less than about 91% identical to an amino acid sequence of SEQ ID NO: 172. In certain embodiments, the interleukin-15 domain in the fusion protein provided herein comprises an amino acid sequence that is no less than about 92% identical to an amino acid sequence of SEQ ID NO: 172. In certain embodiments, the interleukin-15 domain in the fusion protein provided herein comprises an amino acid sequence that is no less than about 93% identical to an amino acid sequence of SEQ ID NO: 172. In certain embodiments, the interleukin-15 domain in the fusion protein provided herein comprises an amino acid sequence that is no less than about 94% identical to an amino acid sequence of SEQ ID NO: 172. In certain embodiments, the interleukin-15 domain in the fusion protein provided herein comprises an amino acid sequence that is no less than about 95% identical to an amino acid sequence of SEQ ID NO: 172. In certain embodiments, the interleukin-15 domain in the fusion protein provided herein comprises an amino acid sequence that is no less than about 96% identical to an amino acid sequence of SEQ ID NO: 172. In certain embodiments, the interleukin-15 domain in the fusion protein provided herein comprises an amino acid sequence that is no less than about 97% identical to an amino acid sequence of SEQ ID NO: 172. In certain embodiments, the interleukin-15 domain in the fusion protein provided herein comprises an amino acid sequence that is no less than about 98% identical to an amino acid sequence of SEQ ID NO: 172. In certain embodiments, the interleukin-15 domain in the fusion protein provided herein comprises an amino acid sequence that is no less than about 99% identical to an amino acid sequence of SEQ ID NO: 172.

In certain embodiments, the interleukin-15 domain in the fusion protein provided herein is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 172.

In certain embodiments, the interleukin-15 domain in the fusion protein provided herein is no less than about 70% identical to an amino acid sequence of SEQ ID NO: 172. In certain embodiments, the interleukin-15 domain in the fusion protein provided herein is no less than about 75% identical to an amino acid sequence of SEQ ID NO: 172. In certain embodiments, the interleukin-15 domain in the fusion protein provided herein is no less than about 80% identical to an amino acid sequence of SEQ ID NO: 172. In certain embodiments, the interleukin-15 domain in the fusion protein provided herein is no less than about 85% identical to an amino acid sequence of SEQ ID NO: 172. In certain embodiments, the interleukin-15 domain in the fusion protein provided herein is no less than about 90% identical to an amino acid sequence of SEQ ID NO: 172. In certain embodiments, the interleukin-15 domain in the fusion protein provided herein is no less than about 91% identical to an amino acid sequence of SEQ ID NO: 172. In certain embodiments, the interleukin-15 domain in the fusion protein provided herein is no less than about 92% identical to an amino acid sequence of SEQ ID NO: 172. In certain embodiments, the interleukin-15 domain in the fusion protein provided herein is no less than about 93% identical to an amino acid sequence of SEQ ID NO: 172. In certain embodiments, the interleukin-15 domain in the fusion protein provided herein is no less than about 94% identical to an amino acid sequence of SEQ ID NO: 172. In certain embodiments, the interleukin-15 domain in the fusion protein provided herein is no less than about 95% identical to an amino acid sequence of SEQ ID NO: 172. In certain embodiments, the interleukin-15 domain in the fusion protein provided herein is no less than about 96% identical to an amino acid sequence of SEQ ID NO: 172. In certain embodiments, the interleukin-15 domain in the fusion protein provided herein is no less than about 97% identical to an amino acid sequence of SEQ ID NO: 172. In certain embodiments, the interleukin-15 domain in the fusion protein provided herein is no less than about 98% identical to an amino acid sequence of SEQ ID NO: 172. In certain embodiments, the interleukin-15 domain in the fusion protein provided herein is no less than about 99% identical to an amino acid sequence of SEQ ID NO: 172.

In yet another embodiment, provided herein is a fusion protein comprising an interleukin-2 domain, an interleukin-21 domain, and a half-life extension domain.

In certain embodiments, the half-life extension domain extends the half-life of the interleukin-2 domain and/or the interleukin-21 domain in vivo as compared to a wild-type interleukin-2 of SEQ ID NO: 1 or a wide-type interleukin-21 of SEQ ID NO: 156, respectively. In certain embodiments, the half-life extension domain extends the half-life of the interleukin-2 domain in vivo as compared to a wild-type interleukin-2 of SEQ ID NO: 1. In certain embodiments, the half-life extension domain extends the half-life of the interleukin-21 domain in vivo as compared to a wild-type interleukin-21 of SEQ ID NO: 156. In certain embodiments, the half-life extension domain extends the half-life of the interleukin-2 domain and the interleukin-21 domain in vivo as compared to a wild-type interleukin-2 of SEQ ID NO: 1 or a wide-type interleukin-21 of SEQ ID NO: 156, respectively.

In yet another embodiment, provided herein is a fusion protein comprising an interleukin-2 domain, an interleukin-21 domain, and an albumin binding domain.

In one embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the interleukin-21 domain directly or via the first peptide linker; and the C-terminus of the interleukin-21 domain is connected to the N-terminus of the albumin binding domain directly or via the second peptide linker.

In another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the interleukin-2 domain directly or via the first peptide linker; and the C-terminus of the interleukin-2 domain is connected to the N-terminus of the albumin binding domain directly or via the second peptide linker.

In yet another embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker.

In yet another embodiment, the fusion protein provided herein comprises an interleukin-2 domain, an interleukin-21 domain, and an albumin binding domain; wherein the C-terminus of the interleukin-2 domain is connected to the N-terminus of the albumin binding domain directly; and the C-terminus of the albumin binding domain is connected to the N-terminus of the interleukin-21 domain directly.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker.

In yet another embodiment, the fusion protein provided herein comprises an interleukin-2 domain, an interleukin-21 domain, an albumin binding domain, and first and second peptide linkers; wherein the C-terminus of the interleukin-2 domain is connected to the N-terminus of the albumin binding domain via the first peptide linker; and the C-terminus of the albumin binding domain is connected to the N-terminus of the interleukin-21 domain via the second peptide linker.

In yet another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker.

In yet another embodiment, the fusion protein provided herein comprises an interleukin-2 domain, an interleukin-21 domain, and an albumin binding domain; wherein the C-terminus of the interleukin-21 domain is connected to the N-terminus of the albumin binding domain directly; and the C-terminus of the albumin binding domain is connected to the N-terminus of the interleukin-2 domain directly.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain directly; and the C-terminus of the albumin binding domain is connected to the N-terminus of the interleukin-2 domain via the peptide linker.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain via the peptide linker; and the C-terminus of the albumin binding domain is connected to the N-terminus of the interleukin-2 domain directly.

In yet another embodiment, the fusion protein provided herein comprises an interleukin-2 domain, an interleukin-21 domain, an albumin binding domain, and first and second peptide linkers; wherein the C-terminus of the interleukin-21 domain is connected to the N-terminus of the albumin binding domain via the first peptide linker; and the C-terminus of the albumin binding domain is connected to the N-terminus of the interleukin-2 domain via the second peptide linker.

In one embodiment, the fusion protein provided herein consists of one interleukin-2 domain, one interleukin-21 domain, and one albumin binding domain.

In one embodiment, the fusion protein provided herein consists of one interleukin-2 domain, one interleukin-21 domain, and one albumin binding domain; wherein the C-terminus of the interleukin-2 domain is connected to the N-terminus of the albumin binding domain directly; and the C-terminus of the albumin binding domain is connected to the N-terminus of the interleukin-21 domain directly.

In another embodiment, the fusion protein provided herein consists of one interleukin-2 domain, one interleukin-21 domain, and one albumin binding domain; wherein the N-terminus of the interleukin-2 domain is connected to the C-terminus of the albumin binding domain directly; and the N-terminus of the albumin binding domain is connected to the C-terminus of the interleukin-21 domain directly.

In one embodiment, the fusion protein provided herein consists of one interleukin-2 domain, one interleukin-21 domain, one albumin binding domain, and one peptide linker.

In one embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly.

In another embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker.

In yet another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain via the peptide linker; and the N-terminus of the albumin binding domain is connected to the C-terminus of the interleukin-21 domain directly.

In still another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain directly; and the N-terminus of the albumin binding domain is connected to the C-terminus of the interleukin-21 domain via the peptide linker.

In yet another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-2 domain directly or via the first peptide linker; and the C-terminus of the interleukin-2 domain is connected to the N-terminus of the interleukin-21 domain directly or via the second peptide linker.

In still another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-21 domain directly or via the first peptide linker; and the C-terminus of the interleukin-21 domain is connected to the N-terminus of the interleukin-2 domain directly or via the second peptide linker.

In one embodiment, the albumin binding domain is an antibody or a fragment thereof that binds to an albumin. In another embodiment, the albumin binding domain is an antibody or a fragment thereof that binds to a human serum albumin (HSA).

In certain embodiments, the albumin binding domain binds to an HSA with a $K_d$ ranging from about 10 pM to about 1,000 nM. In certain embodiments, the albumin binding domain binds to an HSA with a $K_d$ ranging from about 1 nM to about 500 nM. In certain embodiments, the albumin binding domain binds to an HSA with a $K_d$ ranging from about 1 nM to about 200 nM. In certain embodiments, the albumin binding domain binds to an HSA with a $K_d$ ranging from about 1 nM to about 100 nM.

In one embodiment, the albumin binding domain is an antibody or a fragment thereof, comprising: (i) complementarity determining region 1 (CDR1) of SEQ ID NO: 101, complementarity determining region 2 (CDR2) of SEQ ID NO: 102, and complementarity determining region 3 (CDR3) of SEQ ID NO: 103; or (ii) CDR1 of SEQ ID NO: 109, CDR2 of SEQ ID NO: 110, and CDR3 of SEQ ID NO: 111. In another embodiment, the albumin binding domain comprises CDR1 of SEQ ID NO: 101, CDR2 of SEQ ID NO: 102, and CDR3 of SEQ ID NO: 103. In yet another embodiment, the albumin binding domain comprises CDR1 of SEQ ID NO: 109, CDR2 of SEQ ID NO: 110, and CDR3 of SEQ ID NO: 111. In certain embodiments, the CDRs provided herein are numbered using the IMGT numbering system. In yet another embodiment, the albumin binding domain has an amino acid sequence of SEQ ID NO: 108 or 115. In yet another embodiment, the albumin binding domain has an amino acid sequence of SEQ ID NO: 108. In still another embodiment, the albumin binding domain has an amino acid sequence of SEQ ID NO: 115.

In certain embodiments, the albumin binding domain has an amino acid sequence of one of anti-HSA antibodies disclosed in WO 2019/246003 A1 or WO 2019/246004 A1, the disclosure of each of which is incorporated herein by reference in its entirety.

In certain embodiments, the antibody or a fragment thereof is a human antibody. In certain embodiments, the antibody or a fragment thereof is a humanized antibody.

In another embodiment, the albumin binding domain is a single domain antibody (sdAb) that binds to an albumin. In certain embodiments, the albumin binding domain is an sdAb that binds to an HSA.

In certain embodiments, the sdAb binds to an HSA with a $K_d$ ranging from about 10 pM to about 1,000 nM. In certain embodiments, the sdAb binds to an HSA with a $K_d$ ranging from about 1 nM to about 500 nM. In certain embodiments, the sdAb binds to an HSA with a $K_d$ ranging from about 1 nM to about 200 nM. In certain embodiments, the sdAb binds to an HSA with a $K_d$ ranging from about 1 nM to about 100 nM.

In one embodiment, the sdAb comprises: (i) CDR1 of SEQ ID NO: 101, CDR2 of SEQ ID NO: 102, and CDR3 of SEQ ID NO: 103; or (ii) CDR1 of SEQ ID NO: 109, CDR2 of SEQ ID NO: 110, and CDR3 of SEQ ID NO: 111. In certain embodiments, the CDRs provided herein are numbered using the IMGT numbering system. In another embodiment, the sdAb comprises CDR1 of SEQ ID NO: 101, CDR2 of SEQ ID NO: 102, and CDR3 of SEQ ID NO: 103. In yet another embodiment, the sdAb comprises CDR1 of SEQ ID NO: 109, CDR2 of SEQ ID NO: 110, and CDR3 of SEQ ID NO: 111.

In one embodiment, the sdAb has the structure of FR1-CDR1-FR2-CDR2-FR3-CDR3-FR4, wherein:
CDR1, CDR2, and CDR3 are:
(i) CDR1 of SEQ ID NO: 101, CDR2 of SEQ ID NO: 102, and CDR3 of SEQ ID NO: 103; or
(ii) CDR1 of SEQ ID NO: 109, CDR2 of SEQ ID NO: 110, and CDR3 of SEQ ID NO: 111;
FR1 is an amino acid sequence of SEQ ID NO: 104 or 112;
FR2 is an amino acid sequence of SEQ ID NO: 105 or 113;
FR3 is an amino acid sequence of SEQ ID NO: 106; and
FR4 is an amino acid sequence of SEQ ID NO: 107 or 114.

In another embodiment, the sdAb has the structure of FR1-CDR1-FR2-CDR2-FR3-CDR3-FR4, wherein:
CDR1, CDR2, and CDR3 are:
(i) CDR1 of SEQ ID NO: 101, CDR2 of SEQ ID NO: 102, and CDR3 of SEQ ID NO: 103; or
(ii) CDR1 of SEQ ID NO: 109, CDR2 of SEQ ID NO: 110, and CDR3 of SEQ ID NO: 111;
FR1 is an amino acid sequence of SEQ ID NO: 104;
FR2 is an amino acid sequence of SEQ ID NO: 105;
FR3 is an amino acid sequence of SEQ ID NO: 106; and
FR3 is an amino acid sequence of SEQ ID NO: 107.

In yet another embodiment, the sdAb has the structure of FR1-CDR1-FR2-CDR2-FR3-CDR3-FR4, wherein:
CDR1, CDR2, and CDR3 are:
(i) CDR1 of SEQ ID NO: 101, CDR2 of SEQ ID NO: 102, and CDR3 of SEQ ID NO: 103; or
(ii) CDR1 of SEQ ID NO: 109, CDR2 of SEQ ID NO: 110, and CDR3 of SEQ ID NO: 111;
FR1 is an amino acid sequence of SEQ ID NO: 112;
FR2 is an amino acid sequence of SEQ ID NO: 113;
FR3 is an amino acid sequence of SEQ ID NO: 106; and
FR3 is an amino acid sequence of SEQ ID NO: 114.

In one embodiment, the sdAb has an amino acid sequence of SEQ ID NO: 108 or 115. In another embodiment, the sdAb has an amino acid sequence of SEQ ID NO: 108. In yet another embodiment, the sdAb has an amino acid sequence of SEQ ID NO: 115.

In certain embodiments, the sdAb has an amino acid sequence of one of anti-HSA sdAbs disclosed in WO 2019/246003 A1 or WO 2019/246004 A1, the disclosure of each of which is incorporated herein by reference in its entirety.

In certain embodiments, the sdAb is a human antibody. In certain embodiments, the sdAb is a humanized antibody.

In yet another embodiment, provided herein is a fusion protein comprising an interleukin-2 domain, an interleukin-21 domain, and an albumin binding domain; wherein the albumin binding domain is an sdAb.

In one embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the interleukin-21 domain directly or via the first peptide linker; and the C-terminus of the interleukin-21 domain is connected to the N-terminus of the albumin binding domain directly or via the second peptide linker; and wherein the albumin binding domain is an sdAb.

In another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the interleukin-2 domain directly or via the first peptide linker; and the C-terminus of the interleukin-2 domain is connected to the N-terminus of the albumin binding domain directly or via the second peptide linker; and wherein the albumin binding domain is an sdAb.

In yet another embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker; and wherein the albumin binding domain is an sdAb.

In yet another embodiment, the fusion protein provided herein comprises an interleukin-2 domain, an interleukin-21 domain, and an albumin binding domain; wherein the C-terminus of the interleukin-2 domain is connected to the N-terminus of the albumin binding domain directly; and the C-terminus of the albumin binding domain is connected to the N-terminus of the interleukin-21 domain directly; and wherein the albumin binding domain is an sdAb.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly; and wherein the albumin binding domain is an sdAb.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker; and wherein the albumin binding domain is an sdAb.

In yet another embodiment, the fusion protein provided herein comprises an interleukin-2 domain, an interleukin-21 domain, an albumin binding domain, and first and second peptide linkers; wherein the C-terminus of the interleukin-2 domain is connected to the N-terminus of the albumin binding domain via the first peptide linker; and the C-terminus of the albumin binding domain is connected to the N-terminus of the interleukin-21 domain via the second peptide linker; and wherein the albumin binding domain is an sdAb.

In yet another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker; and wherein the albumin binding domain is an sdAb.

In yet another embodiment, the fusion protein provided herein comprises an interleukin-2 domain, an interleukin-21 domain, and an albumin binding domain; wherein the C-terminus of the interleukin-21 domain is connected to the N-terminus of the albumin binding domain directly; and the C-terminus of the albumin binding domain is connected to the N-terminus of the interleukin-2 domain directly; and wherein the albumin binding domain is an sdAb.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain directly; and the C-terminus of the albumin binding domain is connected to the N-terminus of the interleukin-2 domain via the peptide linker; and wherein the albumin binding domain is an sdAb.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain via the peptide linker; and the C-terminus of the albumin binding domain is connected to the N-terminus of the interleukin-2 domain directly; and wherein the albumin binding domain is an sdAb.

In yet another embodiment, the fusion protein provided herein comprises an interleukin-2 domain, an interleukin-21 domain, an albumin binding domain, and first and second peptide linkers; wherein the C-terminus of the interleukin-21 domain is connected to the N-terminus of the albumin binding domain via the first peptide linker; and the C-terminus of the albumin binding domain is connected to the N-terminus of the interleukin-2 domain via the second peptide linker; and wherein the albumin binding domain is an sdAb.

In one embodiment, the fusion protein provided herein consists of one interleukin-2 domain, one interleukin-21 domain, and one albumin binding domain; wherein the albumin binding domain is an sdAb.

In one embodiment, the fusion protein provided herein consists of one interleukin-2 domain, one interleukin-21 domain, and one albumin binding domain; wherein the C-terminus of the interleukin-2 domain is connected to the N-terminus of the albumin binding domain directly; and the C-terminus of the albumin binding domain is connected to the N-terminus of the interleukin-21 domain directly; wherein the albumin binding domain is an sdAb.

In another embodiment, the fusion protein provided herein consists of one interleukin-2 domain, one interleukin-21 domain, and one albumin binding domain; wherein the N-terminus of the interleukin-2 domain is connected to the C-terminus of the albumin binding domain directly; and the N-terminus of the albumin binding domain is connected to the C-terminus of the interleukin-21 domain directly; wherein the albumin binding domain is an sdAb.

In one embodiment, the fusion protein provided herein consists of one interleukin-2 domain, one interleukin-21 domain, one albumin binding domain, and one peptide linker; wherein the albumin binding domain is an sdAb.

In one embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly; and wherein the albumin binding domain is an sdAb.

In another embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker; and wherein the albumin binding domain is an sdAb.

In yet another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain via the peptide linker; and the N-terminus of the albumin binding domain is connected to the C-terminus of the interleukin-21 domain directly; and wherein the albumin binding domain is an sdAb.

In still another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain directly; and the N-terminus of the albumin binding domain is connected to the C-terminus of the interleukin-21 domain via the peptide linker; and wherein the albumin binding domain is an sdAb.

In yet another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-2 domain directly or via the first peptide linker; and the C-terminus of the interleukin-2 domain is connected to the N-terminus of the interleukin-21 domain directly or via the second peptide linker; and wherein the albumin binding domain is an sdAb.

In still another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-21 domain directly or via the first peptide linker; and the C-terminus of the interleukin-21 domain is connected to the N-terminus of the interleukin-2 domain directly or via the second peptide linker; and wherein the albumin binding domain is an sdAb.

In yet another embodiment, the albumin binding domain is a $V_HH$ single domain antibody that binds to an albumin. In certain embodiments, the albumin binding domain is $V_HH$ single domain antibody that binds to an HSA.

In certain embodiments, the $V_HH$ single domain antibody binds to an HSA with a $K_d$ ranging from about 10 pM to about 1,000 nM. In certain embodiments, the $V_HH$ single domain antibody binds to an HSA with a $K_d$ ranging from about 1 nM to about 500 nM. In certain embodiments, the $V_HH$ single domain antibody binds to an HSA with a $K_d$ ranging from about 1 nM to about 200 nM. In certain embodiments, the $V_HH$ single domain antibody binds to an HSA with a $K_d$ ranging from about 1 nM to about 100 nM.

In one embodiment, the $V_HH$ single domain antibody comprises: (i) heavy chain CDR1 of SEQ ID NO: 101, heavy chain CDR2 of SEQ ID NO: 102, and heavy chain CDR3 of SEQ ID NO: 103; or (ii) heavy chain CDR1 of SEQ ID NO: 109, heavy chain CDR2 of SEQ ID NO: 110, and heavy chain CDR3 of SEQ ID NO: 111. In certain embodiments, the CDRs provided herein are numbered using the IMGT numbering system. In another embodiment, the $V_HH$ single domain antibody comprises heavy chain CDR1 of SEQ ID NO: 101, heavy chain CDR2 of SEQ ID NO: 102, and heavy chain CDR3 of SEQ ID NO: 103. In yet another embodiment, the $V_HH$ single domain antibody comprises heavy chain CDR1 of SEQ ID NO: 109, heavy chain CDR2 of SEQ ID NO: 110, and heavy chain CDR3 of SEQ ID NO: 111.

In one embodiment, the $V_HH$ single domain antibody has the structure of FR1-CDR1-FR2-CDR2-FR3-CDR3-FR4, wherein:
  CDR1, CDR2, and CDR3 are:
  (i) CDR1 of SEQ ID NO: 101, CDR2 of SEQ ID NO: 102, and CDR3 of SEQ ID NO: 103; or
  (ii) CDR1 of SEQ ID NO: 109, CDR2 of SEQ ID NO: 110, and CDR3 of SEQ ID NO: 111;
  FR1 is an amino acid sequence of SEQ ID NO: 104 or 112;
  FR2 is an amino acid sequence of SEQ ID NO: 105 or 113;
  FR3 is an amino acid sequence of SEQ ID NO: 106; and
  FR4 is an amino acid sequence of SEQ ID NO: 107 or 114.

In another embodiment, the $V_HH$ single domain antibody has the structure of FR1-CDR1-FR2-CDR2-FR3-CDR3-FR4, wherein:
  CDR1, CDR2, and CDR3 are:
  (i) CDR1 of SEQ ID NO: 101, CDR2 of SEQ ID NO: 102, and CDR3 of SEQ ID NO: 103; or
  (ii) CDR1 of SEQ ID NO: 109, CDR2 of SEQ ID NO: 110, and CDR3 of SEQ ID NO: 111;
  FR1 is an amino acid sequence of SEQ ID NO: 104;
  FR2 is an amino acid sequence of SEQ ID NO: 105;
  FR3 is an amino acid sequence of SEQ ID NO: 106; and
  FR4 is an amino acid sequence of SEQ ID NO: 107.

In yet another embodiment, the $V_HH$ single domain antibody has the structure of FR1-CDR1-FR2-CDR2-FR3-CDR3-FR4, wherein:
  CDR1, CDR2, and CDR3 are:
  (i) CDR1 of SEQ ID NO: 101, CDR2 of SEQ ID NO: 102, and CDR3 of SEQ ID NO: 103; or
  (ii) CDR1 of SEQ ID NO: 109, CDR2 of SEQ ID NO: 110, and CDR3 of SEQ ID NO: 111;
  FR1 is an amino acid sequence of SEQ ID NO: 112;
  FR2 is an amino acid sequence of SEQ ID NO: 113;
  FR3 is an amino acid sequence of SEQ ID NO: 106; and
  FR4 is an amino acid sequence of SEQ ID NO: 114.

In one embodiment, the $V_HH$ single domain antibody has an amino acid sequence of SEQ ID NO: 108 or 115. In another embodiment, the $V_HH$ single domain antibody has an amino acid sequence of SEQ ID NO: 108. In yet another embodiment, the $V_HH$ single domain antibody has an amino acid sequence of SEQ ID NO: 115.

In certain embodiments, the $V_HH$ single domain antibody has an amino acid sequence of one of $V_HH$ single domain antibodies disclosed in WO 2019/246003 A1 or WO 2019/246004 A1, the disclosure of each of which is incorporated herein by reference in its entirety.

In certain embodiments, the $V_HH$ single domain antibody is a human antibody. In certain embodiments, the $V_HH$ single domain antibody is a humanized antibody.

In yet another embodiment, provided herein is a fusion protein comprising an interleukin-2 domain, an interleukin-21 domain, and an albumin binding domain; wherein the albumin binding domain is a $V_HH$ single domain antibody.

In one embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the interleukin-21 domain directly or via the first peptide linker; and the C-terminus of the interleukin-21 domain is connected to the N-terminus of the albumin binding domain directly or via the second peptide linker; and wherein the albumin binding domain is a $V_HH$ single domain antibody.

In another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the interleukin-2 domain directly or via the first peptide linker; and the C-terminus of the interleukin-2 domain is connected to the N-terminus of the albumin binding domain directly or via the second peptide linker; and wherein the albumin binding domain is a $V_HH$ single domain antibody.

In yet another embodiment, the fusion protein provided herein comprises an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker; and wherein the albumin binding domain is a $V_HH$ single domain antibody.

In yet another embodiment, the fusion protein provided herein comprises an interleukin-2 domain, an interleukin-21 domain, and an albumin binding domain; wherein the C-terminus of the interleukin-2 domain is connected to the N-terminus of the albumin binding domain directly; and the C-terminus of the albumin binding domain is connected to the N-terminus of the interleukin-21 domain directly; and wherein the albumin binding domain is a $V_HH$ single domain antibody.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly; and wherein the albumin binding domain is a $V_HH$ single domain antibody.

In yet another embodiment, the fusion protein provided herein comprises an interleukin-2 domain, an interleukin-21 domain, an albumin binding domain, and a peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker; and wherein the albumin binding domain is a $V_HH$ single domain antibody.

In yet another embodiment, the fusion protein provided herein comprises an interleukin-2 domain, an interleukin-21 domain, an albumin binding domain, and first and second peptide linkers; wherein the C-terminus of the interleukin-2 domain is connected to the N-terminus of the albumin binding domain via the first peptide linker; and the C-terminus of the albumin binding domain is connected to the N-terminus of the interleukin-21 domain via the second peptide linker; and wherein the albumin binding domain is a $V_HH$ single domain antibody.

In yet another embodiment, the fusion protein provided herein comprises an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker; and wherein the albumin binding domain is a $V_HH$ single domain antibody.

In yet another embodiment, the fusion protein provided herein comprises an interleukin-2 domain, an interleukin-21 domain, and an albumin binding domain; wherein the C-terminus of the interleukin-21 domain is connected to the N-terminus of the albumin binding domain directly; and the C-terminus of the albumin binding domain is connected to the N-terminus of the interleukin-2 domain directly; and wherein the albumin binding domain is a $V_HH$ single domain antibody.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain directly; and the C-terminus of the albumin binding domain is connected to the N-terminus of the interleukin-2 domain via the peptide linker; and wherein the albumin binding domain is a $V_HH$ single domain antibody.

In yet another embodiment, the fusion protein provided herein comprises an interleukin-2 domain, an interleukin-21 domain, an albumin binding domain, and a peptide linker; wherein the C-terminus of the interleukin-21 domain is connected to the N-terminus of the albumin binding domain via the peptide linker; and the C-terminus of the albumin binding domain is connected to the N-terminus of the interleukin-2 domain directly; and wherein the albumin binding domain is a $V_HH$ single domain antibody.

In yet another embodiment, the fusion protein provided herein comprises an interleukin-2 domain, an interleukin-21 domain, an albumin binding domain, and first and second peptide linkers; wherein the C-terminus of the interleukin-21 domain is connected to the N-terminus of the albumin binding domain via the first peptide linker; and the C-terminus of the albumin binding domain is connected to the N-terminus of the interleukin-2 domain via the second peptide linker; and wherein the albumin binding domain is a $V_HH$ single domain antibody.

In one embodiment, the fusion protein provided herein consists of one interleukin-2 domain, one interleukin-21 domain, and one albumin binding domain; and wherein the albumin binding domain is a $V_HH$ single domain antibody.

In one embodiment, the fusion protein provided herein consists of one interleukin-2 domain, one interleukin-21 domain, and one albumin binding domain; wherein the C-terminus of the interleukin-2 domain is connected to the N-terminus of the albumin binding domain directly; and the C-terminus of the albumin binding domain is connected to the N-terminus of the interleukin-21 domain directly; and wherein the albumin binding domain is a $V_HH$ single domain antibody.

In another embodiment, the fusion protein provided herein consists of one interleukin-2 domain, one interleukin-21 domain, and one albumin binding domain; wherein the N-terminus of the interleukin-2 domain is connected to the C-terminus of the albumin binding domain directly; and the N-terminus of the albumin binding domain is connected to the C-terminus of the interleukin-21 domain directly; and wherein the albumin binding domain is a $V_HH$ single domain antibody.

In one embodiment, the fusion protein provided herein consists of one interleukin-2 domain, one interleukin-21 domain, one albumin binding domain, and one peptide linker; wherein the albumin binding domain is a $V_HH$ single domain antibody.

In one embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain via the peptide linker; and the C-terminus of the albumin binding domain is connected to the N-terminus of the interleukin-21 domain directly; and wherein the albumin binding domain is a $V_HH$ single domain antibody.

In another embodiment, the fusion protein provided herein consists of one interleukin-2 domain, one interleukin-21 domain, one albumin binding domain, and one peptide linker; wherein the C-terminus of the interleukin-2 domain is connected to the N-terminus of the albumin binding domain directly; and the C-terminus of the albumin binding domain is connected to the N-terminus of the interleukin-21 domain via the peptide linker; and wherein the albumin binding domain is a $V_HH$ single domain antibody.

In yet another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain via the peptide linker; and the N-terminus of the albumin binding domain is connected to the C-terminus of the interleukin-21 domain directly; and wherein the albumin binding domain is a $V_HH$ single domain antibody.

In still another embodiment, the fusion protein provided herein consists of one interleukin-2 domain, one interleukin-21 domain, one albumin binding domain, and one peptide linker; wherein the N-terminus of the interleukin-2 domain is connected to the C-terminus of the albumin binding domain directly; and the N-terminus of the albumin binding domain is connected to the C-terminus of the interleukin-21 domain via the peptide linker; and wherein the albumin binding domain is a $V_HH$ single domain antibody.

In yet another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-2 domain directly or via the first peptide linker; and the C-terminus of the interleukin-2 domain is connected to the N-terminus of the interleukin-21 domain directly or via the second peptide linker; and wherein the albumin binding domain is a $V_HH$ single domain antibody.

In still another embodiment, the fusion protein provided herein comprises an interleukin-2 domain, an interleukin-21 domain, an albumin binding domain, and optionally first and second peptide linkers; wherein the C-terminus of the albumin binding domain is connected to the N-terminus of the interleukin-21 domain directly or via the first peptide linker; and the C-terminus of the interleukin-21 domain is connected to the N-terminus of the interleukin-2 domain directly or via the second peptide linker; and wherein the albumin binding domain is a $V_HH$ single domain antibody.

In still another embodiment, provided herein is a fusion protein comprising an interleukin-2 domain, an interleukin-21 domain, and an Fc domain.

In one embodiment, the fusion protein provided herein comprises an interleukin-2 domain, an interleukin-21 domain, an Fc domain having first and second peptide chains, and optionally first and second peptide linkers; wherein the C-terminus of the interleukin-2 domain is connected to the N-terminus of the first peptide chain of the Fc domain directly or via the first peptide linker; and the C-terminus of the interleukin-21 domain is connected to the N-terminus of the second peptide chain of the Fc domain directly or via the second peptide linker.

In another embodiment, the fusion protein provided herein comprises an interleukin-2 domain, an interleukin-21 domain, an Fc domain having first and second peptide chains, and optionally first and second peptide linkers; wherein the N-terminus of the interleukin-2 domain is connected to the C-terminus of the first peptide chain of the Fc domain directly or via the first peptide linker; and the N-terminus of the interleukin-21 domain is connected to the C-terminus of the second peptide chain of the Fc domain directly or via the second peptide linker.

In yet another embodiment, the fusion protein provided herein comprises an interleukin-2 domain, an interleukin-21 domain, an Fc domain having first and second peptide chains, and optionally first and second peptide linkers; wherein the C-terminus of the interleukin-2 domain is connected to the N-terminus of the first peptide chain of the Fc domain directly or via the first peptide linker; and the N-terminus of the interleukin-21 domain is connected to the C-terminus of the second peptide chain of the Fc domain directly or via the second peptide linker.

In yet another embodiment, the fusion protein provided herein comprises an interleukin-2 domain, an interleukin-21 domain, an Fc domain having first and second peptide chains, and optionally first and second peptide linkers; wherein the N-terminus of the interleukin-2 domain is connected to the C-terminus of the first peptide chain of the Fc domain directly or via the first peptide linker; and the C-terminus of the interleukin-21 domain is connected to the N-terminus of the second peptide chain of the Fc domain directly or via the second peptide linker.

In yet another embodiment, the fusion protein provided herein comprises first and second interleukin-2 domains, an interleukin-21 domain, an Fc domain having first and second peptide chains, and optionally a first, second, and third peptide linkers; wherein the C-terminus of the first interleukin-2 domain is connected to the N-terminus of the first peptide chain of the Fc domain directly or via the first peptide linker; the C-terminus of the second interleukin-2 domain is connected to the N-terminus of the second peptide chain of the Fc domain directly or via the second peptide linker; and the N-terminus of the interleukin-21 domain is connected to the C-terminus of the first peptide chain of the Fc domain directly or via the third peptide linker.

In yet another embodiment, the fusion protein provided herein comprises first and second interleukin-2 domains, an interleukin-21 domain, an Fc domain having first and second peptide chains, and optionally a first, second, and third peptide linkers; wherein the N-terminus of the first interleukin-2 domain is connected to the C-terminus of the first peptide chain of the Fc domain directly or via the first peptide linker; the N-terminus of the second interleukin-2 domain is connected to the C-terminus of the second peptide chain of the Fc domain directly or via the second peptide linker; and the C-terminus of the interleukin-21 domain is connected to the N-terminus of the first peptide chain of the Fc domain directly or via the third peptide linker.

In yet another embodiment, provided herein is a fusion protein comprising first and second interleukin-2 domains, first and second interleukin-21 domains, an Fc domain having first and second peptide chains, and optionally a first, second, third, and fourth peptide linkers; wherein the C-terminus of the first interleukin-2 domain is connected to the N-terminus of the first peptide chain of the Fc domain directly or via the first peptide linker; the C-terminus of the second interleukin-2 domain is connected to the N-terminus of the second peptide chain of the Fc domain directly or via the second peptide linker; the N-terminus of the first interleukin-21 domain is connected to the C-terminus of the first peptide chain of the Fc domain directly or via the third peptide linker; and the N-terminus of the second interleukin-21 domain is connected to the C-terminus of the second peptide chain of the Fc domain directly or via the fourth peptide linker.

In yet another embodiment, provided herein is a fusion protein comprising first and second interleukin-2 domains, first and second interleukin-21 domains, an Fc domain having first and second peptide chains, and optionally a first, second, third, and fourth peptide linkers; wherein the N-terminus of the first interleukin-2 domain is connected to the C-terminus of the first peptide chain of the Fc domain directly or via the first peptide linker; the N-terminus of the second interleukin-2 domain is connected to the C-terminus of the second peptide chain of the Fc domain directly or via the second peptide linker; the C-terminus of the first interleukin-21 domain is connected to the N-terminus of the first peptide chain of the Fc domain directly or via the third peptide linker; and the C-terminus of the second interleukin-21 domain is connected to the N-terminus of the second peptide chain of the Fc domain directly or via the fourth peptide linker.

In still another embodiment, provided herein is a fusion protein comprising first and second interleukin-2 domains, first and second interleukin-21 domains, an Fc domain having first and second peptide chains, and optionally a first, second, third, and fourth peptide linkers; wherein the C-terminus of the first interleukin-2 domain is connected to the N-terminus of the first peptide chain of the Fc domain directly or via the first peptide linker; the N-terminus of the second interleukin-2 domain is connected to the C-terminus of the second peptide chain of the Fc domain directly or via the second peptide linker; the N-terminus of the first interleukin-21 domain is connected to the C-terminus of the first peptide chain of the Fc domain directly or via the third peptide linker; and the C-terminus of the second interleukin-21 domain is connected to the N-terminus of the second peptide chain of the Fc domain directly or via the fourth peptide linker.

In one embodiment, the Fc domain is a hIgG1 Fc domain or a mutein thereof, or a fragment thereof. In another embodiment, the Fc domain is a hIgG1 Fc chain 1 or a mutein thereof, or a fragment thereof. In yet another embodiment, the Fc domain is a hIgG1 Fc chain 2 or a mutein thereof, or a fragment thereof. In another embodiment, the Fc domain is a hIgG2 Fc domain or a mutein thereof, or a fragment thereof. In still another embodiment, the Fc domain is a hIgG4 Fc domain or a mutein thereof, or a fragment thereof.

In one embodiment, the Fc domain comprises an amino acid sequence of SEQ ID NO: 116, 117, 118, 119, 120, 121, 122, or 123. In yet another embodiment, the Fc domain comprises an amino acid sequence of SEQ ID NO: 116. In another embodiment, the Fc domain comprises an amino acid sequence of SEQ ID NO: 117. In yet another embodiment, the Fc domain comprises an amino acid sequence of SEQ ID NO: 118. In yet another embodiment, the Fc domain comprises an amino acid sequence of SEQ ID NO: 119. In yet another embodiment, the Fc domain comprises an amino acid sequence of SEQ ID NO: 120. In yet another embodiment, the Fc domain comprises an amino acid sequence of SEQ ID NO: 121. In yet another embodiment, the Fc domain comprises an amino acid sequence of SEQ ID NO: 122. In still another embodiment, the Fc domain comprises an amino acid sequence of SEQ ID NO: 123.

In one embodiment, the Fc domain comprises a pair of chains in a knobs-in-holes configuration.

In one embodiment, the interleukin-2 domain in the fusion protein provided herein comprises an amino acid sequence of a wide-type interleukin-2. In another embodiment, the interleukin-2 domain in the fusion protein provided herein comprises an amino acid sequence of a wild-type human interleukin-2.

In one embodiment, the interleukin-2 domain in the fusion protein provided herein has an amino acid sequence of SEQ ID NO: 1, 2, 3, 4, or 5. In another embodiment, the interleukin-2 domain in the fusion protein provided herein has an amino acid sequence of SEQ ID NO: 1. In yet another embodiment, the interleukin-2 domain in the fusion protein provided herein has an amino acid sequence of SEQ ID NO: 2. In yet another embodiment, the interleukin-2 domain in the fusion protein provided herein has an amino acid sequence of SEQ ID NO: 3. In yet another embodiment, the interleukin-2 domain in the fusion protein provided herein has an amino acid sequence of SEQ ID NO: 4. In still another embodiment, the interleukin-2 domain in the fusion protein provided herein has an amino acid sequence of SEQ ID NO: 5.

In one embodiment, the interleukin-2 domain in the fusion protein provided herein is glycosylated. In another embodiment, the interleukin-2 domain in the fusion protein provided herein is N-glycosylated.

In one embodiment, the fusion protein containing the N-glycosylated interleukin-2 domain has a reduced binding affinity to an interleukin-2 receptor-α (IL-2Rα) chain as compared to a wild-type interleukin-2. In certain embodiments, the binding affinity of the fusion protein to an interleukin-2 receptor-α (IL-2Rα) is measured by its association constant ($K_a$), which is the inverse of its dissociation constant ($K_d$).

In certain embodiments, the fusion protein containing the N-glycosylated interleukin-2 domain has a $K_d$ to the IL-2Rα of no less than about 2 times, no less than about 5 times, no less than about 10 times, no less than about 100 times, or no less than about 1,000 times higher than that of the wild-type interleukin-2 to the IL-2Rα. In one embodiment, the fusion protein containing the N-glycosylated interleukin-2 domain has a $K_d$ to the IL-2Rα of no less than about 2 times higher than that of the wild-type interleukin-2 to the IL-2Rα. In another embodiment, the fusion protein containing the N-glycosylated interleukin-2 domain has a $K_d$ to the IL-2Rα of no less than about 5 times higher than that of the wild-type interleukin-2 to the IL-2Rα. In yet another embodiment, the fusion protein containing the N-glycosylated interleukin-2 domain has a $K_d$ to the IL-2Rα of no less than about 10 times higher than that of the wild-type interleukin-2 to the IL-2Rα. In yet another embodiment, the fusion protein containing the N-glycosylated interleukin-2 domain has a $K_d$ to the IL-2Rα of no less than about 100 times higher than that of the wild-type interleukin-2 to the IL-2Rα. In still another embodiment, the fusion protein containing the N-glycosylated interleukin-2 domain has a $K_d$ to the IL-2Rα of no less than about 1,000 times higher than that of the wild-type interleukin-2 to the IL-2Rα.

In one embodiment, the wild-type interleukin-2 is a human wild-type interleukin-2. In another embodiment, the human wild-type interleukin-2 has an amino acid sequence of SEQ ID NO: 1, 2, 3, 4, or 5. In yet another embodiment, the human wild-type interleukin-2 has an amino acid sequence of SEQ ID NO: 1. In yet another embodiment, the human wild-type interleukin-2 has an amino acid sequence of SEQ ID NO: 2. In yet another embodiment, the human wild-type interleukin-2 has an amino acid sequence of SEQ ID NO: 3. In yet another embodiment, the human wild-type interleukin-2 has an amino acid sequence of SEQ ID NO: 4. In still another embodiment, the human wild-type interleukin-2 has an amino acid sequence of SEQ ID NO: 5.

In one embodiment, the fusion protein containing the N-glycosylated interleukin-2 domain has a $K_d$ to an IL-2Rα of no less than about 20 nM, no less than about 50 nM, no less than about 100 nM, no less than about 1 μM, no less than about 10 μM, no less than about 100 μM, or no less than about 1 mM. In certain embodiments, the fusion protein containing the N-glycosylated interleukin-2 domain has a $K_d$ to the IL-2Rα of no less than about 20 nM. In certain embodiments, the fusion protein containing the N-glycosylated interleukin-2 domain has a $K_d$ to the IL-2Rα of no less than about 50 nM. In certain embodiments, the fusion protein containing the N-glycosylated interleukin-2 domain has a $K_d$ to the IL-2Rα of no less than about 100 nM. In certain embodiments, the fusion protein containing the N-glycosylated interleukin-2 domain has a $K_d$ to the IL-2Rα of no less than about 1 μM. In certain embodiments, the fusion protein containing the N-glycosylated interleukin-2 domain has a $K_d$ to the IL-2Rα receptor (CD25) of no less than about 10 μM. In certain embodiments, the fusion protein containing the N-glycosylated interleukin-2 domain has a $K_d$ to the IL-2Rα of no less than about 100 μM. In certain embodiments, the fusion protein containing the N-glycosylated interleukin-2 domain has a $K_d$ to the IL-2Rα of no less than about 1 mM. In certain embodiments, the fusion protein containing the N-glycosylated interleukin-2 domain has no measurable binding to the IL-2Rα. In certain embodiments, the fusion protein containing the N-glycosylated interleukin-2 domain has no detectable binding to the IL-2Rα as measured with a surface plasmon resonance (SPR) method. In certain embodiments, the fusion protein containing the N-glycosylated interleukin-2 domain has no detectable binding to the IL-2Rα as measured with bio-layer interferometry (BLI).

In yet another embodiment, the fusion protein containing the N-glycosylated interleukin-2 domain has a selectivity for an IL-2Rβ over an IL-2Rα; wherein the selectivity is no greater than about 1, no greater than about 0.5, no greater than about 0.2, no greater than about 0.1, no greater than about 0.01, or no greater than about 0.001; and wherein the selectivity is measured as a ratio of a $K_d$ of the fusion protein to the IL-2Rβ over a $K_d$ of the fusion protein to the IL-2Rα. In certain embodiments, the fusion protein containing the N-glycosylated interleukin-2 domain has a selectivity of no greater than about 1. In certain embodiments, the fusion protein containing the N-glycosylated interleukin-2 domain has a selectivity of no greater than about 0.5. In certain embodiments, the fusion protein containing the N-glycosylated interleukin-2 domain has a selectivity of no greater than about 0.2. In certain embodiments, the fusion protein containing the N-glycosylated interleukin-2 domain has a selectivity of no greater than about 0.1. In certain embodiments, the fusion protein containing the N-glycosylated interleukin-2 domain has a selectivity of no greater than about 0.01. In certain embodiments, the fusion protein containing the N-glycosylated interleukin-2 domain has a selectivity of no greater than about 0.001.

In one embodiment, the IL-2Rα is a human IL-2Rα. In another embodiment, the human IL-2Rα has an amino acid sequence of SEQ ID NO: 98.

In one embodiment, the IL-2Rβ is a human IL-2Rβ. In another embodiment, the human IL-2Rβ has an amino acid sequence of SEQ ID NO: 99.

In one embodiment, the dissociation constant of the fusion protein to an IL-2Rα is determined with a surface plasmon resonance (SPR) method. In another embodiment, the dissociation constant of the fusion protein to an IL-2Rα is determined with a BIACORE® assay. In yet another embodiment, the dissociation constant of the fusion protein to an IL-2Rα is determined with bio-layer interferometry (BLI). In still another embodiment, the dissociation constant of the fusion protein to an IL-2Rα is determined with an OCTET® assay.

In one embodiment, the dissociation constant of the fusion protein to an IL-2Rβ is determined with a SPR method. In another embodiment, the dissociation constant of the fusion protein to an IL-2Rβ is determined with a BIACORE® assay. In yet another embodiment, the dissociation constant of the fusion protein to an IL-2Rβ is determined with BLI. In still another embodiment, the dissociation constant of the fusion protein to an IL-2Rβ is determined with an OCTET® assay.

In yet another embodiment, the fusion protein containing the N-glycosylated interleukin-2 domain has a selectivity for an IL-2Rβ and IL-2Rγ complex over an IL-2Rα; wherein the selectivity is no greater than about 0.01 or no greater than about 0.001; and wherein the selectivity is measured as a ratio of a $K_d$ of the fusion protein to the IL-2Rβ and IL-2Rγ complex over a $K_d$ of the fusion protein to the IL-2Rα. In certain embodiments, the fusion protein containing the N-glycosylated interleukin-2 domain has a selectivity of no greater than about 0.01. In certain embodiments, the fusion protein containing the N-glycosylated interleukin-2 domain has a selectivity of no greater than about 0.001. In one embodiment, the dissociation constants of the fusion protein to the IL-2Rα and the IL-2Rβ and IL-2Rγ complex are determined as described in Richert et al., *J. Mol. Biol.* 2004, 339, 1115-9.

In one embodiment, the IL-2Rγ is a human IL-2Rγ. In another embodiment, the human IL-2Rγ has an amino acid sequence of SEQ ID NO: 100.

In yet another embodiment, the N-glycosylated interleukin-2 domain in the fusion protein provided herein is an N-glycosylated polypeptide of 133 amino acids.

In yet another embodiment, the N-glycosylated interleukin-2 domain in the fusion protein provided herein comprises one, two, three, four, or more substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5.

In one embodiment, the N-glycosylated interleukin-2 domain in the fusion protein provided herein comprises an amino acid substitution at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, or T111 as set forth in an amino acid sequence of SEQ ID NO: 1, 2, 3, 4, or 5. In certain embodiments, the N-glycosylated interleukin-2 domain in the fusion protein provided herein comprises an amino acid substitution at position K35, M39, A73, or D109 as set forth in an amino acid sequence of SEQ ID NO: 1, 2, 3, 4, or 5.

In another embodiment, the N-glycosylated interleukin-2 domain in the fusion protein provided herein comprises two substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the N-glycosylated interleukin-2 domain in the fusion protein provided herein comprises two substitutions at position P34, K35, L36, T37, R38, L40, T41, F42, K43, F44, Y45, M46, P47, E61, E62, L63, P65, L66, E67, E68, V69, L70, N71, L72, Q74, Y107, D109, and/or T111 as set forth in an amino acid sequence of SEQ ID NO: 1, 2, 3, 4, or 5.

In yet another embodiment, the N-glycosylated interleukin-2 domain in the fusion protein provided herein comprises three substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the N-glycosylated interleukin-2 domain in the fusion protein provided herein comprises three substitutions at position R38, L40, F42, Y45, E61, E62, K64, P65, and/or L66 as set forth in an amino acid sequence of SEQ ID NO: 1, 2, 3, 4, or 5.

In yet another embodiment, the N-glycosylated interleukin-2 domain in the fusion protein provided herein comprises four substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the N-glycosylated interleukin-2 domain in the fusion protein provided herein comprises four substitutions at position R38, L40, F42, and Y45 as set forth in an amino acid sequence of SEQ ID NO: 1, 2, 3, 4, or 5.

In yet another embodiment, the N-glycosylated interleukin-2 domain in the fusion protein provided herein comprises one, two, three, or four substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In one embodiment, the N-glycosylated interleukin-2 domain in the fusion protein provided herein comprises one substitution selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In another embodiment, the N-glycosylated interleukin-2 domain in the fusion protein provided herein comprises two substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In yet another embodiment, the N-glycosylated interleukin-2 domain in the fusion protein provided herein comprises the substitutions of R38N and Y45N as set forth in an amino acid sequence of SEQ ID NO: 1, 2, 3, 4, or 5. In yet another embodiment, the N-glycosylated interleukin-2 domain in the fusion protein provided herein comprises three substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In still another embodiment, the N-glycosylated interleukin-2 domain in the fusion protein provided herein comprises four substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5.

In yet another embodiment, the N-glycosylated interleukin-2 domain in the fusion protein provided herein comprises one, two, three, or more N-glycosylation sites, each independently having an amino acid sequence of NXT or NXS, wherein each X is independently A, C, D, E, F, G, H, I, K, L, M, N, Q, R, S, T, V, W, or Y.

In one embodiment, the N-glycosylated interleukin-2 domain in the fusion protein provided herein comprises an N-glycosylation site having an amino acid sequence of NXT or NXS, wherein each X is independently A, C, D, E, F, G, H, I, K, L, M, N, Q, R, S, T, V, W, or Y. In another embodiment, the N-glycosylated interleukin-2 domain in the fusion protein provided herein comprises two N-glycosylation sites, each independently having an amino acid sequence of NXT or NXS, wherein each X is independently A, C, D, E, F, G, H, I, K, L, M, N, Q, R, S, T, V, W, or Y. In yet another embodiment, the N-glycosylated interleukin-2 domain in the fusion protein provided herein comprises an N-glycosylation site of NFT and an N-glycosylation site of NMT. In still another embodiment, the N-glycosylated interleukin-2 domain in the fusion protein provided herein comprises three N-glycosylation sites, each independently having an amino acid sequence of NXT or NXS, wherein each X is independently A, C, D, E, F, G, H, I, K, L, M, N, Q, R, S, T, V, W, or Y.

In one embodiment, each X is independently A, C, D, E, F, G, H, I, K, M, N, Q, R, S, T, V, W, or Y. In another embodiment, each X is independently A, C, D, G, H, K, M, N, Q, R, S, T, V, W, or Y. In yet another embodiment, each X is independently A, E, F, K, L, M, R, V, W, or Y. In still another embodiment, each X is independently F or M.

In yet another embodiment, the N-glycosylated interleukin-2 domain in the fusion protein provided herein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS.

In one embodiment, the N-glycosylated interleukin-2 domain in the fusion protein provided herein comprises an N-glycosylation site having an amino acid sequence of NAT or NAS. In another embodiment, the N-glycosylated interleukin-2 domain in the fusion protein provided herein comprises an N-glycosylation site having an amino acid sequence of NET or NES. In yet another embodiment, the N-glycosylated interleukin-2 domain in the fusion protein provided herein comprises an N-glycosylation site having an amino acid sequence of NFT or NFS. In yet another embodiment, the N-glycosylated interleukin-2 domain in the fusion protein provided herein comprises an N-glycosylation site having an amino acid sequence of NKT or NKS. In yet another embodiment, the N-glycosylated interleukin-2 domain in the fusion protein provided herein comprises an N-glycosylation site having an amino acid sequence of NLT or NLS. In yet another embodiment, the N-glycosylated interleukin-2 domain in the fusion protein provided herein comprises an N-glycosylation site having an amino acid sequence of NMT or NMS. In yet another embodiment, the N-glycosylated interleukin-2 domain in the fusion protein provided herein comprises an N-glycosylation site having an amino acid sequence of NRT or NRS. In yet another embodiment, the N-glycosylated interleukin-2 domain in the fusion protein provided herein comprises an N-glycosylation site having an amino acid sequence of NVT or NVS. In yet another embodiment, the N-glycosylated interleukin-2 domain in the fusion protein provided herein comprises an N-glycosylation site having an amino acid sequence of NWT or NWS. In still another embodiment, the N-glycosylated interleukin-2 domain in the fusion protein provided herein comprises an N-glycosylation site having an amino acid sequence of NYT or NYS.

In yet another embodiment, the N-glycosylated interleukin-2 domain in the fusion protein provided herein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS, each independently starting at position 34, 35, 37, 38, 39, 41, 42, 43, 44, 45, 61, 62, 64, 65, 66, 68, 69, 71, 72, 107, or 109 as set forth in an amino acid sequence of SEQ ID NO: 1, 2, 3, 4, or 5.

In one embodiment, the N-glycosylated interleukin-2 domain in the fusion protein provided herein comprises an N-glycosylation site having an amino acid sequence of NKT or NKS, each independently starting at position 34 or 42 as set forth in an amino acid sequence of SEQ ID NO: 1, 2, 3, 4, or 5.

In another embodiment, the N-glycosylated interleukin-2 domain in the fusion protein provided herein comprises an N-glycosylation site having an amino acid sequence of NLT or NLS, each independently starting at position 35, 39, 62, 65, 69, or 71 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NRT or NRS, each independently starting at position 37 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NMT or NMS, each independently starting at position 38 or 45 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NFT or NFS, each independently starting at position 41 or 43 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NYT or NYS, each independently starting at position 44 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NET or NES, each independently starting at position 61, 66, or 109 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site having an amino acid sequence of NAT or NAS, each independently starting at position 64, 72, or 107 as set forth in an amino acid sequence of SEQ ID NO: 1, 2, 3, 4, or 5.

In still another embodiment, the N-glycosylated interleukin-2 domain in the fusion protein provided herein comprises an N-glycosylation site having an amino acid sequence of NVT or NVS, each independently starting at position 68 as set forth in an amino acid sequence of SEQ ID NO: 1, 2, 3, 4, or 5.

In yet another embodiment, the N-glycosylated interleukin-2 domain in the fusion protein provided herein comprises an amino acid sequence of NA, NE, NK, NM, or NW.

In one embodiment, the N-glycosylated interleukin-2 domain in the fusion protein provided herein comprises an amino acid sequence of NA. In another embodiment, the N-glycosylated interleukin-2 domain in the fusion protein provided herein comprises an amino acid sequence of NE. In yet another embodiment, the N-glycosylated interleukin-2 domain in the fusion protein provided herein comprises an amino acid sequence of NK. In yet another embodiment, the N-glycosylated interleukin-2 domain in the fusion protein provided herein comprises an amino acid sequence of NM. In still another embodiment, the N-glycosylated interleukin-2 domain in the fusion protein provided herein comprises an amino acid sequence of NW.

In yet another embodiment, the N-glycosylated interleukin-2 domain in the fusion protein provided herein comprises an amino acid sequence of NA, NE, NK, NM, or NW, each independently starting at position 34, 38, 42, 45, 61, 64, 66, 72, 107, or 109 as set forth in an amino acid sequence of SEQ ID NO: 1, 2, 3, 4, or 5.

In one embodiment, the N-glycosylated interleukin-2 domain in the fusion protein provided herein comprises an amino acid sequence of NK starting at position 34 or 42 as set forth in an amino acid sequence of SEQ ID NO: 1, 2, 3, 4, or 5. In another embodiment, the N-glycosylated interleukin-2 domain in the fusion protein provided herein comprises an amino acid sequence of NM starting at position 38 or 45 as set forth in an amino acid sequence of SEQ ID NO: 1, 2, 3, 4, or 5. In yet another embodiment, the N-glycosylated interleukin-2 domain in the fusion protein provided herein comprises an amino acid sequence of NE starting at position 61, 66, or 109 as set forth in an amino acid sequence of SEQ ID NO: 1, 2, 3, 4, or 5. In still another embodiment, the N-glycosylated interleukin-2 domain in the fusion protein provided herein comprises an amino acid sequence of NA starting at position 64, 72, or 107 as set forth in an amino acid sequence of SEQ ID NO: 1, 2, 3, 4, or 5.

In yet another embodiment, the N-glycosylated interleukin-2 domain in the fusion protein provided herein comprises an N-glycosylation site that comprises an amino acid sequence of NK, NM, NE, NW, or NA.

In one embodiment, the N-glycosylated interleukin-2 domain in the fusion protein provided herein comprises an N-glycosylation site that comprises an amino acid sequence of NK. In another embodiment, the N-glycosylated interleukin-2 domain in the fusion protein provided herein comprises an N-glycosylation site that comprises an amino acid sequence of NM. In yet another embodiment, the N-glycosylated interleukin-2 domain in the fusion protein provided herein comprises an N-glycosylation site that comprises an amino acid sequence of NE. In yet another embodiment, the N-glycosylated interleukin-2 domain in the fusion protein provided herein comprises an N-glycosylation site that comprises an amino acid sequence of NW. In still another embodiment, the N-glycosylated interleukin-2 domain in the fusion protein provided herein comprises an N-glycosylation site that comprises an amino acid sequence of NA.

In yet another embodiment, the N-glycosylated interleukin-2 domain in the fusion protein provided herein comprises an N-glycosylation site that comprises an amino acid sequence of NK, NM, NE, NW, or NA, each independently starting at position 34, 38, 42, 45, 61, 64, 66, 72, 107, or 109 as set forth in an amino acid sequence of SEQ ID NO: 1, 2, 3, 4, or 5.

In one embodiment, the N-glycosylated interleukin-2 domain in the fusion protein provided herein comprises an N-glycosylation site that comprises an amino acid sequence of NK starting at position 34 or 42 as set forth in an amino acid sequence of SEQ ID NO: 1, 2, 3, 4, or 5. In another embodiment, the N-glycosylated interleukin-2 domain in the fusion protein provided herein comprises an N-glycosylation site that comprises an amino acid sequence of NM starting at position 38 or 45 as set forth in an amino acid sequence of SEQ ID NO: 1, 2, 3, 4, or 5. In yet another embodiment, the N-glycosylated interleukin-2 domain in the fusion protein provided herein comprises an N-glycosylation site that comprises an amino acid sequence of NE starting at position 61, 66, or 109 as set forth in an amino acid sequence of SEQ ID NO: 1, 2, 3, 4, or 5. In still another embodiment, the N-glycosylated interleukin-2 domain in the fusion protein provided herein comprises an N-glycosylation site that comprises an amino acid sequence of NA starting at position 64, 72, or 107 as set forth in an amino acid sequence of SEQ ID NO: 1, 2, 3, 4, or 5.

In one embodiment, the N-glycosylated interleukin-2 domain in the fusion protein provided herein comprises an amino acid substitution P34N, wherein the asparagine at position 34 is N-glycosylated. In another embodiment, the N-glycosylated interleukin-2 domain in the fusion protein provided herein comprises an amino acid substitution K35N, wherein the asparagine at position 35 is N-glycosylated. In yet another embodiment, the N-glycosylated interleukin-2 domain in the fusion protein provided herein comprises an amino acid substitution T37N, wherein the asparagine at position 37 is N-glycosylated. In yet another embodiment, the N-glycosylated interleukin-2 domain in the fusion protein provided herein comprises an amino acid substitution R38N, wherein the asparagine at position 38 is N-glycosylated. In yet another embodiment, the N-glycosylated interleukin-2 domain in the fusion protein provided herein comprises an amino acid substitution M39N, wherein the asparagine at position 39 is N-glycosylated. In yet another embodiment, the N-glycosylated interleukin-2 domain in the fusion protein provided herein comprises an amino acid substitution T41N, wherein the asparagine at position 41 is N-glycosylated. In yet another embodiment, the N-glycosylated interleukin-2 domain in the fusion protein provided herein comprises an amino acid substitution F42N, wherein the asparagine at position 42 is N-glycosylated. In yet another embodiment, the N-glycosylated interleukin-2 domain in the fusion protein provided herein comprises an amino acid substitution K43N, wherein the asparagine at position 43 is N-glycosylated. In yet another embodiment, the N-glycosylated interleukin-2 domain in the fusion protein provided herein comprises an amino acid substitution F44N, wherein the asparagine at position 44 is N-glycosylated. In yet another embodiment, the N-glycosylated interleukin-2 domain in the fusion protein provided herein comprises an amino acid substitution Y45N, wherein the asparagine at position 45 is N-glycosylated. In yet another embodiment, the N-glycosylated interleukin-2 domain in the fusion protein provided herein comprises an amino acid substitution E61N, wherein the asparagine at position 61 is N-glycosylated. In yet another embodiment, the N-glycosylated interleukin-2 domain in the fusion protein provided herein comprises an amino acid substitution E62N, wherein the asparagine at position 62 is N-glycosylated. In yet another embodiment, the N-glycosylated interleukin-2 domain in the fusion protein provided herein comprises an amino acid substitution K64N, wherein the asparagine at position 64 is N-glycosylated. In yet another embodiment, the N-glycosylated interleukin-2 domain in the fusion protein provided herein comprises an amino acid substitution P65N, wherein the asparagine at position 65 is N-glycosylated. In yet another embodiment, the N-glycosylated interleukin-2 domain in the fusion protein provided herein comprises an amino acid substitution L66N, wherein the asparagine at position 66 is N-glycosylated. In yet another embodiment, the N-glycosylated interleukin-2 domain in the fusion protein provided herein comprises an amino acid substitution E68N, wherein the asparagine at position 68 is N-glycosylated. In yet another embodiment, the N-glycosylated interleukin-2 domain in the fusion protein provided herein comprises an amino acid substitution V69N, wherein the asparagine at position 69 is N-glycosylated. In yet another embodiment, the N-glycosylated interleukin-2 domain in the fusion protein provided herein comprises an amino acid substitution A73T or A73S, wherein the asparagine at position 71 is N-glycosylated. In yet another embodiment, the N-glycosylated interleukin-2 domain in the fusion protein provided herein comprises an amino acid substitution L72N, wherein the asparagine at position 72 is N-glycosylated. In yet another embodiment, the N-glycosylated interleukin-2 domain in the fusion protein provided herein comprises an amino acid substitution Y107N, wherein the asparagine at position 107 is N-glycosylated. In still another embodiment, the N-glycosylated interleukin-2 domain in the fusion protein provided herein comprises an amino acid substitution D109N, wherein the asparagine at position 109 is N-glycosylated.

In yet another embodiment, the N-glycosylated interleukin-2 domain in the fusion protein provided herein comprises an N-glycosylation site at an interface residue between an interleukin-2 and an interleukin-2 receptor-α (IL-2Rα) chain.

In one embodiment, the interface residue is K35, T37, R38, T41, F42, K43, F44, Y45, E61, E62, K64, P65, E68, L72, or Y107 as set forth in an amino acid sequence of SEQ ID NO: 1, 2, 3, 4, or 5. In another embodiment, the interface residue is K35 as set forth in an amino acid sequence of SEQ ID NO: 1, 2, 3, 4, or 5. In yet another embodiment, the interface residue is T37 as set forth in an amino acid sequence of SEQ ID NO: 1, 2, 3, 4, or 5. In yet another embodiment, the interface residue is R38 as set forth in an amino acid sequence of SEQ ID NO: 1, 2, 3, 4, or 5. In yet another embodiment, the interface residue is T41 as set forth in an amino acid sequence of SEQ ID NO: 1, 2, 3, 4, or 5. In yet another embodiment, the interface residue is F42 as set forth in an amino acid sequence of SEQ ID NO: 1, 2, 3, 4, or 5. In yet another embodiment, the interface residue is K43 as set forth in an amino acid sequence of SEQ ID NO: 1, 2, 3, 4, or 5. In yet another embodiment, the interface residue is F44 as set forth in an amino acid sequence of SEQ ID NO: 1, 2, 3, 4, or 5. In yet another embodiment, the interface residue is Y45 as set forth in an amino acid sequence of SEQ ID NO: 1, 2, 3, 4, or 5. In yet another embodiment, the interface residue is E61 as set forth in an amino acid sequence of SEQ ID NO: 1, 2, 3, 4, or 5. In yet another embodiment, the interface residue is E62 as set forth in an amino acid sequence of SEQ ID NO: 1, 2, 3, 4, or 5. In yet another embodiment, the interface residue is K64 as set forth in an amino acid sequence of SEQ ID NO: 1, 2, 3, 4, or 5. In yet another embodiment, the interface residue is P65 as set forth in an amino acid sequence of SEQ ID NO: 1, 2, 3, 4, or 5. In yet another embodiment, the interface residue is E68 as set forth in an amino acid sequence of SEQ ID NO: 1, 2, 3, 4, or 5. In yet another embodiment, the interface residue is L72 as set forth in an amino acid sequence of SEQ ID NO: 1, 2, 3, 4, or 5. In still another embodiment, the interface residue is Y107 as set forth in an amino acid sequence of SEQ ID NO: 1, 2, 3, 4, or 5.

In one embodiment, the N-glycosylated interleukin-2 domain in the fusion protein provided herein comprises an amino acid substitution K35N, wherein the asparagine at position 35 is N-glycosylated. In another embodiment, the N-glycosylated interleukin-2 domain in the fusion protein provided herein comprises an amino acid substitution T37N, wherein the asparagine at position 37 is N-glycosylated. In yet another embodiment, the N-glycosylated interleukin-2 domain in the fusion protein provided herein comprises an amino acid substitution R38N, wherein the asparagine at position 38 is N-glycosylated. In yet another embodiment, the N-glycosylated interleukin-2 domain in the fusion protein provided herein comprises an amino acid substitution T41N, wherein the asparagine at position 41 is N-glycosylated. In yet another embodiment, the N-glycosylated interleukin-2 domain in the fusion protein provided herein comprises an amino acid substitution F42N, wherein the asparagine at position 42 is N-glycosylated. In yet another embodiment, the N-glycosylated interleukin-2 domain in the fusion protein provided herein comprises an amino acid substitution K43N, wherein the asparagine at position 43 is N-glycosylated. In yet another embodiment, the N-glycosylated interleukin-2 domain in the fusion protein provided herein comprises an amino acid substitution F44N, wherein the asparagine at position 44 is N-glycosylated. In yet another embodiment, the N-glycosylated interleukin-2 domain in the fusion protein provided herein comprises an amino acid substitution Y45N, wherein the asparagine at position 45 is N-glycosylated. In yet another embodiment, the N-glycosylated interleukin-2 domain in the fusion protein provided herein comprises an amino acid substitution E61N, wherein the asparagine at position 61 is N-glycosylated. In yet another embodiment, the N-glycosylated interleukin-2 domain in the fusion protein provided herein comprises an amino acid substitution E62N, wherein the asparagine at position 62 is N-glycosylated. In yet another embodiment, the N-glycosylated interleukin-2 domain in the fusion protein provided herein comprises an amino acid substitution K64N, wherein the asparagine at position 64 is N-glycosylated. In yet another embodiment, the N-glycosylated interleukin-2 domain in the fusion protein provided herein comprises an amino acid substitution P65N, wherein the asparagine at position 65 is N-glycosylated. In yet another embodiment, the N-glycosylated interleukin-2 domain in the fusion protein provided herein comprises an amino acid substitution E68N, wherein the asparagine at position 68 is N-glycosylated. In yet another embodiment, the N-glycosylated interleukin-2 domain in the fusion protein provided herein comprises an amino acid substitution L72N, wherein the asparagine at position 72 is N-glycosylated. In still another embodiment, the N-glycosylated interleukin-2 domain in the fusion protein provided herein comprises an amino acid substitution Y107N, wherein the asparagine at position 107 is N-glycosylated.

In still another embodiment, the N-glycosylated interleukin-2 domain in the fusion protein provided herein comprises an N-glycosylation site at position K35, T37, R38, T41, F42, K43, F44, Y45, E61, E62, K64, P65, E68, L72, or Y107 as set forth in an amino acid sequence of SEQ ID NO: 1, 2, 3, 4, or 5.

In one embodiment, the N-glycosylated interleukin-2 domain in the fusion protein provided herein comprises an N-glycosylation site at position K35 as set forth in an amino acid sequence of SEQ ID NO: 1, 2, 3, 4, or 5. In another embodiment, the N-glycosylated interleukin-2 domain in the fusion protein provided herein comprises an N-glycosylation site at position T37 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position R38 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position T41 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position F42 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position K43 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position F44 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position Y45 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position E61 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position E62 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position K64 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position P65 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position E68 as set forth in an amino acid sequence of SEQ ID NO: 1, 2, 3, 4, or 5. In yet another embodiment, the N-glycosylated interleukin-2 domain in the fusion protein provided herein comprises an N-glycosylation site at position L72 as set forth in an amino acid sequence of SEQ ID NO: 1, 2, 3, 4, or 5. In still another embodiment, the N-glycosylated interleukin-2 domain in the fusion protein provided herein comprises an N-glycosylation site at position Y107 as set forth in an amino acid sequence of SEQ ID NO: 1, 2, 3, 4, or 5.

In certain embodiments, the N-glycosylated interleukin-2 domain in the fusion protein provided herein comprises an amino acid sequence that is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 1, 2, 3, 4, or 5.

In certain embodiments, the N-glycosylated interleukin-2 domain in the fusion protein provided herein comprises an amino acid sequence that is no less than about 80% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 85% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 90% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 91% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 92% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 93% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 94% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 95% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 96% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 97% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 98% identical to an amino acid sequence of SEQ ID NO: 1, 2, 3, 4, or 5. In certain embodiments, the N-glycosylated interleukin-2 domain in the fusion protein provided herein comprises an amino acid sequence that is no less than about 99% identical to an amino acid sequence of SEQ ID NO: 1, 2, 3, 4, or 5.

In certain embodiments, the N-glycosylated interleukin-2 domain in the fusion protein provided herein is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 1, 2, 3, 4, or 5.

In certain embodiments, the N-glycosylated interleukin-2 domain in the fusion protein provided herein is no less than about 80% identical to an amino acid sequence of SEQ ID NO: 1, 2, 3, 4, or 5. In certain embodiments, the N-glycosylated interleukin-2 domain in the fusion protein provided herein is no less than about 85% identical to an amino acid sequence of SEQ ID NO: 1, 2, 3, 4, or 5. In certain embodiments, the N-glycosylated interleukin-2 domain in the fusion protein provided herein is no less than about 90% identical to an amino acid sequence of SEQ ID NO: 1, 2, 3, 4, or 5. In certain embodiments, the N-glycosylated interleukin-2 domain in the fusion protein provided herein is no less than about 91% identical to an amino acid sequence of SEQ ID NO: 1, 2, 3, 4, or 5. In certain embodiments, the N-glycosylated interleukin-2 domain in the fusion protein provided herein is no less than about 92% identical to an amino acid sequence of SEQ ID NO: 1, 2, 3, 4, or 5. In certain embodiments, the N-glycosylated interleukin-2 domain in the fusion protein provided herein is no less than about 93% identical to an amino acid sequence of SEQ ID NO: 1, 2, 3, 4, or 5. In certain embodiments, the N-glycosylated interleukin-2 domain in the fusion protein provided herein is no less than about 94% identical to an amino acid sequence of SEQ ID NO: 1, 2, 3, 4, or 5. In certain embodiments, the N-glycosylated interleukin-2 domain in the fusion protein provided herein is no less than about 95% identical to an amino acid sequence of SEQ ID NO: 1, 2, 3, 4, or 5. In certain embodiments, the N-glycosylated interleukin-2 domain in the fusion protein provided herein is no less than about 96% identical to an amino acid sequence of SEQ ID NO: 1, 2, 3, 4, or 5. In certain embodiments, the N-glycosylated interleukin-2 domain in the fusion protein provided herein is no less than about 97% identical to an amino acid sequence of SEQ ID NO: 1, 2, 3, 4, or 5. In certain embodiments, the N-glycosylated interleukin-2 domain in the fusion protein provided herein is no less than about 98% identical to an amino acid sequence of SEQ ID NO: 1, 2, 3, 4, or 5. In certain embodiments, the N-glycosylated interleukin-2 domain in the fusion protein provided herein is no less than about 99% identical to an amino acid sequence of SEQ ID NO: 1, 2, 3, 4, or 5.

In certain embodiments, the N-glycosylated interleukin-2 domain in the fusion protein provided herein comprises an amino acid substitution: K35N, M39N, A73T, A73S, or D109N, as set forth in an amino acid sequence of SEQ ID NO: 1, 2, 3, 4, or 5.

In one embodiment, the N-glycosylated interleukin-2 domain in the fusion protein provided herein comprises an amino acid substitution: K35N, as set forth in an amino acid sequence of SEQ ID NO: 1, 2, 3, 4, or 5. In another embodiment, the N-glycosylated interleukin-2 domain in the fusion protein provided herein comprises an amino acid sequence of SEQ ID NO: 10, 11, 12, or 13. In yet another embodiment, the amino acid sequence of the N-glycosylated interleukin-2 domain in the fusion protein provided herein is SEQ ID NO: 10, 11, 12, or 13.

In one embodiment, the N-glycosylated interleukin-2 domain in the fusion protein provided herein comprises an amino acid substitution: M39N, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 86 or 87. In yet another embodiment, the amino acid sequence of the N-glycosylated interleukin-2 domain in the fusion protein provided herein is SEQ ID NO: 86 or 87.

In one embodiment, the N-glycosylated interleukin-2 domain in the fusion protein provided herein comprises an amino acid substitution: A73T or A73S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 70, 71, 72, or 73. In yet another embodiment, the amino acid sequence of the N-glycosylated interleukin-2 domain in the fusion protein provided herein is SEQ ID NO: 70, 71, 72, or 73.

In one embodiment, the N-glycosylated interleukin-2 domain in the fusion protein provided herein comprises an amino acid substitution: D109N, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 82, 83, 84, or 85. In yet another embodiment, the amino acid sequence of the N-glycosylated interleukin-2 domain in the fusion protein provided herein is SEQ ID NO: 82, 83, 84, or 85.

In certain embodiments, the N-glycosylated interleukin-2 domain in the fusion protein provided herein comprises a two-amino acid substitution combination selected from: (i) P34N and L36T or L36S; (ii) K35N and T37S; (iii) T37N and M39T or M39S; (iv) R38N and L40T or L40S; (v) T41N and K43T or K43S; (vi) F42N and F44T or F44S; (vii) K43N and Y45T or Y45S; (viii) F44N and M46T or M46S; (ix) Y45N and P47T or P47S; (x) E61N and L63T or L63S; (xi) E62N and K64T or K64S; (xii) P65N and E67T or E67S; (xiii) L66N and E68T or E68S; (xiv) E68N and L70T or L70S; (xv) V69N and N71T or N71S; (xvi) L72N and Q74T or Q74S; (xvii) Y107N and D109T or D109S; and (xviii) D109N and T111S; as set forth in an amino acid sequence of SEQ ID NO: 1, 2, 3, 4, or 5.

In one embodiment, the N-glycosylated interleukin-2 domain in the fusion protein provided herein comprises two amino acid substitutions: (i) P34N and (ii) L36T or L36S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 6, 7, 8, or 9. In yet another embodiment, the amino acid sequence of the N-glycosylated interleukin-2 domain in the fusion protein provided herein is SEQ ID NO: 6, 7, 8, or 9.

In one embodiment, the N-glycosylated interleukin-2 domain in the fusion protein provided herein comprises two amino acid substitutions: K35N and T37S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 11 or 13. In yet another embodiment, the amino acid sequence of the N-glycosylated interleukin-2 domain in the fusion protein provided herein is SEQ ID NO: 11 or 13.

In one embodiment, the N-glycosylated interleukin-2 domain in the fusion protein provided herein comprises two amino acid substitutions: (i) T37N and (ii) M39T or M39S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 14, 15, 16, or 17. In yet another embodiment, the amino acid sequence of the N-glycosylated interleukin-2 domain in the fusion protein provided herein is SEQ ID NO: 14, 15, 16, or 17.

In one embodiment, the N-glycosylated interleukin-2 domain in the fusion protein provided herein comprises two amino acid substitutions: (i) R38N and (ii) L40T or L40S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 18, 19, 20, or 21. In yet another embodiment, the amino acid sequence of the N-glycosylated interleukin-2 domain in the fusion protein provided herein is SEQ ID NO: 18, 19, 20, or 21.

In one embodiment, the N-glycosylated interleukin-2 domain in the fusion protein provided herein comprises two amino acid substitutions: (i) T41N and (ii) K43T or K43S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 22, 23, 24, or 25. In yet another embodiment, the amino acid sequence of the N-glycosylated interleukin-2 domain in the fusion protein provided herein is SEQ ID NO: 22, 23, 24, or 25.

In one embodiment, the N-glycosylated interleukin-2 domain in the fusion protein provided herein comprises two amino acid substitutions: (i) F42N and (ii) F44T or F44S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 26, 27, 28, or 29. In yet another embodiment, the amino acid sequence of the N-glycosylated interleukin-2 domain in the fusion protein provided herein is SEQ ID NO: 26, 27, 28, or 29.

In one embodiment, the N-glycosylated interleukin-2 domain in the fusion protein provided herein comprises two amino acid substitutions: (i) K43N and (ii) Y45T or Y45S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 30, 31, 32, or 33. In yet another embodiment, the amino acid sequence of the N-glycosylated interleukin-2 domain in the fusion protein provided herein is SEQ ID NO: 30, 31, 32, or 33.

In one embodiment, the N-glycosylated interleukin-2 domain in the fusion protein provided herein comprises two amino acid substitutions: (i) F44N and (ii) M46T or M46S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 34, 35, 36, or 37. In yet another embodiment, the amino acid sequence of the N-glycosylated interleukin-2 domain in the fusion protein provided herein is SEQ ID NO: 34, 35, 36, or 37.

In one embodiment, the N-glycosylated interleukin-2 domain in the fusion protein provided herein comprises two amino acid substitutions: (i) Y45N and (ii) P47T or P47S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 38, 39, 40, or 41. In yet another embodiment, the amino acid sequence of the N-glycosylated interleukin-2 domain in the fusion protein provided herein is SEQ ID NO: 38, 39, 40, or 41.

In one embodiment, the N-glycosylated interleukin-2 domain in the fusion protein provided herein comprises two amino acid substitutions: (i) E61N and (ii) L63T or L63S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 42, 43, 44, or 45. In yet another embodiment, the amino acid sequence of the N-glycosylated interleukin-2 domain in the fusion protein provided herein is SEQ ID NO: 42, 43, 44, or 45.

In one embodiment, the N-glycosylated interleukin-2 domain in the fusion protein provided herein comprises two amino acid substitutions: (i) E62N and (ii) K64T or K64S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 46, 47, 48, or 49. In yet another embodiment, the amino acid sequence of the N-glycosylated interleukin-2 domain in the fusion protein provided herein is SEQ ID NO: 46, 47, 48, or 49.

In one embodiment, the N-glycosylated interleukin-2 domain in the fusion protein provided herein comprises two amino acid substitutions: (i) P65N and (ii) E67T or E67S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 54, 55, 56, or 57. In yet another embodiment, the amino acid sequence of the N-glycosylated interleukin-2 domain in the fusion protein provided herein is SEQ ID NO: 54, 55, 56, or 57.

In one embodiment, the N-glycosylated interleukin-2 domain in the fusion protein provided herein comprises two amino acid substitutions: (i) L66N and (ii) E68T or E68S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 58, 59, 60, or 61. In yet another embodiment, the amino acid sequence of the N-glycosylated interleukin-2 domain in the fusion protein provided herein is SEQ ID NO: 58, 59, 60, or 61.

In one embodiment, the N-glycosylated interleukin-2 domain in the fusion protein provided herein comprises two amino acid substitutions: (i) E68N and (ii) L70T or L70S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 62, 63, 64, or 65. In yet another embodiment, the amino acid sequence of the N-glycosylated interleukin-2 domain in the fusion protein provided herein is SEQ ID NO: 62, 63, 64, or 65.

In one embodiment, the N-glycosylated interleukin-2 domain in the fusion protein provided herein comprises two amino acid substitutions: (i) V69N and (ii) N71T or N71S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 66, 67, 68, or 69. In yet another embodiment, the amino acid sequence of the N-glycosylated interleukin-2 domain in the fusion protein provided herein is SEQ ID NO: 66, 67, 68, or 69.

In one embodiment, the N-glycosylated interleukin-2 domain in the fusion protein provided herein comprises two amino acid substitutions: (i) L72N and (ii) Q74T or Q74S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 74, 75, 76, or 77. In yet another embodiment, the amino acid sequence of the N-glycosylated interleukin-2 domain in the fusion protein provided herein is SEQ ID NO: 74, 75, 76, or 77.

In one embodiment, the N-glycosylated interleukin-2 domain in the fusion protein provided herein comprises two amino acid substitutions: (i) Y107N and (ii) D109T or D109S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 78, 79, 80, or 81. In yet another embodiment, the amino acid sequence of the N-glycosylated interleukin-2 domain in the fusion protein provided herein is SEQ ID NO: 78, 79, 80, or 81.

In one embodiment, the N-glycosylated interleukin-2 domain in the fusion protein provided herein comprises two amino acid substitutions: (i) D109N and (ii) T111S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 83 or 85. In yet another embodiment, the amino acid sequence of the N-glycosylated interleukin-2 domain in the fusion protein provided herein is SEQ ID NO: 83 or 85.

In one embodiment, the N-glycosylated interleukin-2 domain in the fusion protein provided herein comprises three amino acid substitutions: (i) R38N, (ii) L40T or L40S, and (iii) F42A, Y45A, E61A, or E62A, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 90, 91, 92, 93, 94, 95, 96, or 97. In yet another embodiment, the amino acid sequence of the N-glycosylated interleukin-2 domain in the fusion protein provided herein is SEQ ID NO: 90, 91, 92, 93, 94, 95, 96, or 97.

In another embodiment, the N-glycosylated interleukin-2 domain in the fusion protein provided herein comprises three amino acid substitutions: (i) K64N, (ii) P65A, and (iii) L66T or L66S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 50, 51, 52, or 52. In yet another embodiment, the amino acid sequence of the N-glycosylated interleukin-2 domain in the fusion protein provided herein is SEQ ID NO: 50, 51, 52, or 52.

In one embodiment, the N-glycosylated interleukin-2 domain in the fusion protein provided herein comprises four amino acid substitutions: (i) R38N, (ii) L40T or L40S, (iii) K43N, and (iv) Y45T or Y45S, as set forth in an amino acid sequence of SEQ ID NO: 1, 2, 3, 4, or 5. In another embodiment, the N-glycosylated interleukin-2 domain in the fusion protein provided herein comprises the amino acid sequence of SEQ ID NO: 88 or 89. In yet another embodiment, the amino acid sequence of the N-glycosylated interleukin-2 domain in the fusion protein provided herein is SEQ ID NO: 88 or 89.

In yet another embodiment, the N-glycosylated interleukin-2 domain in the fusion protein provided herein comprises an amino acid sequence selected from SEQ ID NO: 6 to 97.

In still another embodiment, the N-glycosylated interleukin-2 domain in the fusion protein provided herein comprises an amino acid sequence selected from SEQ ID NO: 18 to 21, 30 to 33, and 88 to 97.

In one embodiment, the N-glycosylated interleukin-2 domain in the fusion protein provided herein has one glycan. In another embodiment, the N-glycosylated interleukin-2 domain in the fusion protein provided herein has one glycan attached to the nitrogen in the side chain of an asparagine residue.

In one embodiment, the N-glycosylated interleukin-2 domain in the fusion protein provided herein has two glycans. In another embodiment, the N-glycosylated interleukin-2 domain in the fusion protein provided herein has two glycans, of which at least one glycan is attached to the nitrogen in the side chain of an asparagine residue. In yet another embodiment, the N-glycosylated interleukin-2 domain in the fusion protein provided herein has two glycans, each of which is attached to the nitrogen in the side chain of an asparagine residue.

In one embodiment, the N-glycosylated interleukin-2 domain in the fusion protein provided herein has three glycans.

In one embodiment, the glycan is an N-glycan.

In one embodiment, the N-glycan on the N-glycosylated interleukin-2 domain in the fusion protein provided herein is oligomannose-type. In another embodiment, the N-glycan on the N-glycosylated interleukin-2 domain in the fusion protein provided herein is complex-type. In another embodiment, the N-glycan on the N-glycosylated interleukin-2 domain in the fusion protein provided herein is hydride-type.

In one embodiment, the N-glycan on the N-glycosylated interleukin-2 domain in the fusion protein provided herein is biantennary complex-type. In another embodiment, the N-glycan on the N-glycosylated interleukin-2 domain in the fusion protein provided herein is triantennary complex-type. In yet another embodiment, the N-glycan on the N-glycosylated interleukin-2 domain in the fusion protein provided herein is tetraantennary complex-type.

In one embodiment, the N-glycan on the N-glycosylated interleukin-2 domain in the fusion protein provided herein is one of the glycans described in FIG. 7. Szabo et al., *J. Proteome. Res.* 2018, 17, 1559-74, the disclosure of which is incorporated herein by reference in its entirety.

In certain embodiments, the N-glycosylated interleukin-2 domain in the fusion protein provided herein further includes one or more additional substitutions, deletions, and/or insertions; and/or one or more additional post-translational modifications.

In one embodiment, the interleukin-2 domain in the fusion protein provided herein is an interleukin-2 mutein. In one embodiment, the interleukin-2 mutein comprising one, two, three, four, or more substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5.

In one embodiment, the interleukin-2 mutein comprises an amino acid substitution at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, or T111 as set forth in an amino acid sequence of SEQ ID NO: 1, 2, 3, 4, or 5. In certain embodiments, the interleukin-2 mutein comprises an amino acid substitution at position K35, M39, A73, or D109 as set forth in an amino acid sequence of SEQ ID NO: 1, 2, 3, 4, or 5.

In another embodiment, the interleukin-2 mutein comprises two substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the interleukin-2 mutein comprises two substitutions at position P34, K35, L36, T37, R38, L40, T41, F42, K43, F44, Y45, M46, P47, E61, E62, L63, P65, L66, E67, E68, V69, L70, N71, L72, Q74, Y107, D109, and/or T111 as set forth in an amino acid sequence of SEQ ID NO: 1, 2, 3, 4, or 5.

In yet another embodiment, the interleukin-2 mutein comprises three substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in an amino acid sequence of SEQ ID NO: 1, 2, 3, 4, or 5. In certain embodiments, the interleukin-2 mutein comprises three substitutions at position R38, L40, F42, Y45, E61, E62, K64, P65, and/or L66 as set forth in an amino acid sequence of SEQ ID NO: 1, 2, 3, 4, or 5.

In still another embodiment, the interleukin-2 mutein comprises four substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, or T111 as set forth in an amino acid sequence of SEQ ID NO: 1, 2, 3, 4, or 5. In certain embodiments, the interleukin-2 mutein comprises four substitutions at position R38, L40, F42, and Y45 as set forth in an amino acid sequence of SEQ ID NO: 1, 2, 3, 4, or 5.

In yet another embodiment, the interleukin-2 mutein comprises one, two, three, or four substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In one embodiment, the interleukin-2 mutein comprises one substitution selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In another embodiment, the interleukin-2 mutein comprises two substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In yet another embodiment, the interleukin-2 mutein comprises the substitutions of R38N and Y45N as set forth in an amino acid sequence of SEQ ID NO: 1, 2, 3, 4, or 5. In yet another embodiment, the interleukin-2 mutein comprises three substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5. In still another embodiment, the interleukin-2 mutein comprises four substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in an amino acid sequence of SEQ ID NO: 1, 2, 3, 4, or 5.

In yet another embodiment, the interleukin-2 mutein comprises one, two, three, or more N-glycosylation sites, each independently having an amino acid sequence of NXT or NXS, wherein each X is independently A, C, D, E, F, G, H, I, K, L, M, N, Q, R, S, T, V, W, or Y.

In one embodiment, the interleukin-2 mutein comprises an N-glycosylation site having an amino acid sequence of NXT or NXS, wherein each X is independently A, C, D, E, F, G, H, I, K, L, M, N, Q, R, S, T, V, W, or Y. In another embodiment, the interleukin-2 mutein comprises two N-glycosylation sites, each independently having an amino acid sequence of NXT or NXS, wherein each X is independently A, C, D, E, F, G, H, I, K, L, M, N, Q, R, S, T, V, W, or Y. In yet another embodiment, the interleukin-2 mutein comprises an N-glycosylation site of NFT and an N-glycosylation site of NMT. In still another embodiment, the interleukin-2 mutein comprises four N-glycosylation sites, each independently having an amino acid sequence of NXT or NXS, wherein each X is independently A, C, D, E, F, G, H, I, K, L, M, N, Q, R, S, T, V, W, or Y.

In one embodiment, each X is independently A, C, D, E, F, G, H, I, K, M, N, Q, R, S, T, V, or Y. In another embodiment, each X is independently A, C, D, G, H, K, M, N, Q, R, S, T, V, W, or Y. In yet another embodiment, each X is independently A, E, F, K, L, M, R, V, W, or Y. In still another embodiment, each X is independently F or M.

In yet another embodiment, the interleukin-2 mutein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS.

In one embodiment, the interleukin-2 mutein comprises an N-glycosylation site having an amino acid sequence of NAT or NAS. In another embodiment, the interleukin-2 mutein comprises an N-glycosylation site having an amino acid sequence of NET or NES. In yet another embodiment, the interleukin-2 mutein comprises an N-glycosylation site having an amino acid sequence of NFT or NFS. In yet another embodiment, the interleukin-2 mutein comprises an N-glycosylation site having an amino acid sequence of NKT or NKS. In yet another embodiment, the interleukin-2 mutein comprises an N-glycosylation site having an amino acid sequence of NLT or NLS. In yet another embodiment, the interleukin-2 mutein comprises an N-glycosylation site having an amino acid sequence of NMT or NMS. In yet another embodiment, the interleukin-2 mutein comprises an N-glycosylation site having an amino acid sequence of NRT or NRS. In yet another embodiment, the interleukin-2 mutein comprises an N-glycosylation site having an amino acid sequence of NVT or NVS. In yet another embodiment, the interleukin-2 mutein comprises an N-glycosylation site having an amino acid sequence of NWT or NWS. In still another embodiment, the interleukin-2 mutein comprises an N-glycosylation site having an amino acid sequence of NYT or NYS.

In yet another embodiment, the interleukin-2 mutein comprises an N-glycosylation site having an amino acid sequence of NAT, NAS, NET, NES, NFT, NFS, NKT, NKS, NLT, NLS, NMT, NMS, NRT, NRS, NVT, NVS, NWT, NWS, NYT, or NYS, each independently starting at position 34, 35, 37, 38, 39, 41, 42, 43, 44, 45, 61, 62, 64, 65, 66, 68, 69, 71, 72, 107, or 109 as set forth in an amino acid sequence of SEQ ID NO: 1, 2, 3, 4, or 5.

In one embodiment, the interleukin-2 mutein comprises an N-glycosylation site having an amino acid sequence of NKT or NKS, each independently starting at position 34 or 42 as set forth in an amino acid sequence of SEQ ID NO: 1, 2, 3, 4, or 5.

In another embodiment, the interleukin-2 mutein comprises an N-glycosylation site having an amino acid sequence of NLT or NLS, each independently starting at position 35, 39, 62, 65, 69, or 71 as set forth in an amino acid sequence of SEQ ID NO: 1, 2, 3, 4, or 5.

In yet another embodiment, the interleukin-2 mutein comprises an N-glycosylation site having an amino acid sequence of NRT or NRS, each independently starting at position 37 as set forth in an amino acid sequence of SEQ ID NO: 1, 2, 3, 4, or 5.

In yet another embodiment, the interleukin-2 mutein comprises an N-glycosylation site having an amino acid sequence of NMT or NMS, each independently starting at position 38 or 45 as set forth in an amino acid sequence of SEQ ID NO: 1, 2, 3, 4, or 5.

In yet another embodiment, the interleukin-2 mutein comprises an N-glycosylation site having an amino acid sequence of NFT or NFS, each independently starting at position 41 or 43 as set forth in an amino acid sequence of SEQ ID NO: 1, 2, 3, 4, or 5.

In yet another embodiment, the interleukin-2 mutein comprises an N-glycosylation site having an amino acid sequence of NYT or NYS, each independently starting at position 44 as set forth in an amino acid sequence of SEQ ID NO: 1, 2, 3, 4, or 5.

In yet another embodiment, the interleukin-2 mutein comprises an N-glycosylation site having an amino acid sequence of NET or NES, each independently starting at position 61, 66, or 109 as set forth in an amino acid sequence of SEQ ID NO: 1, 2, 3, 4, or 5.

In yet another embodiment, the interleukin-2 mutein comprises an N-glycosylation site having an amino acid sequence of NAT or NAS, each independently starting at position 64, 72, or 107 as set forth in an amino acid sequence of SEQ ID NO: 1, 2, 3, 4, or 5.

In still another embodiment, the interleukin-2 mutein comprises an N-glycosylation site having an amino acid sequence of NVT or NVS, each independently starting at position 68 as set forth in an amino acid sequence of SEQ ID NO: 1, 2, 3, 4, or 5.

In yet another embodiment, the interleukin-2 mutein comprises an amino acid sequence of NA, NE, NK, NM, or NW.

In one embodiment, the interleukin-2 mutein comprises an amino acid sequence of NA. In another embodiment, the interleukin-2 mutein comprises an amino acid sequence of NE. In yet another embodiment, the interleukin-2 mutein comprises an amino acid sequence of NK. In yet another embodiment, the interleukin-2 mutein comprises an amino acid sequence of NM. In still another embodiment, the interleukin-2 mutein comprises an amino acid sequence of NW.

In yet another embodiment, the interleukin-2 mutein comprises an amino acid sequence of NA, NE, NK, NM, or NW, each independently starting at position 34, 38, 42, 45, 61, 64, 66, 72, 107, or 109 as set forth in an amino acid sequence of SEQ ID NO: 1, 2, 3, 4, or 5.

In one embodiment, the interleukin-2 mutein comprises an amino acid sequence of NK starting at position 34 or 42 as set forth in an amino acid sequence of SEQ ID NO: 1, 2, 3, 4, or 5. In another embodiment, the interleukin-2 mutein comprises an amino acid sequence of NM starting at position 38 or 45 as set forth in an amino acid sequence of SEQ ID NO: 1, 2, 3, 4, or 5. In yet another embodiment, the interleukin-2 mutein comprises an amino acid sequence of NE starting at position 61, 66, or 109 as set forth in an amino acid sequence of SEQ ID NO: 1, 2, 3, 4, or 5. In still another embodiment, the interleukin-2 mutein comprises an amino acid sequence of NA starting at position 64, 72, or 107 as set forth in an amino acid sequence of SEQ ID NO: 1, 2, 3, 4, or 5.

In yet another embodiment, the interleukin-2 mutein comprises an N-glycosylation site that comprises an amino acid sequence of NK, NM, NE, NW, or NA.

In one embodiment, the interleukin-2 mutein comprises an N-glycosylation site that comprises an amino acid sequence of NK. In another embodiment, the interleukin-2 mutein comprises an N-glycosylation site that comprises an amino acid sequence of NM. In yet another embodiment, the interleukin-2 mutein comprises an N-glycosylation site that comprises an amino acid sequence of NE. In yet another embodiment, the interleukin-2 mutein comprises an N-glycosylation site that comprises an amino acid sequence of NW. In still another embodiment, the interleukin-2 mutein comprises an N-glycosylation site that comprises an amino acid sequence of NA.

In yet another embodiment, the interleukin-2 mutein comprises a N-glycosylation site that comprises an amino acid sequence of NK, NM, NE, NW, or NA, each independently starting at position 34, 38, 42, 45, 61, 64, 66, 72, 107, or 109 as set forth in an amino acid sequence of SEQ ID NO: 1, 2, 3, 4, or 5.

In one embodiment, the interleukin-2 mutein comprises an N-glycosylation site that comprises an amino acid sequence of NK starting at position 34 or 42 as set forth in an amino acid sequence of SEQ ID NO: 1, 2, 3, 4, or 5. In another embodiment, the interleukin-2 mutein comprises an N-glycosylation site that comprises an amino acid sequence of NM starting at position 38 or 45 as set forth in an amino acid sequence of SEQ ID NO: 1, 2, 3, 4, or 5. In yet another embodiment, the interleukin-2 mutein comprises an N-glycosylation site that comprises an amino acid sequence of NE starting at position 61, 66, or 109 as set forth in an amino acid sequence of SEQ ID NO: 1, 2, 3, 4, or 5. In still another embodiment, the interleukin-2 mutein comprises an N-glycosylation site that comprises an amino acid sequence of NA starting at position 64, 72, or 107 as set forth in an amino acid sequence of SEQ ID NO: 1, 2, 3, 4, or 5.

In yet another embodiment, the interleukin-2 mutein comprises an N-glycosylation site at an interface residue between an interleukin-2 and an interleukin-2 receptor-α (IL-2Rα) chain.

In one embodiment, the interface residue is K35, T37, R38, T41, F42, K43, F44, Y45, E61, E62, K64, P65, E68, L72, or Y107 as set forth in SEQ ID NO: 1, 2, 3, 4, or 5. In another embodiment, the interface residue is K35 as set forth in SEQ ID NO: 1, 2, 3, 4, or 5. In yet another embodiment, the interface residue is T37 as set forth in SEQ ID NO: 1, 2, 3, 4, or 5. In yet another embodiment, the interface residue is R38 as set forth in SEQ ID NO: 1, 2, 3, 4, or 5. In yet another embodiment, the interface residue is T41 as set forth in SEQ ID NO: 1, 2, 3, 4, or 5. In yet another embodiment, the interface residue is F42 as set forth in SEQ ID NO: 1, 2, 3, 4, or 5. In yet another embodiment, the interface residue is K43 as set forth in SEQ ID NO: 1, 2, 3, 4, or 5. In yet another embodiment, the interface residue is F44 as set forth in SEQ ID NO: 1, 2, 3, 4, or 5. In yet another embodiment, the interface residue is Y45 as set forth in SEQ ID NO: 1, 2, 3, 4, or 5. In yet another embodiment, the interface residue is E61 as set forth in SEQ ID NO: 1, 2, 3, 4, or 5. In yet another embodiment, the interface residue is E62 as set forth in SEQ ID NO: 1, 2, 3, 4, or 5. In yet another embodiment, the interface residue is K64 as set forth in SEQ ID NO: 1, 2, 3, 4, or 5. In yet another embodiment, the interface residue is P65 as set forth in SEQ ID NO: 1, 2, 3, 4, or 5. In yet another embodiment, the interface residue is E68 as set forth in SEQ ID NO: 1, 2, 3, 4, or 5. In still another embodiment, the interface residue is L72 as set forth in SEQ ID NO: 1, 2, 3, 4, or 5. In yet another embodiment, the interface residue is Y107 as set forth in SEQ ID NO: 1, 2, 3, 4, or 5.

In still another embodiment, the interleukin-2 mutein comprises an N-glycosylation site at position K35, T37, R38, T41, F42, K43, F44, Y45, E61, E62, K64, P65, E68, L72, or Y107 as set forth in an amino acid sequence of SEQ ID NO: 1, 2, 3, 4, or 5.

In one embodiment, the interleukin-2 mutein comprises an N-glycosylation site at position K35 as set forth in an amino acid sequence of SEQ ID NO: 1, 2, 3, 4, or 5. In another embodiment, the interleukin-2 mutein comprises an N-glycosylation site at position T37 as set forth in an amino acid sequence of SEQ ID NO: 1, 2, 3, 4, or 5. In yet another embodiment, the interleukin-2 mutein comprises an N-glycosylation site at position R38 as set forth in an amino acid sequence of SEQ ID NO: 1, 2, 3, 4, or 5. In yet another embodiment, the interleukin-2 mutein comprises an N-glycosylation site at position T41 as set forth in an amino acid sequence of SEQ ID NO: 1, 2, 3, 4, or 5. In yet another embodiment, the interleukin-2 mutein comprises an N-glycosylation site at position F42 as set forth in an amino acid sequence of SEQ ID NO: 1, 2, 3, 4, or 5. In yet another embodiment, the interleukin-2 mutein comprises an N-glycosylation site at position K43 as set forth in an amino acid sequence of SEQ ID NO: 1, 2, 3, 4, or 5. In yet another embodiment, the interleukin-2 mutein comprises an N-glycosylation site at position F44 as set forth in an amino acid sequence of SEQ ID NO: 1, 2, 3, 4, or 5. In yet another embodiment, the interleukin-2 mutein comprises an N-glycosylation site at position Y45 as set forth in an amino acid sequence of SEQ ID NO: 1, 2, 3, 4, or 5. In yet another embodiment, the interleukin-2 mutein comprises an N-glycosylation site at position E61 as set forth in an amino acid sequence of SEQ ID NO: 1, 2, 3, 4, or 5. In yet another embodiment, the interleukin-2 mutein comprises an N-glycosylation site at position E62 as set forth in an amino acid sequence of SEQ ID NO: 1, 2, 3, 4, or 5. In yet another embodiment, the interleukin-2 mutein comprises an N-glycosylation site at position K64 as set forth in an amino acid sequence of SEQ ID NO: 1, 2, 3, 4, or 5. In yet another embodiment, the interleukin-2 mutein comprises an N-glycosylation site at position P65 in an amino acid sequence of SEQ ID NO: 1, 2, 3, 4, or 5. In yet another embodiment, the interleukin-2 mutein comprises an N-glycosylation site at position E68 as set forth in an amino acid sequence of SEQ ID NO: 1, 2, 3, 4, or 5. In yet another embodiment, the interleukin-2 mutein comprises an N-glycosylation site at position L72 as set forth in an amino acid sequence of SEQ ID NO: 1, 2, 3, 4, or 5. In still another embodiment, the interleukin-2 mutein comprises an N-glycosylation site at position Y107 as set forth in an amino acid sequence of SEQ ID NO: 1, 2, 3, 4, or 5.

In certain embodiments, the interleukin-2 mutein comprises an amino acid sequence that is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 1, 2, 3, 4, or 5.

In certain embodiments, the interleukin-2 mutein is no less than about 80% identical to an amino acid sequence of SEQ ID NO: 1, 2, 3, 4, or 5. In certain embodiments, the interleukin-2 mutein comprises an amino acid sequence that is no less than about 85% identical to an amino acid sequence of SEQ ID NO: 1, 2, 3, 4, or 5. In certain embodiments, the interleukin-2 mutein comprises an amino acid sequence that is no less than about 90% identical to an amino acid sequence of SEQ ID NO: 1, 2, 3, 4, or 5. In certain embodiments, the interleukin-2 mutein comprises an amino acid sequence that is no less than about 91% identical to an amino acid sequence of SEQ ID NO: 1, 2, 3, 4, or 5. In certain embodiments, the interleukin-2 mutein comprises an amino acid sequence that is no less than about 92% identical to an amino acid sequence of SEQ ID NO: 1, 2, 3, 4, or 5. In certain embodiments, the interleukin-2 mutein comprises an amino acid sequence that is no less than about 93% identical to an amino acid sequence of SEQ ID NO: 1, 2, 3, 4, or 5. In certain embodiments, the interleukin-2 mutein comprises an amino acid sequence that is no less than about 94% identical to an amino acid sequence of SEQ ID NO: 1, 2, 3, 4, or 5. In certain embodiments, the interleukin-2 mutein comprises an amino acid sequence that is no less than about 95% identical to an amino acid sequence of SEQ ID NO: 1, 2, 3, 4, or 5. In certain embodiments, the interleukin-2 mutein comprises an amino acid sequence that is no less than about 96% identical to an amino acid sequence of SEQ ID NO: 1, 2, 3, 4, or 5. In certain embodiments, the interleukin-2 mutein comprises an amino acid sequence that is no less than about 97% identical to an amino acid sequence of SEQ ID NO: 1, 2, 3, 4, or 5. In certain embodiments, the interleukin-2 mutein comprises an amino acid sequence that is no less than about 98% identical to an amino acid sequence of SEQ ID NO: 1, 2, 3, 4, or 5. In certain embodiments, the interleukin-2 mutein comprises an amino acid sequence that is no less than about 99% identical to an amino acid sequence of SEQ ID NO: 1, 2, 3, 4, or 5.

In certain embodiments, the interleukin-2 mutein is no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 1, 2, 3, 4, or 5.

In certain embodiments, the interleukin-2 mutein is no less than about 80% identical to an amino acid sequence of SEQ ID NO: 1, 2, 3, 4, or 5. In certain embodiments, the interleukin-2 mutein is no less than about 85% identical to an amino acid sequence of SEQ ID NO: 1, 2, 3, 4, or 5. In certain embodiments, the interleukin-2 mutein is no less than about 90% identical to an amino acid sequence of SEQ ID NO: 1, 2, 3, 4, or 5. In certain embodiments, the interleukin-2 mutein is no less than about 91% identical to an amino acid sequence of SEQ ID NO: 1, 2, 3, 4, or 5. In certain embodiments, the interleukin-2 mutein is no less than about 92% identical to an amino acid sequence of SEQ ID NO: 1, 2, 3, 4, or 5. In certain embodiments, the interleukin-2 mutein is no less than about 93% identical to an amino acid sequence of SEQ ID NO: 1, 2, 3, 4, or 5. In certain embodiments, the interleukin-2 mutein is no less than about 94% identical to an amino acid sequence of SEQ ID NO: 1, 2, 3, 4, or 5. In certain embodiments, the interleukin-2 mutein is no less than about 95% identical to an amino acid sequence of SEQ ID NO: 1, 2, 3, 4, or 5. In certain embodiments, the interleukin-2 mutein is no less than about 96% identical to an amino acid sequence of SEQ ID NO: 1, 2, 3, 4, or 5. In certain embodiments, the interleukin-2 mutein is no less than about 97% identical to an amino acid sequence of SEQ ID NO: 1, 2, 3, 4, or 5. In certain embodiments, the interleukin-2 mutein is no less than about 98% identical to an amino acid sequence of SEQ ID NO: 1, 2, 3, 4, or 5. In certain embodiments, the interleukin-2 mutein is no less than about 99% identical to an amino acid sequence of SEQ ID NO: 1, 2, 3, 4, or 5.

In certain embodiments, the interleukin-2 mutein comprises an amino acid substitution: K35N, M39N, A73T, A73S, or D109N, as set forth in an amino acid sequence of SEQ ID NO: 1, 2, 3, 4, or 5.

In one embodiment, the interleukin-2 mutein comprises an amino acid substitution: K35N, as set forth in an amino acid sequence of SEQ ID NO: 1, 2, 3, 4, or 5. In another embodiment, the interleukin-2 mutein comprises an amino acid sequence of SEQ ID NO: 10, 11, 12, or 13. In yet another embodiment, the amino acid sequence of the interleukin-2 mutein is SEQ ID NO: 10, 11, 12, or 13.

In one embodiment, the interleukin-2 mutein comprises an amino acid substitution: M39N, as set forth in an amino acid sequence of SEQ ID NO: 1, 2, 3, 4, or 5. In another embodiment, the interleukin-2 mutein comprises the amino acid sequence of SEQ ID NO: 86 or 87. In yet another embodiment, the amino acid sequence of the interleukin-2 mutein is SEQ ID NO: 86 or 87.

In one embodiment, the interleukin-2 mutein comprises an amino acid substitution: A73T or A73S, as set forth in an amino acid sequence of SEQ ID NO: 1, 2, 3, 4, or 5. In another embodiment, the interleukin-2 mutein comprises the amino acid sequence of SEQ ID NO: 70, 71, 72, or 73. In yet another embodiment, the amino acid sequence of the interleukin-2 mutein is SEQ ID NO: 70, 71, 72, or 73.

In one embodiment, the interleukin-2 mutein comprises an amino acid substitution: D109N, as set forth in an amino acid sequence of SEQ ID NO: 1, 2, 3, 4, or 5. In another embodiment, the interleukin-2 mutein comprises the amino acid sequence of SEQ ID NO: 82, 83, 84, or 85. In yet another embodiment, the amino acid sequence of the interleukin-2 mutein is SEQ ID NO: 82, 83, 84, or 85.

In certain embodiments, the interleukin-2 mutein comprises a two-amino acid substitution combination selected from (i) P34N and L36T or L36S; (ii) K35N and T37S; (iii) T37N and M39T or M39S; (iv) R38N and L40T or L40S; (v) T41N and K43T or K43S; (vi) F42N and F44T or F44S; (vii) K43N and Y45T or Y45S; (viii) F44N and M46T or M46S; (ix) Y45N and P47T or P47S; (x) E61N and L63T or L63S; (xi) E62N and K64T or K64S; (xii) P65N and E67T or E67S; (xiii) L66N and E68T or E68S; (xiv) E68N and L70T or L70S; (xv) V69N and N71T or N71S; (xvi) L72N and Q74T or Q74S; (xvii) Y107N and D109T or D109S; or (xviii) D109N and T111S; as set forth in an amino acid sequence of SEQ ID NO: 1, 2, 3, 4, or 5.

In one embodiment, the interleukin-2 mutein comprises two amino acid substitutions: (i) P34N and (ii) L36T or L36S, as set forth in an amino acid sequence of SEQ ID NO: 1, 2, 3, 4, or 5. In another embodiment, the interleukin-2 mutein comprises the amino acid sequence of SEQ ID NO: 6, 7, 8, or 9. In yet another embodiment, the amino acid sequence of the interleukin-2 mutein is SEQ ID NO: 6, 7, 8, or 9.

In one embodiment, the interleukin-2 mutein comprises two amino acid substitutions: K35N and T37S, as set forth in an amino acid sequence of SEQ ID NO: 1, 2, 3, 4, or 5. In another embodiment, the interleukin-2 mutein comprises the amino acid sequence of SEQ ID NO: 11 or 13. In yet another embodiment, the amino acid sequence of the interleukin-2 mutein is SEQ ID NO: 11 or 13.

In one embodiment, the interleukin-2 mutein comprises two amino acid substitutions: (i) T37N and (ii) M39T or M39S, as set forth in an amino acid sequence of SEQ ID NO: 1, 2, 3, 4, or 5. In another embodiment, the interleukin-2 mutein comprises the amino acid sequence of SEQ ID NO: 14, 15, 16, or 17. In yet another embodiment, the amino acid sequence of the interleukin-2 mutein is SEQ ID NO: 14, 15, 16, or 17.

In one embodiment, the interleukin-2 mutein comprises two amino acid substitutions: (i) R38N and (ii) L40T or L40S, as set forth in an amino acid sequence of SEQ ID NO: 1, 2, 3, 4, or 5. In another embodiment, the interleukin-2 mutein comprises the amino acid sequence of SEQ ID NO: 18, 19, 20, or 21. In yet another embodiment, the amino acid sequence of the interleukin-2 mutein is SEQ ID NO: 18, 19, 20, or 21.

In one embodiment, the interleukin-2 mutein comprises two amino acid substitutions: (i) T41N and (ii) K43T or K43S, as set forth in an amino acid sequence of SEQ ID NO: 1, 2, 3, 4, or 5. In another embodiment, the interleukin-2 mutein comprises the amino acid sequence of SEQ ID NO: 22, 23, 24, or 25. In yet another embodiment, the amino acid sequence of the interleukin-2 mutein is SEQ ID NO: 22, 23, 24, or 25.

In one embodiment, the interleukin-2 mutein comprises two amino acid substitutions: (i) F42N and (ii) F44T or F44S, as set forth in an amino acid sequence of SEQ ID NO: 1, 2, 3, 4, or 5. In another embodiment, the interleukin-2 mutein comprises the amino acid sequence of SEQ ID NO: 26, 27, 28, or 29. In yet another embodiment, the amino acid sequence of the interleukin-2 mutein is SEQ ID NO: 26, 27, 28, or 29.

In one embodiment, the interleukin-2 mutein comprises two amino acid substitutions: (i) K43N and (ii) Y45T or Y45S, as set forth in an amino acid sequence of SEQ ID NO: 1, 2, 3, 4, or 5. In another embodiment, the interleukin-2 mutein comprises the amino acid sequence of SEQ ID NO: 30, 31, 32, or 33. In yet another embodiment, the amino acid sequence of the interleukin-2 mutein is SEQ ID NO: 30, 31, 32, or 33.

In one embodiment, the interleukin-2 mutein comprises two amino acid substitutions: (i) F44N and (ii) M46T or M46S, as set forth in an amino acid sequence of SEQ ID NO: 1, 2, 3, 4, or 5. In another embodiment, the interleukin-2 mutein comprises the amino acid sequence of SEQ ID NO: 34, 35, 36, or 37. In yet another embodiment, the amino acid sequence of the interleukin-2 mutein is SEQ ID NO: 34, 35, 36, or 37.

In one embodiment, the interleukin-2 mutein comprises two amino acid substitutions: (i) Y45N and (ii) P47T or P47S, as set forth in an amino acid sequence of SEQ ID NO: 1, 2, 3, 4, or 5. In another embodiment, the interleukin-2 mutein comprises the amino acid sequence of SEQ ID NO: 38, 39, 40, or 41. In yet another embodiment, the amino acid sequence of the interleukin-2 mutein is SEQ ID NO: 38, 39, 40, or 41.

In one embodiment, the interleukin-2 mutein comprises two amino acid substitutions: (i) E61N and (ii) L63T or L63S, as set forth in an amino acid sequence of SEQ ID NO: 1, 2, 3, 4, or 5. In another embodiment, the interleukin-2 mutein comprises the amino acid sequence of SEQ ID NO: 42, 43, 44, or 45. In yet another embodiment, the amino acid sequence of the interleukin-2 mutein is SEQ ID NO: 42, 43, 44, or 45.

In one embodiment, the interleukin-2 mutein comprises two amino acid substitutions: (i) E62N and (ii) K64T or K64S, as set forth in an amino acid sequence of SEQ ID NO: 1, 2, 3, 4, or 5. In another embodiment, the interleukin-2 mutein comprises the amino acid sequence of SEQ ID NO: 46, 47, 48, or 49. In yet another embodiment, the amino acid sequence of the interleukin-2 mutein is SEQ ID NO: 46, 47, 48, or 49.

In one embodiment, the interleukin-2 mutein comprises two amino acid substitutions: (i) P65N and (ii) E67T or E67S, as set forth in an amino acid sequence of SEQ ID NO: 1, 2, 3, 4, or 5. In another embodiment, the interleukin-2 mutein comprises the amino acid sequence of SEQ ID NO: 54, 55, 56, or 57. In yet another embodiment, the amino acid sequence of the interleukin-2 mutein is SEQ ID NO: 54, 55, 56, or 57.

In one embodiment, the interleukin-2 mutein comprises two amino acid substitutions: (i) L66N and (ii) E68T or E68S, as set forth in an amino acid sequence of SEQ ID NO: 1, 2, 3, 4, or 5. In another embodiment, the interleukin-2 mutein comprises the amino acid sequence of SEQ ID NO: 58, 59, 60, or 61. In yet another embodiment, the amino acid sequence of the interleukin-2 mutein is SEQ ID NO: 58, 59, 60, or 61.

In one embodiment, the interleukin-2 mutein comprises two amino acid substitutions: (i) E68N and (ii) L70T or L70S, as set forth in an amino acid sequence of SEQ ID NO: 1, 2, 3, 4, or 5. In another embodiment, the interleukin-2 mutein comprises the amino acid sequence of SEQ ID NO: 62, 63, 64, or 65. In yet another embodiment, the amino acid sequence of the interleukin-2 mutein is SEQ ID NO: 62, 63, 64, or 65.

In one embodiment, the interleukin-2 mutein comprises two amino acid substitutions: (i) V69N and (ii) N71T or N71S, as set forth in an amino acid sequence of SEQ ID NO: 1, 2, 3, 4, or 5. In another embodiment, the interleukin-2 mutein comprises the amino acid sequence of SEQ ID NO: 66, 67, 68, or 69. In yet another embodiment, the amino acid sequence of the interleukin-2 mutein is SEQ ID NO: 66, 67, 68, or 69.

In one embodiment, the interleukin-2 mutein comprises two amino acid substitutions: (i) L72N and (ii) Q74T or Q74S, as set forth in an amino acid sequence of SEQ ID NO: 1, 2, 3, 4, or 5. In another embodiment, the interleukin-2 mutein comprises the amino acid sequence of SEQ ID NO: 74, 75, 76, or 77. In yet another embodiment, the amino acid sequence of the interleukin-2 mutein is SEQ ID NO: 74, 75, 76, or 77.

In one embodiment, the interleukin-2 mutein comprises two amino acid substitutions: (i) Y107N and (ii) D109T or D109S, as set forth in an amino acid sequence of SEQ ID NO: 1, 2, 3, 4, or 5. In another embodiment, the interleukin-2 mutein comprises the amino acid sequence of SEQ ID NO: 78, 79, 80, or 81. In yet another embodiment, the amino acid sequence of the interleukin-2 mutein is SEQ ID NO: 78, 79, 80, or 81.

In one embodiment, the interleukin-2 mutein comprises two amino acid substitutions: (i) D109N and (ii) T111S, as set forth in an amino acid sequence of SEQ ID NO: 1, 2, 3, 4, or 5. In another embodiment, the interleukin-2 mutein comprises the amino acid sequence of SEQ ID NO: 83 or 85. In yet another embodiment, the amino acid sequence of the interleukin-2 mutein is SEQ ID NO: 83 or 85.

In one embodiment, the interleukin-2 mutein comprises three amino acid substitutions: (i) R38N, (ii) L40T or L40S, and (iii) F42A, Y45A, E61A, or E62A, as set forth in an amino acid sequence of SEQ ID NO: 1, 2, 3, 4, or 5. In another embodiment, the interleukin-2 mutein comprises the amino acid sequence of SEQ ID NO: 90, 91, 92, 93, 94, 95, 96, or 97. In yet another embodiment, the amino acid sequence of the interleukin-2 mutein is SEQ ID NO: 90, 91, 92, 93, 94, 95, 96, or 97.

In one embodiment, the interleukin-2 mutein comprises three amino acid substitutions: (i) K64N, (ii) P65A, and (iii) L66T or L66S, as set forth in an amino acid sequence of SEQ ID NO: 1, 2, 3, 4, or 5. In another embodiment, the interleukin-2 mutein comprises the amino acid sequence of SEQ ID NO: 50, 51, 52, or 52. In yet another embodiment, the amino acid sequence of the interleukin-2 mutein is SEQ ID NO: 50, 51, 52, or 52.

In one embodiment, the interleukin-2 mutein comprises four amino acid substitutions: (i) R38N, (ii) L40T, (iii) K43N, or (iv) Y45T or Y45S, as set forth in an amino acid sequence of SEQ ID NO: 1, 2, 3, 4, or 5. In another embodiment, the interleukin-2 mutein comprises the amino acid sequence of SEQ ID NO: 88 or 89. In yet another embodiment, the amino acid sequence of the interleukin-2 mutein is SEQ ID NO: 88 or 89.

In yet another embodiment, the interleukin-2 mutein comprises an amino acid sequence selected from SEQ ID NO: 6 to 97.

In still another embodiment, the interleukin-2 mutein comprises an amino acid sequence selected from SEQ ID NO: 18 to 21, 30 to 33, and 88 to 97.

In certain embodiments, the interleukin-2 mutein further includes one or more additional substitutions, deletions, and/or insertions; and/or one or more additional post-translational modifications.

In one embodiment, the interleukin-21 domain in the fusion protein provided herein is a wide-type interleukin-21 domain. In another embodiment, the interleukin-21 domain in the fusion protein provided herein is a wild-type human interleukin-21 domain. In yet another embodiment, the interleukin-21 domain in the fusion protein provided herein is an interleukin-21 variant. In still another embodiment, the interleukin-21 domain in the fusion protein provided herein is an interleukin-21 mutein.

In certain embodiments, the interleukin-21 domain in the fusion protein provided herein comprises an amino acid sequence that is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 156.

In certain embodiments, the interleukin-21 domain in the fusion protein provided herein comprises an amino acid sequence that is no less than about 70% identical to an amino acid sequence of SEQ ID NO: 156. In certain embodiments, the interleukin-21 domain in the fusion protein provided herein comprises an amino acid sequence that is no less than about 75% identical to an amino acid sequence of SEQ ID NO: 156. In certain embodiments, the interleukin-21 domain in the fusion protein provided herein comprises an amino acid sequence that is no less than about 80% identical to an amino acid sequence of SEQ ID NO: 156. In certain embodiments, the interleukin-21 domain in the fusion protein provided herein comprises an amino acid sequence that is no less than about 85% identical to an amino acid sequence of SEQ ID NO: 156. In certain embodiments, the interleukin-21 domain in the fusion protein provided herein comprises an amino acid sequence that is no less than about 90% identical to an amino acid sequence of SEQ ID NO: 156. In certain embodiments, the interleukin-21 domain in the fusion protein provided herein comprises an amino acid sequence that is no less than about 91% identical to an amino acid sequence of SEQ ID NO: 156. In certain embodiments, the interleukin-21 domain in the fusion protein provided herein comprises an amino acid sequence that is no less than about 92% identical to an amino acid sequence of SEQ ID NO: 156. In certain embodiments, the interleukin-21 domain in the fusion protein provided herein comprises an amino acid sequence that is no less than about 93% identical to an amino acid sequence of SEQ ID NO: 156. In certain embodiments, the interleukin-21 domain in the fusion protein provided herein comprises an amino acid sequence that is no less than about 94% identical to an amino acid sequence of SEQ ID NO: 156. In certain embodiments, the interleukin-21 domain in the fusion protein provided herein comprises an amino acid sequence that is no less than about 95% identical to an amino acid sequence of SEQ ID NO: 156. In certain embodiments, the interleukin-21 domain in the fusion protein provided herein comprises an amino acid sequence that is no less than about 96% identical to an amino acid sequence of SEQ ID NO: 156. In certain embodiments, the interleukin-21 domain in the fusion protein provided herein comprises an amino acid sequence that is no less than about 97% identical to an amino acid sequence of SEQ ID NO: 156. In certain embodiments, the interleukin-21 domain in the fusion protein provided herein comprises an amino acid sequence that is no less than about 98% identical to an amino acid sequence of SEQ ID NO: 156. In certain embodiments, the interleukin-21 domain in the fusion protein provided herein comprises an amino acid sequence that is no less than about 99% identical to an amino acid sequence of SEQ ID NO: 156.

In certain embodiments, the interleukin-21 domain in the fusion protein provided herein is no less than about 70%, no less than about 75%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, or no less than about 99% identical to an amino acid sequence of SEQ ID NO: 156.

In certain embodiments, the interleukin-21 domain in the fusion protein provided herein is no less than about 70% identical to an amino acid sequence of SEQ ID NO: 156. In certain embodiments, the interleukin-21 domain in the fusion protein provided herein is no less than about 75% identical to an amino acid sequence of SEQ ID NO: 156. In certain embodiments, the interleukin-21 domain in the fusion protein provided herein is no less than about 80% identical to an amino acid sequence of SEQ ID NO: 156. In certain embodiments, the interleukin-21 domain in the fusion protein provided herein is no less than about 85% identical to an amino acid sequence of SEQ ID NO: 156. In certain embodiments, the interleukin-21 domain in the fusion protein provided herein is no less than about 90% identical to an amino acid sequence of SEQ ID NO: 156. In certain embodiments, the interleukin-21 domain in the fusion protein provided herein is no less than about 91% identical to an amino acid sequence of SEQ ID NO: 156. In certain embodiments, the interleukin-21 domain in the fusion protein provided herein is no less than about 92% identical to an amino acid sequence of SEQ ID NO: 156. In certain embodiments, the interleukin-21 domain in the fusion protein provided herein is no less than about 93% identical to an amino acid sequence of SEQ ID NO: 156. In certain embodiments, the interleukin-21 domain in the fusion protein provided herein is no less than about 94% identical to an amino acid sequence of SEQ ID NO: 156. In certain embodiments, the interleukin-21 domain in the fusion protein provided herein is no less than about 95% identical to an amino acid sequence of SEQ ID NO: 156. In certain embodiments, the interleukin-21 domain in the fusion protein provided herein is no less than about 96% identical to an amino acid sequence of SEQ ID NO: 156. In certain embodiments, the interleukin-21 domain in the fusion protein provided herein is no less than about 97% identical to an amino acid sequence of SEQ ID NO: 156. In certain embodiments, the interleukin-21 domain in the fusion protein provided herein is no less than about 98% identical to an amino acid sequence of SEQ ID NO: 156. In certain embodiments, the interleukin-21 domain in the fusion protein provided herein is no less than about 99% identical to an amino acid sequence of SEQ ID NO: 156.

In certain embodiments, the interleukin-21 variant lacks about 1 to about 10 amino acids between S124 and S133 as set forth in an amino acid sequence of SEQ ID NO: 156. In one embodiment, the interleukin-21 variant lacks one amino acid between S124 and S133 as set forth in an amino acid sequence of SEQ ID NO: 156. In another embodiment, the interleukin-21 variant lacks two amino acids between S124 and S133 as set forth in an amino acid sequence of SEQ ID NO: 156. In yet another embodiment, the interleukin-21 variant lacks three amino acids between S124 and S133 as set forth in an amino acid sequence of SEQ ID NO: 156. In yet another embodiment, the interleukin-21 variant lacks four amino acids between S124 and S133 as set forth in an amino acid sequence of SEQ ID NO: 156. In yet another embodiment, the interleukin-21 variant lacks five amino acids between S124 and S133 as set forth in an amino acid sequence of SEQ ID NO: 156. In yet another embodiment, the interleukin-21 variant lacks six amino acids between S124 and S133 as set forth in an amino acid sequence of SEQ ID NO: 156. In yet another embodiment, the interleukin-21 variant lacks seven amino acids between S124 and S133 as set forth in an amino acid sequence of SEQ ID NO: 156. In yet another embodiment, the interleukin-21 variant lacks eight amino acids between S124 and S133 as set forth in an amino acid sequence of SEQ ID NO: 156. In yet another embodiment, the interleukin-21 variant lacks nine amino acids between S124 and S133 as set forth in an amino acid sequence of SEQ ID NO: 156. In still another embodiment, the interleukin-21 variant lacks ten amino acids between S124 and S133 as set forth in an amino acid sequence of SEQ ID NO: 156.

In one embodiment, the interleukin-21 domain in the fusion protein provided herein has an amino acid sequence of SEQ ID NO: 156, 157, or 158. In another embodiment, the interleukin-21 domain in the fusion protein provided herein has an amino acid sequence of SEQ ID NO: 156. In yet another embodiment, the interleukin-21 domain in the fusion protein provided herein has an amino acid sequence of SEQ ID NO: 157. In yet another embodiment, the interleukin-21 domain in the fusion protein provided herein has an amino acid sequence of SEQ ID NO: 158.

In certain embodiments, the interleukin-21 domain in the fusion protein provided herein further includes one or more additional substitutions, deletions, and/or insertions; and/or one or more additional post-translational modifications.

In certain embodiments, the fusion protein has a dissociation constant to IL-21Rα ranging from about 1 pM to about 100 nM, from about 2 pM to about 10 nM, from about 5 pM to about 2 nM, or from about 10 pM to about 0.5 nM. In certain embodiments, the fusion protein has a dissociation constant to IL-21Rα ranging from about 1 pM to about 100 nM. In certain embodiments, the fusion protein has a dissociation constant to IL-21Rα ranging from about 2 pM to about 10 nM. In certain embodiments, the fusion protein has a dissociation constant to IL-21Rα ranging from about 5 pM to about 2 nM. In certain embodiments, the fusion protein has a dissociation constant to IL-21Rα ranging from about 10 pM to about 0.5 nM.

In one embodiment, each peptide linker in the fusion protein provided herein independently comprises a peptide linker having an amino acid sequence of GSG or one of SEQ ID NOs: 124 to 155. In another embodiment, each peptide linker in the fusion protein provided herein is independently a peptide linker having an amino acid sequence of GSG or one of SEQ ID NOs: 124 to 155.

In one embodiment, each peptide linker in the fusion protein provided herein independently comprises a GSG linker having an amino acid sequence of GSG or SEQ ID NO: 124, 125, or 126. In another embodiment, each peptide linker in the fusion protein provided herein is independently a GSG linker having an amino acid sequence of GSG or SEQ ID NO: 124, 125, or 126. In yet another embodiment, each peptide linker in the fusion protein provided herein independently comprises a G3S linker having an amino acid sequence of SEQ ID NO: 127, 128, 129, or 130. In yet another embodiment, each peptide linker in the fusion protein provided herein is independently a G3S linker having an amino acid sequence of SEQ ID NO: 127, 128, 129, or 130. In yet another embodiment, each peptide linker in the fusion protein provided herein independently comprises a G4S linker having an amino acid sequence of SEQ ID NO: 131, 132, 133, or 134. In yet another embodiment, each peptide linker in the fusion protein provided herein is independently a G4S linker having an amino acid sequence of SEQ ID NO: 131, 132, 133, or 134. In yet another embodiment, each peptide linker in the fusion protein provided herein independently comprises an SGSG linker having an amino acid sequence of SEQ ID NO: 135, 136, 137, or 138. In yet another embodiment, each peptide linker in the fusion protein provided herein is independently an SGSG linker having an amino acid sequence of SEQ ID NO: 135, 136, 137, or 138. In yet another embodiment, each peptide linker in the fusion protein provided herein independently comprises an SG3S linker having an amino acid sequence of SEQ ID NO: 139, 140, 141, or 142. In yet another embodiment, each peptide linker in the fusion protein provided herein is independently an SG3S linker having an amino acid sequence of SEQ ID NO: 139, 140, 141, or 142. In yet another embodiment, each peptide linker in the fusion protein provided herein independently comprises an SG4S linker having an amino acid sequence of SEQ ID NO: 143, 144, 145, or 146. In yet another embodiment, each peptide linker in the fusion protein provided herein is independently an SG4S linker having an amino acid sequence of SEQ ID NO: 143, 144, 145, or 146. In yet another embodiment, each peptide linker in the fusion protein provided herein independently comprises an EAAAK linker having an amino acid sequence of SEQ ID NO: 147, 148, 149, or 150. In yet another embodiment, each peptide linker in the fusion protein provided herein is independently an EAAAK linker having an amino acid sequence of SEQ ID NO: 147, 148, 149, or 150. In yet another embodiment, each peptide linker in the fusion protein provided herein independently comprises a PAPAP linker having an amino acid sequence of SEQ ID NO: 151, 152, 153, or 154. In yet another embodiment, each peptide linker in the fusion protein provided herein is independently a PAPAP linker having an amino acid sequence of SEQ ID NO: 151, 152, 153, or 154. In yet another embodiment, each peptide linker in the fusion protein provided herein independently comprises a linker having an amino acid sequence of SEQ ID NO: 155. In yet another embodiment, each peptide linker in the fusion protein provided herein is independently comprises a linker having an amino acid sequence of SEQ ID NO: 155.

In one embodiment, the first peptide linker in the fusion protein provided herein independently comprises a peptide linker having an amino acid sequence of GSG or one of SEQ ID NOs: 124 to 155. In another embodiment, the first peptide linker in the fusion protein provided herein is independently a peptide linker having an amino acid sequence of GSG or one of SEQ ID NOs: 124 to 155.

In one embodiment, the first peptide linker in the fusion protein provided herein independently comprises a GSG linker having an amino acid sequence of GSG or SEQ ID NO: 124, 125, or 126. In another embodiment, the first peptide linker in the fusion protein provided herein is independently a GSG linker having an amino acid sequence of GSG or SEQ ID NO: 124, 125, or 126. In yet another embodiment, the first peptide linker in the fusion protein provided herein independently comprises a G3S linker having an amino acid sequence of SEQ ID NO: 127, 128, 129, or 130. In yet another embodiment, the first peptide linker in the fusion protein provided herein is independently a G3S linker having an amino acid sequence of SEQ ID NO: 127, 128, 129, or 130. In yet another embodiment, the first peptide linker in the fusion protein provided herein independently comprises a G4S linker having an amino acid sequence of SEQ ID NO: 131, 132, 133, or 134. In yet another embodiment, the first peptide linker in the fusion protein provided herein is independently a G4S linker having an amino acid sequence of SEQ ID NO: 131, 132, 133, or 134. In yet another embodiment, the first peptide linker in the fusion protein provided herein independently comprises an SGSG linker having an amino acid sequence of SEQ ID NO: 135, 136, 137, or 138. In yet another embodiment, the first peptide linker in the fusion protein provided herein is independently an SGSG linker having an amino acid sequence of SEQ ID NO: 135, 136, 137, or 138. In yet another embodiment, the first peptide linker in the fusion protein provided herein independently comprises an SG3S linker having an amino acid sequence of SEQ ID NO: 139, 140, 141, or 142. In yet another embodiment, the first peptide linker in the fusion protein provided herein is independently an SG3S linker having an amino acid sequence of SEQ ID NO: 139, 140, 141, or 142. In yet another embodiment, the first peptide linker in the fusion protein provided herein independently comprises an SG4S linker having an amino acid sequence of SEQ ID NO: 143, 144, 145, or 146. In yet another embodiment, the first peptide linker in the fusion protein provided herein is independently an SG4S linker having an amino acid sequence of SEQ ID NO: 143, 144, 145, or 146. In yet another embodiment, the first peptide linker in the fusion protein provided herein independently comprises an EAAAK linker having an amino acid sequence of SEQ ID NO: 147, 148, 149, or 150. In yet another embodiment, the first peptide linker in the fusion protein provided herein is independently an EAAAK linker having an amino acid sequence of SEQ ID NO: 147, 148, 149, or 150. In yet another embodiment, the first peptide linker in the fusion protein provided herein independently comprises a PAPAP linker having an amino acid sequence of SEQ ID NO: 151, 152, 153, or 154. In yet another embodiment, the first peptide linker in the fusion protein provided herein is independently a PAPAP linker having an amino acid sequence of SEQ ID NO: 151, 152, 153, or 154. In yet another embodiment, the first peptide linker in the fusion protein provided herein independently comprises a linker having an amino acid sequence of SEQ ID NO: 155. In yet another embodiment, the first peptide linker in the fusion protein provided herein is independently comprises a linker having an amino acid sequence of SEQ ID NO: 155.

In one embodiment, the second peptide linker in the fusion protein provided herein independently comprises a peptide linker having an amino acid sequence of GSG or one of SEQ ID NOs: 124 to 155. In another embodiment, the second peptide linker in the fusion protein provided herein is independently a peptide linker having an amino acid sequence of GSG or one of SEQ ID NOs: 124 to 155.

In one embodiment, the second peptide linker in the fusion protein provided herein independently comprises a GSG linker having an amino acid sequence of GSG or SEQ ID NO: 124, 125, or 126. In another embodiment, the second peptide linker in the fusion protein provided herein is independently a GSG linker having an amino acid sequence of GSG or SEQ ID NO: 124, 125, or 126. In yet another embodiment, the second peptide linker in the fusion protein provided herein independently comprises a G3S linker having an amino acid sequence of SEQ ID NO: 127, 128, 129, or 130. In yet another embodiment, the second peptide linker in the fusion protein provided herein is independently a G3S linker having an amino acid sequence of SEQ ID NO: 127, 128, 129, or 130. In yet another embodiment, the second peptide linker in the fusion protein provided herein independently comprises a G4S linker having an amino acid sequence of SEQ ID NO: 131, 132, 133, or 134. In yet another embodiment, the second peptide linker in the fusion protein provided herein is independently a G4S linker having an amino acid sequence of SEQ ID NO: 131, 132, 133, or 134. In yet another embodiment, the second peptide linker in the fusion protein provided herein independently comprises an SGSG linker having an amino acid sequence of SEQ ID NO: 135, 136, 137, or 138. In yet another embodiment, the second peptide linker in the fusion protein provided herein is independently an SGSG linker having an amino acid sequence of SEQ ID NO: 135, 136, 137, or 138. In yet another embodiment, the second peptide linker in the fusion protein provided herein independently comprises an SG3S linker having an amino acid sequence of SEQ ID NO: 139, 140, 141, or 142. In yet another embodiment, the second peptide linker in the fusion protein provided herein is independently an SG3S linker having an amino acid sequence of SEQ ID NO: 139, 140, 141, or 142. In yet another embodiment, the second peptide linker in the fusion protein provided herein independently comprises an SG4S linker having an amino acid sequence of SEQ ID NO: 143, 144, 145, or 146. In yet another embodiment, the second peptide linker in the fusion protein provided herein is independently an SG4S linker having an amino acid sequence of SEQ ID NO: 143, 144, 145, or 146. In yet another embodiment, the second peptide linker in the fusion protein provided herein independently comprises an EAAAK linker having an amino acid sequence of SEQ ID NO: 147, 148, 149, or 150. In yet another embodiment, the second peptide linker in the fusion protein provided herein is independently an EAAAK linker having an amino acid sequence of SEQ ID NO: 147, 148, 149, or 150. In yet another embodiment, the second peptide linker in the fusion protein provided herein independently comprises a PAPAP linker having an amino acid sequence of SEQ ID NO: 151, 152, 153, or 154. In yet another embodiment, the second peptide linker in the fusion protein provided herein is independently a PAPAP linker having an amino acid sequence of SEQ ID NO: 151, 152, 153, or 154. In yet another embodiment, the second peptide linker in the fusion protein provided herein independently comprises a linker having an amino acid sequence of SEQ ID NO: 155. In yet another embodiment, the second peptide linker in the fusion protein provided herein is independently comprises a linker having an amino acid sequence of SEQ ID NO: 155.

In one embodiment, the third peptide linker in the fusion protein provided herein independently comprises a peptide linker having an amino acid sequence of GSG or one of SEQ ID NOs: 124 to 155. In another embodiment, the third peptide linker in the fusion protein provided herein is independently a peptide linker having an amino acid sequence of GSG or one of SEQ ID NOs: 124 to 155.

In one embodiment, the third peptide linker in the fusion protein provided herein independently comprises a GSG linker having an amino acid sequence of GSG or SEQ ID NO: 124, 125, or 126. In another embodiment, the third peptide linker in the fusion protein provided herein is independently a GSG linker having an amino acid sequence of GSG or SEQ ID NO: 124, 125, or 126. In yet another embodiment, the third peptide linker in the fusion protein provided herein independently comprises a G3S linker having an amino acid sequence of SEQ ID NO: 127, 128, 129, or 130. In yet another embodiment, the third peptide linker in the fusion protein provided herein is independently a G3S linker having an amino acid sequence of SEQ ID NO: 127, 128, 129, or 130. In yet another embodiment, the third peptide linker in the fusion protein provided herein independently comprises a G4S linker having an amino acid sequence of SEQ ID NO: 131, 132, 133, or 134. In yet another embodiment, the third peptide linker in the fusion protein provided herein is independently a G4S linker having an amino acid sequence of SEQ ID NO: 131, 132, 133, or 134. In yet another embodiment, the third peptide linker in the fusion protein provided herein independently comprises an SGSG linker having an amino acid sequence of SEQ ID NO: 135, 136, 137, or 138. In yet another embodiment, the third peptide linker in the fusion protein provided herein is independently an SGSG linker having an amino acid sequence of SEQ ID NO: 135, 136, 137, or 138. In yet another embodiment, the third peptide linker in the fusion protein provided herein independently comprises an SG3S linker having an amino acid sequence of SEQ ID NO: 139, 140, 141, or 142. In yet another embodiment, the third peptide linker in the fusion protein provided herein is independently an SG3S linker having an amino acid sequence of SEQ ID NO: 139, 140, 141, or 142. In yet another embodiment, the third peptide linker in the fusion protein provided herein independently comprises an SG4S linker having an amino acid sequence of SEQ ID NO: 143, 144, 145, or 146. In yet another embodiment, the third peptide linker in the fusion protein provided herein is independently an SG4S linker having an amino acid sequence of SEQ ID NO: 143, 144, 145, or 146. In yet another embodiment, the third peptide linker in the fusion protein provided herein independently comprises an EAAAK linker having an amino acid sequence of SEQ ID NO: 147, 148, 149, or 150. In yet another embodiment, the third peptide linker in the fusion protein provided herein is independently an EAAAK linker having an amino acid sequence of SEQ ID NO: 147, 148, 149, or 150. In yet another embodiment, the third peptide linker in the fusion protein provided herein independently comprises a PAPAP linker having an amino acid sequence of SEQ ID NO: 151, 152, 153, or 154. In yet another embodiment, the third peptide linker in the fusion protein provided herein is independently a PAPAP linker having an amino acid sequence of SEQ ID NO: 151, 152, 153, or 154. In yet another embodiment, the third peptide linker in the fusion protein provided herein independently comprises a linker having an amino acid sequence of SEQ ID NO: 155. In yet another embodiment, the third peptide linker in the fusion protein provided herein is independently comprises a linker having an amino acid sequence of SEQ ID NO: 155.

In one embodiment, the fourth peptide linker in the fusion protein provided herein independently comprises a peptide linker having an amino acid sequence of GSG or one of SEQ ID NOs: 124 to 155. In another embodiment, the fourth peptide linker in the fusion protein provided herein is independently a peptide linker having an amino acid sequence of GSG or one of SEQ ID NOs: 124 to 155.

In one embodiment, the fourth peptide linker in the fusion protein provided herein independently comprises a GSG linker having an amino acid sequence of GSG or SEQ ID NO: 124, 125, or 126. In another embodiment, the fourth peptide linker in the fusion protein provided herein is independently a GSG linker having an amino acid sequence of GSG or SEQ ID NO: 124, 125, or 126. In yet another embodiment, the fourth peptide linker in the fusion protein provided herein independently comprises a G3S linker having an amino acid sequence of SEQ ID NO: 127, 128, 129, or 130. In yet another embodiment, the fourth peptide linker in the fusion protein provided herein is independently a G3S linker having an amino acid sequence of SEQ ID NO: 127, 128, 129, or 130. In yet another embodiment, the fourth peptide linker in the fusion protein provided herein independently comprises a G4S linker having an amino acid sequence of SEQ ID NO: 131, 132, 133, or 134. In yet another embodiment, the fourth peptide linker in the fusion protein provided herein is independently a G4S linker having an amino acid sequence of SEQ ID NO: 131, 132, 133, or 134. In yet another embodiment, the fourth peptide linker in the fusion protein provided herein independently comprises an SGSG linker having an amino acid sequence of SEQ ID NO: 135, 136, 137, or 138. In yet another embodiment, the fourth peptide linker in the fusion protein provided herein is independently an SGSG linker having an amino acid sequence of SEQ ID NO: 135, 136, 137, or 138. In yet another embodiment, the fourth peptide linker in the fusion protein provided herein independently comprises an SG3S linker having an amino acid sequence of SEQ ID NO: 139, 140, 141, or 142. In yet another embodiment, the fourth peptide linker in the fusion protein provided herein is independently an SG3S linker having an amino acid sequence of SEQ ID NO: 139, 140, 141, or 142. In yet another embodiment, the fourth peptide linker in the fusion protein provided herein independently comprises an SG4S linker having an amino acid sequence of SEQ ID NO: 143, 144, 145, or 146. In yet another embodiment, the fourth peptide linker in the fusion protein provided herein is independently an SG4S linker having an amino acid sequence of SEQ ID NO: 143, 144, 145, or 146. In yet another embodiment, the fourth peptide linker in the fusion protein provided herein independently comprises an EAAAK linker having an amino acid sequence of SEQ ID NO: 147, 148, 149, or 150. In yet another embodiment, the fourth peptide linker in the fusion protein provided herein is independently an EAAAK linker having an amino acid sequence of SEQ ID NO: 147, 148, 149, or 150. In yet another embodiment, the fourth peptide linker in the fusion protein provided herein independently comprises a PAPAP linker having an amino acid sequence of SEQ ID NO: 151, 152, 153, or 154. In yet another embodiment, the fourth peptide linker in the fusion protein provided herein is independently a PAPAP linker having an amino acid sequence of SEQ ID NO: 151, 152, 153, or 154. In yet another embodiment, the fourth peptide linker in the fusion protein provided herein independently comprises a linker having an amino acid sequence of SEQ ID NO: 155. In yet another embodiment, the fourth peptide linker in the fusion protein provided herein is independently comprises a linker having an amino acid sequence of SEQ ID NO: 155.

In one embodiment, provided herein is a fusion protein comprising one interleukin-2 domain having an amino acid sequence of any one of SEQ ID NOs: 1 to 97; one interleukin-21 domain having an amino acid sequence of any one of SEQ ID NOs: 156 to 158; one $V_HH$ single domain antibody having an amino acid sequence of SEQ ID NOs: 108 or 115; and optionally one or two peptide linkers, each independently having an amino acid sequence of GSG or any one of SEQ ID NOs: 124 to 155.

In another embodiment, provided herein is a fusion protein comprising one interleukin-2 domain having an amino acid sequence of SEQ ID NO: 2 or 8; one interleukin-21 domain having an amino acid sequence of SEQ ID NO: 156 or 157; one $V_HH$ single domain antibody having an amino acid sequence of SEQ ID NO: 108 or 115; and optionally one or two peptide linkers, each independently having an amino acid sequence of SEQ ID NO: 126 or 133.

In yet another embodiment, provided herein is a fusion protein comprising one interleukin-2 domain having an amino acid sequence of any one of SEQ ID NOs: 1 to 97; one interleukin-21 domain having an amino acid sequence of any one of SEQ ID NOs: 156 to 158; one $V_HH$ single domain antibody having an amino acid sequence of SEQ ID NOs: 108 or 115; and one peptide linker having an amino acid sequence of GSG or any one of SEQ ID NOs: 124 to 155; wherein the C-terminus of the interleukin-2 domain is connected to the N-terminus of the peptide linker, the C-terminus of the peptide linker is connected to the N-terminus of the $V_HH$ single domain antibody, and the C-terminus of the $V_HH$ single domain antibody is connected to the N-terminus of the interleukin-21 domain; or wherein the C-terminus of the interleukin-21 domain is connected to the N-terminus of the $V_HH$ single domain antibody, the C-terminus of the $V_HH$ single domain antibody is connected to the N-terminus of the peptide linker, and the C-terminus of the peptide linker is connected to the N-terminus of the interleukin-2 domain.

In yet another embodiment, provided herein is a fusion protein comprising one interleukin-2 domain having an amino acid sequence of SEQ ID NO: 2 or 8; one interleukin-21 domain having an amino acid sequence of SEQ ID NO:

156 or 157; one V$_H$H single domain antibody having an amino acid sequence of SEQ ID NO: 108 or 115; and one peptide linker having an amino acid sequence of SEQ ID NO: 126 or 133; wherein the C-terminus of the interleukin-2 domain is connected to the N-terminus of the peptide linker, the C-terminus of the peptide linker is connected to the N-terminus of the V$_H$H single domain antibody, and the C-terminus of the V$_H$H single domain antibody is connected to the N-terminus of the interleukin-21 domain; or wherein the C-terminus of the interleukin-21 domain is connected to the N-terminus of the V$_H$H single domain antibody, the C-terminus of the V$_H$H single domain antibody is connected to the N-terminus of the peptide linker, and the C-terminus of the peptide linker is connected to the N-terminus of the interleukin-2 domain.

In still another embodiment, provided herein is an interleukin-2 and interleukin-21 fusion protein having an amino acid sequence of any one of SEQ ID NOs: 159 to 171.

In one embodiment, provided herein is a fusion protein comprising one interleukin-2 domain having an amino acid sequence of any one of SEQ ID NOs: 1 to 97; one interleukin-21 domain having an amino acid sequence of any one of SEQ ID NOs: 156 to 158; one Fc domain having an amino acid sequence of any one of SEQ ID NOs: 116 to 123; and optionally one or two peptide linkers, each independently having an amino acid sequence of GSG or any one of SEQ ID NOs: 124 to 155.

In another embodiment, provided herein is a fusion protein comprising two interleukin-2 domains, each independently having an amino acid sequence of any one of SEQ ID NOs: 1 to 97; one interleukin-21 domain having an amino acid sequence of any one of SEQ ID NOs: 156 to 158; one Fc domain having an amino acid sequence of any one of SEQ ID NOs: 116 to 123; and optionally one, two, or three peptide linkers, each independently having an amino acid sequence of GSG or any one of SEQ ID NOs: 124 to 155.

In one embodiment, the fusion protein provided herein is produced from a yeast cell, insect cell, mammalian cell, a human cell, or a plant cell. In another embodiment, the fusion protein provided herein is produced from a yeast cell. In yet another embodiment, the fusion protein provided herein is produced from an insect cell. In yet another embodiment, the fusion protein provided herein is produced from a mammalian cell. In yet another embodiment, the fusion protein provided herein is produced from a CHO cell. In yet another embodiment, the fusion protein provided herein is produced from a human cell. In yet another embodiment, the fusion protein provided herein is produced from a plant cell.

Pharmaceutical Compositions

In one embodiment, provided herein is a pharmaceutical composition comprising a fusion protein provided herein and a pharmaceutically acceptable excipient.

In one embodiment, the pharmaceutical composition is formulated as single dosage form.

In one embodiment, the pharmaceutical composition provided herein is a solid formulation. In another embodiment, the pharmaceutical composition provided herein is a lyophilized solid formulation. In yet another embodiment, the pharmaceutical composition provided herein is a solution. In yet another embodiment, the pharmaceutical composition provided herein is an aqueous solution. In still another embodiment, the pharmaceutical composition provided herein is sterilized.

In one embodiment, the pharmaceutical composition provided herein is formulated in a dosage form for parenteral administration. In another embodiment, the pharmaceutical composition provided herein is formulated in a dosage form for intravenous administration. In yet another embodiment, the pharmaceutical composition provided herein is formulated in a dosage form for intramuscular administration. In yet another embodiment, the pharmaceutical composition provided herein is formulated in a dosage form for subcutaneous administration. In still another embodiment, the pharmaceutical composition provided herein is formulated in a dosage form for intratumoral administration.

Methods of Use

In one embodiment, provided herein is a method for treating, preventing, or ameliorating a proliferative disease in a subject, comprising administering to the subject in need thereof a therapeutically effective amount of a fusion protein provided herein.

In one embodiment, the proliferative disease is cancer. In another embodiment, the proliferative disease is metastatic cancer. In yet another embodiment, the proliferative disease is renal cell carcinoma (RCC) or melanoma. In yet another embodiment, the proliferative disease is metastatic renal cell carcinoma (RCC) or metastatic melanoma.

In another embodiment, provided herein is a method of activating an immune effector cell, comprising contacting the cell with an effective amount of a fusion protein provided herein.

In certain embodiments, the therapeutically effective amount is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

In certain embodiments, the subject is a mammal. In certain embodiments, the subject is a human.

The disclosure will be further understood by the following non-limiting examples.

EXAMPLES

Example 1

Cloning, Expression, and Purification of IL-2 and IL-21 Fusion Proteins

The amino acid sequences of the human IL-2 and IL-21 were obtained from UNIPROT (IL-2: P60568, 21-153 aa; IL-21: Q9HBE4, 25-162 aa). The deoxyoligonucleotide sequences encoding the human IL-2 and IL-21 were codon optimized for CHO cell expression. The deoxyoligonucleotide sequences of the human IL-2, IL-21, and their muteins were commercially synthesized.

Figure 4:
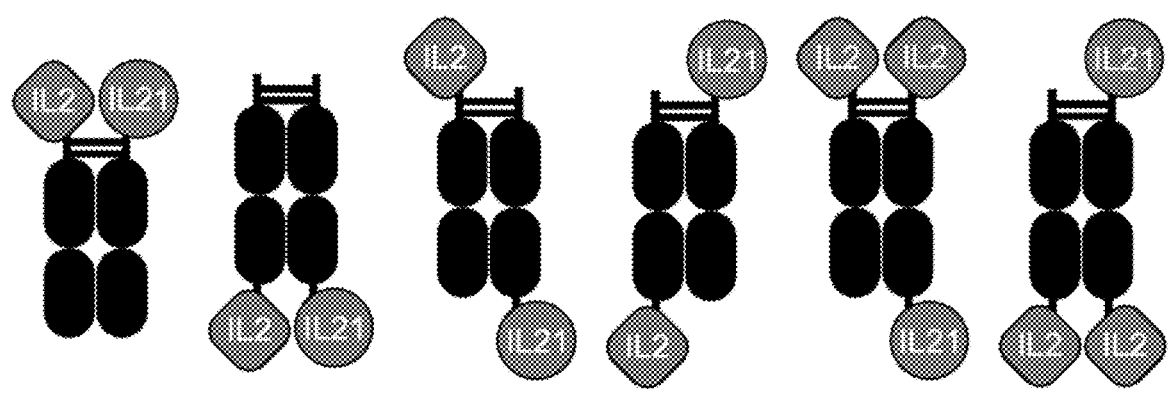
FIG. 4 shows the configurations of exemplary fusion proteins comprising an IL-2 domain, an IL-21 domain, and an Fc domain with two peptide chains as an example of a half-life extension domain.
Figure 5:
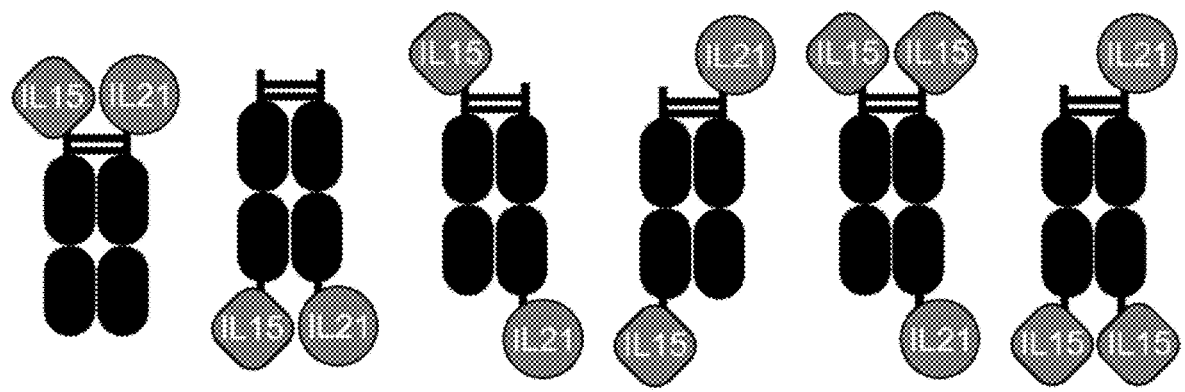
FIG. 5 shows the configurations of exemplary fusion proteins comprising an IL-15 domain, an IL-21 domain, and an Fc domain with two peptide chains as an example of a half-life extension domain.
Figure 6:
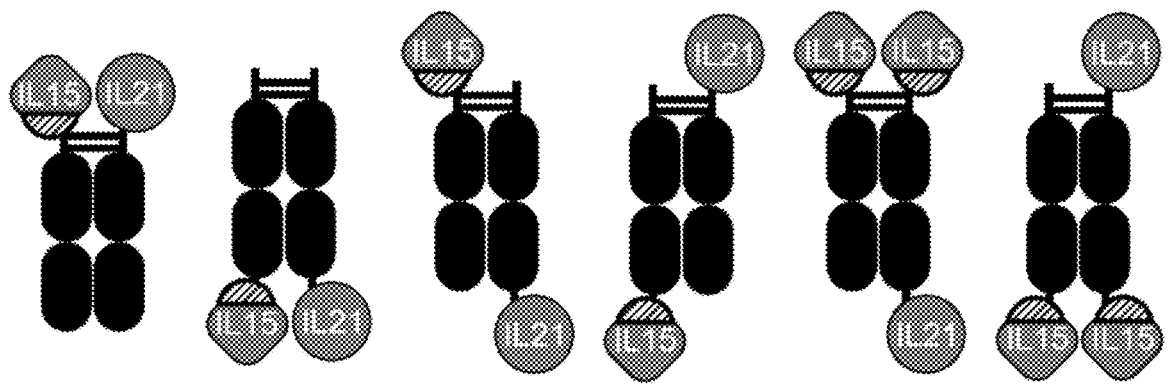
FIG. 6 shows the configurations of exemplary fusion proteins comprising an IL-15 variant domain, an IL-21 domain, and an Fc domain with two peptide chains as an example of a half-life extension domain.
Figure 7:
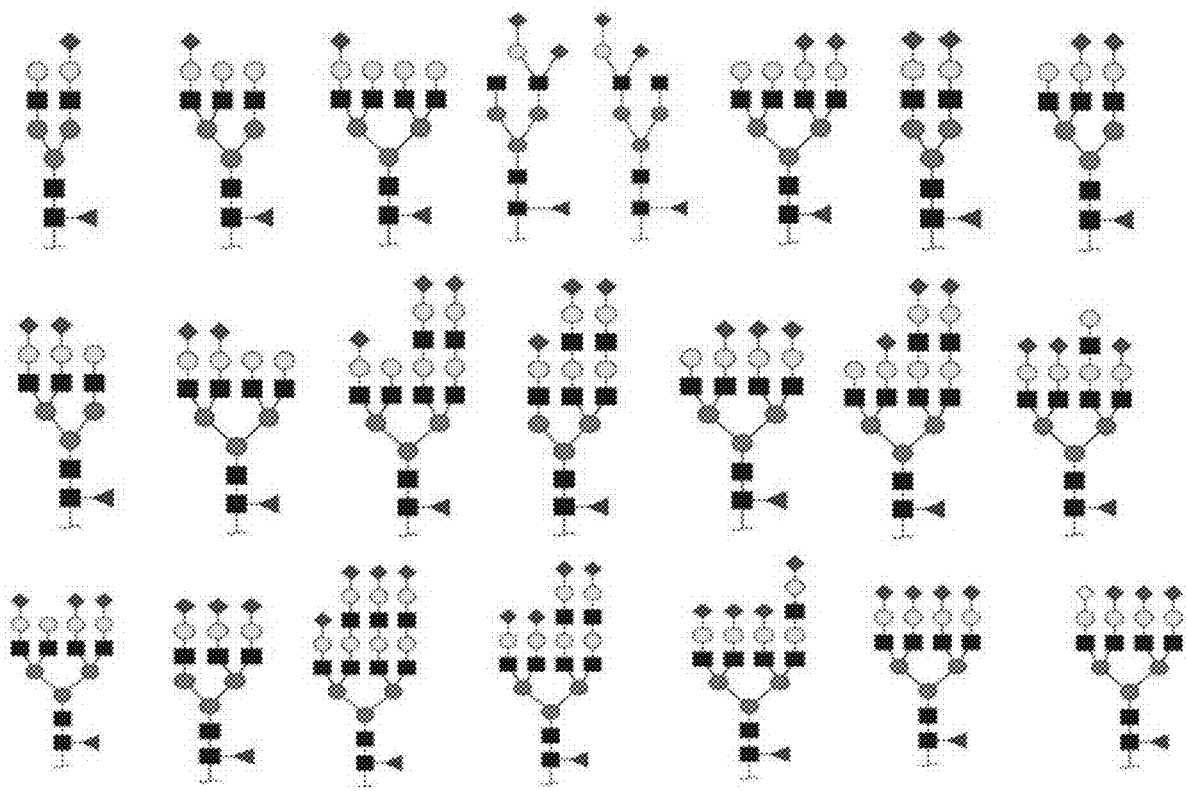
FIG. 7 illustrates the structures of certain N-glycans.

Certain configurations of fusion proteins containing (i) the human IL-2 or a mutein thereof, (ii) the human IL-21 or a mutein thereof, and (iii) an anti-human serum albumin (HSA) antibody are illustrated in FIG. 1. Certain configurations of fusion proteins containing (i) the human IL-2 or a mutein thereof, (ii) the human IL-21 or a mutein thereof, and (iii) a human IgG Fc or a mutein thereof are illustrated in FIG. 4.

The deoxyoligonucleotide sequences encoding the human IL-2, IL-21, peptide linkers, and an anti-HSA V$_H$H antibody or human IgG Fc were seamlessly assembled together by homology assembly cloning with commercially available kits. The oligonucleotides of the fusion proteins were each independently inserted into a UCOE® expression vector CET1019-AS-Puro for CHO cell expression.

The oligonucleotide sequence encoding a fusion protein was transiently expressed in EXPICHO™ cells. Briefly, on Day −1, EXPICHO-S™ cells were seeded at 3-4×10$^6$ cells/mL with the EXPICHO™ expression medium in a vented Erlenmeyer shake flask. The flask was placed on a 125 rpm orbital shaker in a 37° C. incubator with 8% $CO_2$. On Day 0, plasmid DNA was mixed with the EXPIFECTAMINE™ CHO reagent. The mixture was then slowly added to the cells. After 16 hours, the cells were transferred to a 32° C. incubator with 5% $CO_2$. The cells were fed twice on Day 1 and Day 5 with the EXPICHO™ feed. The CHO cells were harvested on Day 8-12.

The fusion proteins produced in the CHO cells were purified by a two-step purification process comprising protein A affinity chromatography using protein A (e.g., AMSPHERE™ A3) resin and ion exchange chromatography (e.g., CAPTO™ S IMPACT).

For the protein A affinity chromatography, a protein A affinity column was loaded with a clarified CHO medium and then washed twice with 20 mM sodium phosphate and once with 20 mM sodium phosphate with 0.5 M NaCl at pH 7.5. The fusion protein was eluted with 50 mM sodium acetate at pH 3.0 supplied with 1% isopropanol by volume.

The purified fusion protein was then buffer exchanged into 20 mM sodium phosphate at pH 6.0 in preparation of AKTA™ purification. The fusion protein was loaded onto 1 mL HITRAP CAPTO™ S IMPACT column. After loading, the column was washed with 20 mM sodium phosphate at pH 6.0 for 10 column volumes (CV). After washing, the fusion protein was eluted with 20 mM sodium phosphate at pH 6.0 plus 1 M NaCl by a gradient of 0-100% in 22.5 CV. The fusion protein was eluted off at ~12 mS/cm. Eluted fractions were pooled and buffer exchanged into a solution containing 5 mM histidine, 20 mM NaCl, and 0.02% TWEEN-80 at pH 4.0 for storage.

Example 2

Effect of IL-2/IL-21 Fusion Proteins on STAT3 Signaling

The IL-2/IL-21 fusion proteins were evaluated in a STAT3 signaling assay.

Pfeiffer cells were maintained in RPMI-1640 containing 10% fetal bovine serum and penicillin/streptomycin. The Pfeiffer cells (100,000) were treated with a hIL-21-anti-HSA fusion protein (C1) as a control; or IL-2/IL-21 fusion proteins for 30 minutes at 37° C. and 5% $CO_2$ in Hanks balanced salt solution containing 10 mM HEPES. Phospho-STAT3 was measured using a phospho-STAT3 (Tyr705) homogeneous time resolved fluorescence (HTRF) assay. The signal ratio at 665 nm/620 nm was multiplied by 1000, plotted, and fit using a dose response curve (GRAPHPAD PRISM) to calculate $EC_{50}$ values. The $EC_{50}$ values determined are summarized in Table 1 below.

In the table, C1 represents a hIL-21-anti-HSA fusion protein comprising an IL-21 domain of an amino acid sequence of SEQ ID NO: 156 and an sdAb of SEQ ID NO: 108, where the C-terminus of the IL-21 domain is connected directly to the N-terminus of the sdAb.

A1 represents an IL-2/IL-21 fusion protein of SEQ ID NO: 159, which comprises an IL-2 domain of SEQ ID NO: 2, an IL-21 domain of SEQ ID NO: 156, an sdAb of SEQ ID NO: 108, and a peptide linker of SEQ ID NO: 126, where the C-terminus of the IL-21 domain is connected directly to the N-terminus of the sdAb, the N-terminus of which is connected directly to the C-terminus of the peptide linker, the N-terminus of which is connected directly to the C-terminus of the IL-2 domain.

A2 represents an IL-2/IL-21 fusion protein of SEQ ID NO: 160, which comprises an IL-2 domain of SEQ ID NO: 20, an IL-21 domain of SEQ ID NO: 156, an sdAb of SEQ ID NO: 108, and a peptide linker of SEQ ID NO: 126, where the C-terminus of the IL-2 domain is connected directly to the N-terminus of the peptide linker, the N-terminus of which is connected directly to the C-terminus of the sdAb, the N-terminus of which is connected directly to the C-terminus of the IL-21 domain.

A3 represents an IL-2/IL-21 fusion protein of SEQ ID NO: 161, which comprises an IL-2 domain of SEQ ID NO: 20, an IL-21 domain of SEQ ID NO: 156, an sdAb of SEQ ID NO: 108, and a peptide linker of SEQ ID NO: 126, where the C-terminus of the IL-21 domain is connected directly to the N-terminus of the sdAb, the N-terminus of which is connected directly to the C-terminus of the peptide linker, the N-terminus of which is connected directly to the C-terminus of the IL-2 domain.

A4 represents an IL-2/IL-21 fusion protein of SEQ ID NO: 163, which comprises an IL-2 domain of SEQ ID NO: 20, an IL-21 domain of SEQ ID NO: 157, an sdAb of SEQ ID NO: 108, and a peptide linker of SEQ ID NO: 126, where the C-terminus of the IL-21 domain is connected directly to the N-terminus of the sdAb, the N-terminus of which is connected directly to the C-terminus of the peptide linker, the N-terminus of which is connected directly to the C-terminus of the IL-2 domain.

TABLE 1

|  | C1 | A1 | A2 | A3 | A4 |
| --- | --- | --- | --- | --- | --- |
| $EC_{50}$ (pM) | 95 | 82 | 89 | 61 | 199 |

The results show that the IL-2/IL-21 fusion proteins have similar signaling potency as the hIL-21-anti-HSA fusion protein (C1) in activating the STAT3 signaling pathway.

Example 3

Effect of IL-2/IL-21 Fusion Proteins on STAT5 Signaling

The IL-2/IL-21 fusion proteins were evaluated in a STAT5 signaling assay.

Lousy cells were maintained in RPMI-1640 containing 10% fetal bovine serum and penicillin/streptomycin. The Loucy cells (100,000) were treated with a hIL-2-anti-HSA fusion protein (hIL-2-anti-HSA (C2) or hIL-2 mutant-anti-HSA (C3)) as a control, or IL-2/IL-21 fusion proteins for 30 minutes at 37° C. and 5% $CO_2$ in the Hanks balanced salt solution containing 10 mM HEPES. Phospho-STAT5 was measured using a phospho-STAT5 (Tyr694) homogeneous time resolved fluorescence (HTRF) assay. The signal ratio at 665 nm/620 nm was multiplied by 1000, plotted, and fit using a dose response curve (GRAPHPAD PRISM) to calculate $EC_{50}$ values. The $EC_{50}$ values determined are summarized in Table 2 below.

In the table, C2 represents a hIL-2-anti-HSA fusion protein comprising an IL-2 domain of an amino acid sequence of SEQ ID NO: 2, an sdAb of SEQ ID NO: 108, and a peptide linker of SEQ ID NO: 126, where the C-terminus of the IL-2 domain is connected directly to the N-terminus of the peptide linker, the C-terminus of which is connected directly to the N-terminus of the sdAb. C3 represents a hIL-2-anti-HSA fusion protein comprising an IL-2 domain of an amino acid sequence of SEQ ID NO: 20, an sdAb of SEQ ID NO: 108, and a peptide linker of SEQ ID NO: 126, where the C-terminus of the IL-2 domain is connected directly to the N-terminus of the peptide linker, the C-terminus of which is connected directly to the N-terminus of the sdAb.

TABLE 2

|  | C2 | C3 | A1 | A2 | A3 | A4 |
|---|---|---|---|---|---|---|
| $EC_{50}$ (nM) | 9.0 | 5.1 | 1.5 | 2.2 | 1.6 | 3.2 |

The results show that the IL-2/IL-21 fusion proteins have better signaling potency compared to hIL-2-anti-HSA (C2) and glycosylated hIL-2-anti-HSA (C3) in cells that only express IL-2Rβ and IL-2Rγ.

Example 4

In Vitro Potency of IL-2/IL-21 Fusion Proteins with CD3/CD28 Activated T-Cells

The in vitro potency of hIL-21-anti-HSA (C1), hIL-2-anti-HSA (C2), or fusion proteins (A1, A2, and A3) was determined by quantifying improvement in N87 (stomach cancer) cell killing by CD3/CD28 stimulated CD3+ T-cell.

The N87 cancer cells were maintained in RPMI-1640 containing 10% fetal bovine serum and penicillin/streptomycin. On Day 0, 10,000 N87 cells/well were plated in the culture medium in a 96-well flat bottom plate. On Day 1, 30,000 CD3+ T cells/well and 1:300 diluted anti-CD3/anti-CD28 antibody complex were added to the cancer cells together with hIL-21-anti-HAS (C1), hIL-2-anti-HSA (C2), or fusion proteins (A1, A2, and A3). The plates were incubated for 72 h at 37° C. and 5% $CO_2$. The cells were then fixed with 4% paraformaldehyde and nuclei stained with SYTOX™ Orange. The number of remaining cancer cells was calculated by counting the number of cancer cell nuclei remaining in each well using the CYTATION™ 1. The $IC_{50}$ values determined are summarized in Table 3 below.

TABLE 3

|  | C1 | C2 | A1 | A2 | A3 |
|---|---|---|---|---|---|
| $IC_{50}$ (pM) | 13.7 | 9.8 | 5.4 | 3.4 | 1.6 |

Example 5

Binding Studies of IL-2/IL-21 Fusion Proteins to Human IL-2Rα

OCTET® RED96 is used to characterize the interactions of IL-2/IL-21 fusion proteins with a human IL-2Rα. Briefly, an IL-2Rα-Fc fusion protein is loaded onto an anti-human IgG Fc capture (AHC) biosensor. The biosensor is then dipped into a solution containing an IL-2/IL-21 fusion protein at 100, 200, 400, or 800 nM. Primary experimental data is analyzed with global fitting to determine a dissociation constant ($K_d$).

Example 6

Binding Studies of IL-2/IL-21 Fusion Proteins to Human IL-2Rβ

OCTET® RED96 is used to characterize the interactions of IL-2/IL-21 fusion proteins with a human IL-2Rβ. Briefly, an IL-2Rβ-Fc fusion protein is loaded onto an anti-human IgG Fc capture (AHC) biosensor. The biosensor is then dipped into a solution containing an IL-2/IL-21 fusion protein at 200, 400, or 800 nM. Primary experimental data is analyzed with global fitting to determine a dissociation constant ($K_d$).

Example 7

Glycan Analysis

The glycan profile of a fusion protein is analyzed using an ADVANCEBIO GLY-X™ N-glycan prep with INSTANTPC™ kit. The domain is denatured and N-glycans are released by an N-glycanase at 50° C. The released N-glycans are labeled by an INSTANTPC™ dye and then cleaned up with a Gly-X™. The labeled glycans are analyzed on an HPLC system equipped with an ACQUITY UPLC Glycan BEH Amide column (130 Å, 1.7 μm, 2.1 mm×150 mm) connected to a Shimadzu NEXERA-I LC-2040C 3D MT coupled with a RF-20A fluorescence detector. The N-glycans are identified by comparing them with the INSTANTPC™ labeled glycan standard libraries from Agilent Technologies.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A fusion protein comprising an interleukin-2 domain, an interleukin-21 domain, and an albumin binding domain; wherein the interleukin-2 domain comprises the amino acid sequence of SEQ ID NO: 1, 2, 3, 4, or 5; or wherein the interleukin-2 domain is an N-glycosylated interleukin-2 comprising one, two, three, or four substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in the amino acid sequence of SEQ ID NO: 1, 2, 3, 4, or 5; wherein the interleukin-21 domain comprises the amino acid sequence of SEQ ID NO: 156, 157, or 158; and wherein the C-terminus of the interleukin-2 domain is connected to the N-terminus of the interleukin-21 domain directly or via a peptide linker; and the C-terminus of the interleukin-21 domain is connected to the N-terminus of the albumin binding domain directly or via a peptide linker; or wherein the C-terminus of the interleukin-21 domain is connected to the N-terminus of the interleukin-2 domain directly or via a peptide linker; and the C-terminus of the interleukin-2 domain is connected to the N-terminus of the albumin binding domain directly or via a peptide linker; or wherein the C-terminus of the interleukin-2 domain is connected to the N-terminus of the albumin binding domain directly or via a peptide linker; and the C-terminus of the albumin binding domain is connected to the N-terminus of the interleukin-21 domain directly or via a peptide linker; or wherein the C-terminus of the interleukin-21 domain is connected to the N-terminus of the albumin binding domain directly or via a peptide linker; and the C-terminus of the albumin binding domain is connected to the N-terminus of the interleukin-2 domain directly or via a peptide linker; or wherein the C-terminus of the albumin binding domain is connected to the N-terminus of the interleukin-2 domain directly or via a peptide linker; and the C-terminus of the interleukin-2 domain is connected to the N-terminus of the interleukin-21 domain directly or via a peptide linker; or wherein the C-terminus of the albumin binding domain is connected to the N-terminus of the interleukin-21 domain directly or via a peptide linker; and the C-terminus of the interleukin-21 domain is connected to the N-terminus of the interleukin-2 domain directly or via a peptide linker.

2. The fusion protein of claim 1, comprising an interleukin-2 domain, an interleukin-21 domain, an albumin binding domain, and optionally first and second peptide linkers; wherein the C-terminus of the interleukin-2 domain is connected to the N-terminus of the albumin binding domain directly or via the first peptide linker; and the C-terminus of the albumin binding domain is connected to the N-terminus of the interleukin-21 domain directly or via the second peptide linker.

3. The fusion protein of claim 1, comprising an interleukin-2 domain, an interleukin-21 domain, an albumin binding domain, and optionally first and second peptide linkers; wherein the C-terminus of the interleukin-21 domain is connected to the N-terminus of the albumin binding domain directly or via the first peptide linker; and the C-terminus of the albumin binding domain is connected to the N-terminus of the interleukin-2 domain directly or via the second peptide linker.

4. The fusion protein of claim 1, wherein the albumin binding domain is a single domain antibody.

5. The fusion protein of claim 4, wherein the single domain antibody comprises: (i) CDR1 of SEQ ID NO: 101, CDR2 of SEQ ID NO: 102, and CDR3 of SEQ ID NO: 103; or (ii) CDR1 of SEQ ID NO: 109, CDR2 of SEQ ID NO: 110, and CDR3 of SEQ ID NO: 111.

6. The fusion protein of claim 1, wherein the interleukin-2 domain comprises one, two, three, or four substitutions at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in the amino acid sequence of SEQ ID NO: 1, 2, 3, 4, or 5.

7. The fusion protein of claim 6, wherein the interleukin-2 domain comprises four substitutions at positions R38, L40, F42, and Y45 as set forth in the amino acid sequence of SEQ ID NO: 1, 2, 3, 4, or 5.

8. The fusion protein of claim 1, wherein the interleukin-2 domain comprises an N-glycosylation site having the amino acid sequence of NXT or NXS, wherein each X is independently A, C, D, E, F, G, H, I, K, L, M, N, Q, R, S, T, V, W, or Y.

9. The fusion protein of claim 1, wherein the interleukin-2 domain comprises an N-glycosylation site having the amino acid sequence of NMT or NMS, each independently starting at position 38 or 45 as set forth in the amino acid sequence of SEQ ID NO: 1, 2, 3, 4, or 5.

10. The fusion protein of claim 1, wherein the interleukin-2 domain comprises an N-glycosylation site at an interface residue between an interleukin-2 and an interleukin-2 receptor-α chain.

11. The fusion protein of claim 10, wherein the interface residue is R38 as set forth in in the amino acid sequence of SEQ ID NO: 1, 2, 3, 4, or 5.

12. The fusion protein of claim 1, wherein the interleukin-2 domain comprises two amino acid substitutions: (i) R38N and (ii) L40T or L40S as set forth in the amino acid sequence of SEQ ID NO: 1, 2, 3, 4, or 5.

13. The fusion protein of claim 1, wherein the interleukin-2 domain comprises three amino acid substitutions: (i) R38N, (ii) L40T or L40S, and (iii) F42A, Y45A, E61A, or E62A, as set forth in the amino acid sequence of SEQ ID NO: 1, 2, 3, 4, or 5.

14. The fusion protein of claim 1, wherein the interleukin-2 domain comprises four amino acid substitutions: (i) R38N, (ii) L40T or L40S, (iii) K43N, or (iv) Y45T or Y45S, as set forth in the amino acid sequence of SEQ ID NO: 1, 2, 3, 4, or 5.

15. The fusion protein of claim 1, wherein the interleukin-2 domain comprises the amino acid sequence selected from SEQ ID NOs: 1 to 5 and 18.

16. The fusion protein of claim 1, wherein the interleukin-2 domain comprises the amino acid sequence selected from SEQ ID NOs: 1 to 5.

17. The fusion protein of claim 1, wherein the interleukin-2 domain comprises the amino acid sequence of SEQ ID NO: 18.

18. The fusion protein of claim 1, wherein the interleukin-21 domain comprises the amino acid sequence of SEQ ID NO: 156 or 157.

19. The fusion protein of claim 1, comprising one interleukin-2 domain having the amino acid sequence of any one of SEQ ID NOs: 1 to 5 and 18; one interleukin-21 domain having the amino acid sequence of any one of SEQ ID NOs: 156 to 158; one $V_HH$ single domain antibody having the amino acid sequence of SEQ ID NO: 108 or 115; and optionally one or two peptide linkers, each independently having the amino acid sequence of GSG or any one of SEQ ID NOs: 124 to 155.

20. The fusion protein of claim 1, comprising one interleukin-2 domain having the amino acid sequence of SEQ ID NO: 2 or 18; one interleukin-21 domain having the amino acid sequence of SEQ ID NO: 156 or 157; one $V_HH$ single domain antibody having the amino acid sequence of SEQ ID NO: 108 or 115; and optionally one or two peptide linkers, each independently having the amino acid sequence of SEQ ID NO: 126 or 133.

21. The fusion protein of claim 1, comprising one interleukin-2 domain having the amino acid sequence of any one of SEQ ID NOs: 1 to 5 and 18; one interleukin-21 domain having the amino acid sequence of any one of SEQ ID NOs: 156 to 158; one $V_HH$ single domain antibody having the amino acid sequence of SEQ ID NO: 108 or 115; and one peptide linker having the amino acid sequence of GSG or any one of SEQ ID NOs: 124 to 155; wherein the C-terminus of the interleukin-2 domain is connected to the N-terminus of the peptide linker, the C-terminus of the peptide linker is connected to the N-terminus of the $V_HH$ single domain antibody, and the C-terminus of the $V_HH$ single domain antibody is connected to the N-terminus of the interleukin-21 domain; or wherein the C-terminus of the interleukin-21 domain is connected to the N-terminus of the $V_HH$ single domain antibody, the C-terminus of the $V_HH$ single domain antibody is connected to the N-terminus of the peptide linker, and the C-terminus of the peptide linker is connected to the N-terminus of the interleukin-2 domain.

22. The fusion protein of claim 1, comprising one interleukin-2 domain having the amino acid sequence of SEQ ID NO: 2 or 18; one interleukin-21 domain having the amino acid sequence of SEQ ID NO: 156 or 157; one $V_HH$ single domain antibody having the amino acid sequence of SEQ ID NO: 108 or 115; and one peptide linker having the amino acid sequence of SEQ ID NO: 126 or 133; wherein the C-terminus of the interleukin-2 domain is connected to the N-terminus of the peptide linker, the C-terminus of the peptide linker is connected to the N-terminus of the $V_HH$ single domain antibody, and the C-terminus of the $V_HH$ single domain antibody is connected to the N-terminus of the interleukin-21 domain; or wherein the C-terminus of the interleukin-21 domain is connected to the N-terminus of the $V_HH$ single domain antibody, the C-terminus of the $V_HH$ single domain antibody is connected to the N-terminus of the peptide linker, and the C-terminus of the peptide linker is connected to the N-terminus of the interleukin-2 domain.

23. The fusion protein of claim 1, having the amino acid sequence selected from SEQ ID NOs: 159 to 163 and 166 to 171.

24. A pharmaceutical composition comprising the fusion protein of claim 1, and a pharmaceutically acceptable excipient.

25. The fusion protein of claim 4, wherein the single domain antibody has the amino acid sequence of SEQ ID NO: 108 or 115.

26. The fusion protein of claim 4, wherein the single domain antibody has the amino acid sequence of SEQ ID NO: 108.

27. The fusion protein of claim 4, wherein the single domain antibody has the amino acid sequence of SEQ ID NO: 115.

28. The fusion protein of claim 6, wherein the interleukin-2 domain comprises an amino acid substitution at position P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, or T111 as set forth in the amino acid sequence of SEQ ID NO: 1, 2, 3, 4, or 5.

29. The fusion protein of claim 6, wherein the interleukin-2 domain comprises two amino acid substitutions at positions P34, K35, L36, T37, R38, M39, L40, T41, F42, K43, F44, Y45, M46, P47, E61, E62, L63, K64, P65, L66, E67, E68, V69, L70, N71, L72, A73, Q74, Y107, D109, and/or T111 as set forth in the amino acid sequence of SEQ ID NO: 1, 2, 3, 4, or 5.

30. The fusion protein of claim 6, wherein the interleukin-2 domain comprises two amino acid substitutions at positions P34, K35, L36, T37, R38, L40, T41, F42, K43, F44, Y45, M46, P47, E61, E62, L63, P65, L66, E67, E68, V69, L70, N71, L72, Q74, Y107, D109, and/or T111 as set forth in the amino acid sequence of SEQ ID NO: 1, 2, 3, 4, or 5.

31. The fusion protein of claim 1, wherein the interleukin-2 domain comprises one, two, three, or four substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in the amino acid sequence of SEQ ID NO: 1, 2, 3, 4, or 5.

32. The fusion protein of claim 31, wherein the interleukin-2 domain comprises a substitution selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in the amino acid sequence of SEQ ID NO: 1, 2, 3, 4, or 5.

33. The fusion protein of claim 31, wherein the interleukin-2 domain comprises two substitutions selected from P34N, K35N, T37N, R38N, M39N, T41N, F42N, K43N, F44N, Y45N, E61N, E62N, K64N, P65N, L66N, E68N, V69N, L72N, Y107N, and D109N as set forth in the amino acid sequence of SEQ ID NO: 1, 2, 3, 4, or 5.

34. The fusion protein of claim 1, wherein each peptide linker is independently a peptide linker having the amino acid sequence of GSG or one of SEQ ID NOs: 124 to 155.

* * * * *

SEQUENCE LISTING

<160> NUMBER OF SEQ ID NOS: 172

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His

```
                1               5                  10                  15
Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
                50                  55                  60

Pro Leu Glu Glu Val Leu Asn Leu Ala Gln Ser Lys Asn Phe His Leu
 65                 70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
                130

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
                50                  55                  60

Pro Leu Glu Glu Val Leu Asn Leu Ala Gln Ser Lys Asn Phe His Leu
 65                 70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
                130

<210> SEQ ID NO 3
<211> LENGTH: 133
<212> TYPE: PRT
<213> ORGANISM: Homo sapiens

<400> SEQUENCE: 3

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
```

```
                 50                  55                  60
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ala Gln Ser Ile
                115                 120                 125

Ile Ser Thr Leu Thr
            130

<210> SEQ ID NO 4
<211> LENGTH: 133
<212> TYPE: PRT
<213> ORGANISM: Homo sapiens

<400> SEQUENCE: 4

Ala Pro Ala Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
                 35                  40                  45

Lys Ala Thr Glu Leu Lys His Leu Gln Cys Leu Glu Glu Glu Leu Lys
             50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 5
<211> LENGTH: 133
<212> TYPE: PRT
<213> ORGANISM: Homo sapiens

<400> SEQUENCE: 5

Ala Pro Ala Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
                 35                  40                  45

Lys Ala Thr Glu Leu Lys His Leu Gln Cys Leu Glu Glu Glu Leu Lys
             50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
```

```
                    100                 105                 110
Thr Ile Val Glu Phe Leu Asn Arg Trp Ile Thr Phe Ala Gln Ser Ile
            115                 120                 125
Ile Ser Thr Leu Thr
        130

<210> SEQ ID NO 6
<211> LENGTH: 133
<212> TYPE: PRT
<213> ORGANISM: Homo sapiens

<400> SEQUENCE: 6

Ala Pro Thr Ser Ser Thr Lys Lys Thr Gln Leu Gln Leu Glu His
 1               5                  10                  15

Leu Leu Asp Leu Gln Met Ile Leu Asn Gly Ile Asn Asn Tyr Lys
            20                  25                  30

Asn Asn Lys Thr Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 7
<211> LENGTH: 133
<212> TYPE: PRT
<213> ORGANISM: Homo sapiens

<400> SEQUENCE: 7

Ala Pro Thr Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Asn Lys Ser Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Ser Gln Ser Ile
            115                 120                 125

Ile Ser Thr Leu Thr
        130
```

-continued

```
<210> SEQ ID NO 8
<211> LENGTH: 133
<212> TYPE: PRT
<213> ORGANISM: Homo sapiens

<400> SEQUENCE: 8

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Asn Lys Thr Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 9
<211> LENGTH: 133
<212> TYPE: PRT
<213> ORGANISM: Homo sapiens

<400> SEQUENCE: 9

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Asn Lys Ser Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 10
<211> LENGTH: 133
<212> TYPE: PRT
<213> ORGANISM: Homo sapiens

<400> SEQUENCE: 10

Ala Pro Thr Ser Ser Ser Thr Lys Lys Thr Gln Leu Gln Leu Glu His
1               5                   10                  15
```

Leu Leu Leu Asp Leu Gln Met Ile Leu Asn Gly Ile Asn Asn Tyr Lys
            20                  25                  30

Asn Pro Asn Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
                115                 120                 125

Ile Ser Thr Leu Thr
        130

<210> SEQ ID NO 11
<211> LENGTH: 133
<212> TYPE: PRT
<213> ORGANISM: Homo sapiens

<400> SEQUENCE: 11

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Asn Leu Ser Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
                115                 120                 125

Ile Ser Thr Leu Thr
        130

<210> SEQ ID NO 12
<211> LENGTH: 133
<212> TYPE: PRT
<213> ORGANISM: Homo sapiens

<400> SEQUENCE: 12

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Asn Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
 50                  55                  60

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 13
<211> LENGTH: 133
<212> TYPE: PRT
<213> ORGANISM: Homo sapiens

<400> SEQUENCE: 13

Ala Pro Ala Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Asn Leu Ser Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 14
<211> LENGTH: 133
<212> TYPE: PRT
<213> ORGANISM: Homo sapiens

<400> SEQUENCE: 14

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Asn Arg Thr Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Ser Gln Ser Ile
        115                 120                 125

Ile Ser Thr Leu Thr
    130

<210> SEQ ID NO 15
<211> LENGTH: 133
<212> TYPE: PRT
<213> ORGANISM: Homo sapiens

<400> SEQUENCE: 15

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Asn Arg Ser Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 16
<211> LENGTH: 133
<212> TYPE: PRT
<213> ORGANISM: Homo sapiens

<400> SEQUENCE: 16

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Asn Arg Thr Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 17
```

```
<211> LENGTH: 133
<212> TYPE: PRT
<213> ORGANISM: Homo sapiens

<400> SEQUENCE: 17

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Asn Arg Ser Leu Thr Phe Lys Phe Tyr Met Pro Lys
                35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 18
<211> LENGTH: 133
<212> TYPE: PRT
<213> ORGANISM: Homo sapiens

<400> SEQUENCE: 18

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
                35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 19
<211> LENGTH: 133
<212> TYPE: PRT
<213> ORGANISM: Homo sapiens

<400> SEQUENCE: 19

Ala Pro Thr Ser Ser Ser Thr Lys Lys Thr Gln Leu Gln Leu Glu His
1               5                   10                  15
```

Leu Leu Leu Asp Leu Gln Met Ile Leu Asn Gly Ile Asn Asn Tyr Lys
            20                  25                  30

Asn Pro Lys Leu Thr Asn Met Ser Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 20
<211> LENGTH: 133
<212> TYPE: PRT
<213> ORGANISM: Homo sapiens

<400> SEQUENCE: 20

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 21
<211> LENGTH: 133
<212> TYPE: PRT
<213> ORGANISM: Homo sapiens

<400> SEQUENCE: 21

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Ser Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 22
<211> LENGTH: 133
<212> TYPE: PRT
<213> ORGANISM: Homo sapiens

<400> SEQUENCE: 22

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Asn Phe Thr Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 23
<211> LENGTH: 133
<212> TYPE: PRT
<213> ORGANISM: Homo sapiens

<400> SEQUENCE: 23

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Asn Phe Ser Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110
```

Thr Ile Val Glu Phe Leu Asn Arg Trp Ile Thr Phe Ser Gln Ser Ile
            115                 120                 125

Ile Ser Thr Leu Thr
    130

<210> SEQ ID NO 24
<211> LENGTH: 133
<212> TYPE: PRT
<213> ORGANISM: Homo sapiens

<400> SEQUENCE: 24

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Asn Phe Thr Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130

<210> SEQ ID NO 25
<211> LENGTH: 133
<212> TYPE: PRT
<213> ORGANISM: Homo sapiens

<400> SEQUENCE: 25

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Asn Phe Ser Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130

<210> SEQ ID NO 26
<211> LENGTH: 133

```
<212> TYPE: PRT
<213> ORGANISM: Homo sapiens

<400> SEQUENCE: 26

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Asn Lys Thr Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 27
<211> LENGTH: 133
<212> TYPE: PRT
<213> ORGANISM: Homo sapiens

<400> SEQUENCE: 27

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Asn Lys Ser Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 28
<211> LENGTH: 133
<212> TYPE: PRT
<213> ORGANISM: Homo sapiens

<400> SEQUENCE: 28

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
```

-continued

```
                20                  25                  30
Asn Pro Lys Leu Thr Arg Met Leu Thr Asn Lys Thr Tyr Met Pro Lys
            35                  40                  45
Lys Ala Thr Glu Leu Lys His Leu Gln Cys Leu Glu Glu Glu Leu Lys
        50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 29
<211> LENGTH: 133
<212> TYPE: PRT
<213> ORGANISM: Homo sapiens

<400> SEQUENCE: 29

Ala Pro Ala Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Asn Lys Ser Tyr Met Pro Lys
            35                  40                  45
Lys Ala Thr Glu Leu Lys His Leu Gln Cys Leu Glu Glu Glu Leu Lys
        50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 30
<211> LENGTH: 133
<212> TYPE: PRT
<213> ORGANISM: Homo sapiens

<400> SEQUENCE: 30

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Asn Phe Thr Met Pro Lys
            35                  40                  45
Lys Ala Thr Glu Leu Lys His Leu Gln Cys Leu Glu Glu Glu Leu Lys
        50                  55                  60
Pro Leu Glu Glu Val Leu Asn Leu Ala Gln Ser Lys Asn Phe His Leu
```

```
                65                  70                  75                  80
Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 31
<211> LENGTH: 133
<212> TYPE: PRT
<213> ORGANISM: Homo sapiens

<400> SEQUENCE: 31

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Asn Phe Ser Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 32
<211> LENGTH: 133
<212> TYPE: PRT
<213> ORGANISM: Homo sapiens

<400> SEQUENCE: 32

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Asn Phe Thr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
```

```
                115              120              125

Ile Ser Thr Leu Thr
        130

<210> SEQ ID NO 33
<211> LENGTH: 133
<212> TYPE: PRT
<213> ORGANISM: Homo sapiens

<400> SEQUENCE: 33

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Asn Phe Ser Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 34
<211> LENGTH: 133
<212> TYPE: PRT
<213> ORGANISM: Homo sapiens

<400> SEQUENCE: 34

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Asn Tyr Thr Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 35
<211> LENGTH: 133
<212> TYPE: PRT
```

<213> ORGANISM: Homo sapiens

<400> SEQUENCE: 35

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Asn Tyr Ser Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 36
<211> LENGTH: 133
<212> TYPE: PRT
<213> ORGANISM: Homo sapiens

<400> SEQUENCE: 36

Ala Pro Ala Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Asn Tyr Thr Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 37
<211> LENGTH: 133
<212> TYPE: PRT
<213> ORGANISM: Homo sapiens

<400> SEQUENCE: 37

Ala Pro Ala Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Asn Tyr Ser Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 38
<211> LENGTH: 133
<212> TYPE: PRT
<213> ORGANISM: Homo sapiens

<400> SEQUENCE: 38

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Asn Met Thr Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 39
<211> LENGTH: 133
<212> TYPE: PRT
<213> ORGANISM: Homo sapiens

<400> SEQUENCE: 39

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Asn Met Ser Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 40
<211> LENGTH: 133
<212> TYPE: PRT
<213> ORGANISM: Homo sapiens

<400> SEQUENCE: 40

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Asn Met Thr Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 41
<211> LENGTH: 133
<212> TYPE: PRT
<213> ORGANISM: Homo sapiens

<400> SEQUENCE: 41

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Asn Met Ser Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125
```

Ile Ser Thr Leu Thr
    130

<210> SEQ ID NO 42
<211> LENGTH: 133
<212> TYPE: PRT
<213> ORGANISM: Homo sapiens

<400> SEQUENCE: 42

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Asn Glu Thr Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 43
<211> LENGTH: 133
<212> TYPE: PRT
<213> ORGANISM: Homo sapiens

<400> SEQUENCE: 43

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Asn Gly Ser Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 44
<211> LENGTH: 133
<212> TYPE: PRT
<213> ORGANISM: Homo sapiens

<400> SEQUENCE: 44

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Asn Glu Thr Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 45
<211> LENGTH: 133
<212> TYPE: PRT
<213> ORGANISM: Homo sapiens

<400> SEQUENCE: 45

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Asn Glu Ser Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 46
<211> LENGTH: 133
<212> TYPE: PRT
<213> ORGANISM: Homo sapiens

<400> SEQUENCE: 46

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

```
Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Asn Leu Thr
 50                      55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 47
<211> LENGTH: 133
<212> TYPE: PRT
<213> ORGANISM: Homo sapiens

<400> SEQUENCE: 47

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Asn Leu Ser
 50                      55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 48
<211> LENGTH: 133
<212> TYPE: PRT
<213> ORGANISM: Homo sapiens

<400> SEQUENCE: 48

Ala Pro Ala Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Asn Leu Thr
 50                      55                  60

Pro Leu Glu Glu Val Leu Asn Leu Ala Gln Ser Lys Asn Phe His Leu
 65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 49
<211> LENGTH: 133
<212> TYPE: PRT
<213> ORGANISM: Homo sapiens

<400> SEQUENCE: 49

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Asn Leu Ser
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 50
<211> LENGTH: 133
<212> TYPE: PRT
<213> ORGANISM: Homo sapiens

<400> SEQUENCE: 50

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Asn
    50                  55                  60

Ala Thr Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125
```

Ile Ser Thr Leu Thr
    130

<210> SEQ ID NO 51
<211> LENGTH: 133
<212> TYPE: PRT
<213> ORGANISM: Homo sapiens

<400> SEQUENCE: 51

Ala Pro Thr Ser Ser Ser Thr Lys Lys Thr Gln Leu Gln Leu Glu His
1               5                   10                  15

Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Asn
    50                  55                  60

Ala Ser Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 52
<211> LENGTH: 133
<212> TYPE: PRT
<213> ORGANISM: Homo sapiens

<400> SEQUENCE: 52

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Asn
    50                  55                  60

Ala Thr Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 53
<211> LENGTH: 133
<212> TYPE: PRT
<213> ORGANISM: Homo sapiens -continued

```
<400> SEQUENCE: 53

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Asn
    50                  55                  60

Ala Ser Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 54
<211> LENGTH: 133
<212> TYPE: PRT
<213> ORGANISM: Homo sapiens

<400> SEQUENCE: 54

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Asn Leu Thr Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 55
<211> LENGTH: 133
<212> TYPE: PRT
<213> ORGANISM: Homo sapiens

<400> SEQUENCE: 55

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
```

-continued

```
                35                  40                  45
Lys Ala Thr Glu Leu Lys His Leu Gln Cys Leu Glu Glu Leu Lys
 50                  55                  60
Asn Leu Ser Glu Val Leu Asn Leu Ala Gln Ser Lys Asn Phe His Leu
 65                  70                  75                  80
Arg Pro Arg Asp Leu Ile Ser Asn Ile Asn Val Ile Val Leu Glu Leu
                 85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Ser Gln Ser Ile
                115                 120                 125
Ile Ser Thr Leu Thr
            130

<210> SEQ ID NO 56
<211> LENGTH: 133
<212> TYPE: PRT
<213> ORGANISM: Homo sapiens

<400> SEQUENCE: 56

Ala Pro Ala Ser Ser Ser Thr Lys Lys Thr Gln Leu Gln Leu Glu His
  1               5                  10                  15
Leu Leu Leu Asp Leu Gln Met Ile Leu Asn Gly Ile Asn Asn Tyr Lys
                 20                  25                  30
Asn Pro Lys Leu Thr Arg Met Leu Thr Phe Lys Phe Tyr Met Pro Lys
                 35                  40                  45
Lys Ala Thr Glu Leu Lys His Leu Gln Cys Leu Glu Glu Leu Lys
 50                  55                  60
Asn Leu Thr Glu Val Leu Asn Leu Ala Gln Ser Lys Asn Phe His Leu
 65                  70                  75                  80
Arg Pro Arg Asp Leu Ile Ser Asn Ile Asn Val Ile Val Leu Glu Leu
                 85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Ser Gln Ser Ile
                115                 120                 125
Ile Ser Thr Leu Thr
            130

<210> SEQ ID NO 57
<211> LENGTH: 133
<212> TYPE: PRT
<213> ORGANISM: Homo sapiens

<400> SEQUENCE: 57

Ala Pro Ala Ser Ser Ser Thr Lys Lys Thr Gln Leu Gln Leu Glu His
  1               5                  10                  15
Leu Leu Leu Asp Leu Gln Met Ile Leu Asn Gly Ile Asn Asn Tyr Lys
                 20                  25                  30
Asn Pro Lys Leu Thr Arg Met Leu Thr Phe Lys Phe Tyr Met Pro Lys
                 35                  40                  45
Lys Ala Thr Glu Leu Lys His Leu Gln Cys Leu Glu Glu Leu Lys
 50                  55                  60
Asn Leu Ser Glu Val Leu Asn Leu Ala Gln Ser Lys Asn Phe His Leu
 65                  70                  75                  80
Arg Pro Arg Asp Leu Ile Ser Asn Ile Asn Val Ile Val Leu Glu Leu
```

```
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 58
<211> LENGTH: 133
<212> TYPE: PRT
<213> ORGANISM: Homo sapiens

<400> SEQUENCE: 58

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Asn Glu Thr Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
        130

<210> SEQ ID NO 59
<211> LENGTH: 133
<212> TYPE: PRT
<213> ORGANISM: Homo sapiens

<400> SEQUENCE: 59

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Asn Glu Ser Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Ser Gln Ser Ile
        115                 120                 125
Ile Ser Thr Leu Thr
```

-continued

130

<210> SEQ ID NO 60
<211> LENGTH: 133
<212> TYPE: PRT
<213> ORGANISM: Homo sapiens

<400> SEQUENCE: 60

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
    50                  55                  60

Pro Asn Glu Thr Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
    130

<210> SEQ ID NO 61
<211> LENGTH: 133
<212> TYPE: PRT
<213> ORGANISM: Homo sapiens

<400> SEQUENCE: 61

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
    50                  55                  60

Pro Asn Glu Ser Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
    130

<210> SEQ ID NO 62
<211> LENGTH: 133
<212> TYPE: PRT
<213> ORGANISM: Homo sapiens

<400> SEQUENCE: 62

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Asn Val Thr Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 63
<211> LENGTH: 133
<212> TYPE: PRT
<213> ORGANISM: Homo sapiens

<400> SEQUENCE: 63

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Asn Val Ser Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 64
<211> LENGTH: 133
<212> TYPE: PRT
<213> ORGANISM: Homo sapiens

<400> SEQUENCE: 64

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

```
Lys Ala Thr Glu Leu Lys His Leu Gln Cys Leu Glu Glu Leu Lys
        50                  55                  60

Pro Leu Glu Asn Val Thr Asn Leu Ala Gln Ser Lys Asn Phe His Leu
 65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 65
<211> LENGTH: 133
<212> TYPE: PRT
<213> ORGANISM: Homo sapiens

<400> SEQUENCE: 65

Ala Pro Ala Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Asn Val Ser Asn Leu Ala Gln Ser Lys Asn Phe His Leu
 65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 66
<211> LENGTH: 133
<212> TYPE: PRT
<213> ORGANISM: Homo sapiens

<400> SEQUENCE: 66

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Asn Leu Thr Leu Ala Gln Ser Lys Asn Phe His Leu
 65                  70                  75                  80

Arg Pro Arg Asp Leu Ile Ser Asn Ile Asn Val Ile Val Leu Glu Leu
                    85                  90                  95
```

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 67
<211> LENGTH: 133
<212> TYPE: PRT
<213> ORGANISM: Homo sapiens

<400> SEQUENCE: 67

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Asn Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 68
<211> LENGTH: 133
<212> TYPE: PRT
<213> ORGANISM: Homo sapiens

<400> SEQUENCE: 68

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Asn Leu Thr Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 69
<211> LENGTH: 133
<212> TYPE: PRT
<213> ORGANISM: Homo sapiens

<400> SEQUENCE: 69

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Asn Leu Ser Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 70
<211> LENGTH: 133
<212> TYPE: PRT
<213> ORGANISM: Homo sapiens

<400> SEQUENCE: 70

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Thr Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 71
<211> LENGTH: 133
<212> TYPE: PRT
<213> ORGANISM: Homo sapiens

<400> SEQUENCE: 71

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ser Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 72
<211> LENGTH: 133
<212> TYPE: PRT
<213> ORGANISM: Homo sapiens

<400> SEQUENCE: 72

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Thr Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 73
<211> LENGTH: 133
<212> TYPE: PRT
<213> ORGANISM: Homo sapiens

<400> SEQUENCE: 73

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

```
Lys Ala Thr Glu Leu Lys His Leu Gln Cys Leu Glu Glu Leu Lys
 50                  55                  60

Pro Leu Glu Glu Val Leu Asn Leu Ser Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 74
<211> LENGTH: 133
<212> TYPE: PRT
<213> ORGANISM: Homo sapiens

<400> SEQUENCE: 74

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Leu Lys
 50                  55                  60

Pro Leu Glu Glu Val Leu Asn Asn Ala Thr Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 75
<211> LENGTH: 133
<212> TYPE: PRT
<213> ORGANISM: Homo sapiens

<400> SEQUENCE: 75

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Leu Lys
 50                  55                  60

Pro Leu Glu Glu Val Leu Asn Ala Ser Ser Lys Asn Phe His Leu
 65                  70                  75                  80

Arg Pro Arg Asp Leu Ile Ser Asn Ile Asn Val Ile Val Leu Glu Leu
                 85                  90                  95
```

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 76
<211> LENGTH: 133
<212> TYPE: PRT
<213> ORGANISM: Homo sapiens

<400> SEQUENCE: 76

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Asn Ala Thr Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 77
<211> LENGTH: 133
<212> TYPE: PRT
<213> ORGANISM: Homo sapiens

<400> SEQUENCE: 77

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Asn Ala Ser Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 78
<211> LENGTH: 133
<212> TYPE: PRT
<213> ORGANISM: Homo sapiens

<400> SEQUENCE: 78

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Asn Ala Thr Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 79
<211> LENGTH: 133
<212> TYPE: PRT
<213> ORGANISM: Homo sapiens

<400> SEQUENCE: 79

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Asn Ala Ser Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 80
<211> LENGTH: 133
<212> TYPE: PRT
<213> ORGANISM: Homo sapiens

<400> SEQUENCE: 80

Ala Pro Ala Ser Ser Ser Thr Lys Lys Thr Gln Leu Gln Leu Glu His

-continued

```
               1               5                  10                 15
             Leu Leu Leu Asp Leu Gln Met Ile Leu Asn Gly Ile Asn Asn Tyr Lys
                           20                  25                 30

Asn Pro Lys Leu Thr Arg Met Leu Thr Phe Lys Phe Tyr Met Pro Lys
                           35                  40                 45

Lys Ala Thr Glu Leu Lys His Leu Gln Cys Leu Glu Glu Glu Leu Lys
                           50                  55                 60

Pro Leu Glu Glu Val Leu Asn Leu Ala Gln Ser Lys Asn Phe His Leu
              65                70                  75                 80

Arg Pro Arg Asp Leu Ile Ser Asn Ile Asn Val Ile Val Leu Glu Leu
                           85                  90                 95

Lys Gly Ser Glu Thr Thr Phe Met Cys Glu Asn Ala Thr Glu Thr Ala
                           100                 105                110

Thr Ile Val Glu Phe Leu Asn Arg Trp Ile Thr Phe Ser Gln Ser Ile
                           115                 120                125

Ile Ser Thr Leu Thr
                           130

<210> SEQ ID NO 81
<211> LENGTH: 133
<212> TYPE: PRT
<213> ORGANISM: Homo sapiens

<400> SEQUENCE: 81

Ala Pro Ala Ser Ser Thr Lys Lys Thr Gln Leu Gln Leu Glu His
              1                5                  10                 15

Leu Leu Leu Asp Leu Gln Met Ile Leu Asn Gly Ile Asn Asn Tyr Lys
                           20                  25                 30

Asn Pro Lys Leu Thr Arg Met Leu Thr Phe Lys Phe Tyr Met Pro Lys
                           35                  40                 45

Lys Ala Thr Glu Leu Lys His Leu Gln Cys Leu Glu Glu Glu Leu Lys
                           50                  55                 60

Pro Leu Glu Glu Val Leu Asn Leu Ala Gln Ser Lys Asn Phe His Leu
              65                70                  75                 80

Arg Pro Arg Asp Leu Ile Ser Asn Ile Asn Val Ile Val Leu Glu Leu
                           85                  90                 95

Lys Gly Ser Glu Thr Thr Phe Met Cys Glu Asn Ala Ser Glu Thr Ala
                           100                 105                110

Thr Ile Val Glu Phe Leu Asn Arg Trp Ile Thr Phe Ser Gln Ser Ile
                           115                 120                125

Ile Ser Thr Leu Thr
                           130

<210> SEQ ID NO 82
<211> LENGTH: 133
<212> TYPE: PRT
<213> ORGANISM: Homo sapiens

<400> SEQUENCE: 82

Ala Pro Thr Ser Ser Thr Lys Lys Thr Gln Leu Gln Leu Glu His
              1                5                  10                 15

Leu Leu Leu Asp Leu Gln Met Ile Leu Asn Gly Ile Asn Asn Tyr Lys
                           20                  25                 30

Asn Pro Lys Leu Thr Arg Met Leu Thr Phe Lys Phe Tyr Met Pro Lys
                           35                  40                 45

Lys Ala Thr Glu Leu Lys His Leu Gln Cys Leu Glu Glu Glu Leu Lys
```

```
                    50                  55                  60
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asn Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 83
<211> LENGTH: 133
<212> TYPE: PRT
<213> ORGANISM: Homo sapiens

<400> SEQUENCE: 83

Ala Pro Thr Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asn Glu Ser Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 84
<211> LENGTH: 133
<212> TYPE: PRT
<213> ORGANISM: Homo sapiens

<400> SEQUENCE: 84

Ala Pro Ala Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asn Glu Thr Ala
```

```
            100                 105                 110
Thr Ile Val Glu Phe Leu Asn Arg Trp Ile Thr Phe Ser Gln Ser Ile
            115                 120                 125

Ile Ser Thr Leu Thr
    130
```

<210> SEQ ID NO 85
<211> LENGTH: 133
<212> TYPE: PRT
<213> ORGANISM: Homo sapiens

<400> SEQUENCE: 85

```
Ala Pro Ala Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asn Glu Ser Ala
            100                 105                 110

Thr Ile Val Glu Phe Leu Asn Arg Trp Ile Thr Phe Ser Gln Ser Ile
            115                 120                 125

Ile Ser Thr Leu Thr
    130
```

<210> SEQ ID NO 86
<211> LENGTH: 133
<212> TYPE: PRT
<213> ORGANISM: Homo sapiens

<400> SEQUENCE: 86

```
Ala Pro Thr Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Asn Leu Thr Phe Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130
```

```
<210> SEQ ID NO 87
<211> LENGTH: 133
<212> TYPE: PRT
<213> ORGANISM: Homo sapiens

<400> SEQUENCE: 87
```

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Asn Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

```
<210> SEQ ID NO 88
<211> LENGTH: 133
<212> TYPE: PRT
<213> ORGANISM: Homo sapiens

<400> SEQUENCE: 88
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Asn Phe Thr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

```
<210> SEQ ID NO 89
<211> LENGTH: 133
<212> TYPE: PRT
<213> ORGANISM: Homo sapiens

<400> SEQUENCE: 89
```

Ala Pro Ala Ser Ser Ser Thr Lys Lys Thr Gln Leu Gln Leu Glu His
1               5                   10                  15

```
Leu Leu Leu Asp Leu Gln Met Ile Leu Asn Gly Ile Asn Asn Tyr Lys
            20                  25                  30

Asn Pro Lys Leu Thr Asn Met Thr Thr Phe Asn Phe Thr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 90
<211> LENGTH: 133
<212> TYPE: PRT
<213> ORGANISM: Homo sapiens

<400> SEQUENCE: 90

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Ala Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 91
<211> LENGTH: 133
<212> TYPE: PRT
<213> ORGANISM: Homo sapiens

<400> SEQUENCE: 91

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Ala Lys Phe Tyr Met Pro Lys
         35                  40                  45

Lys Ala Thr Glu Leu Lys His Leu Gln Cys Leu Glu Glu Glu Leu Lys
     50                  55                  60
```

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 92
<211> LENGTH: 133
<212> TYPE: PRT
<213> ORGANISM: Homo sapiens

<400> SEQUENCE: 92

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Phe Lys Phe Ala Met Pro Lys
            35                  40                  45

Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 93
<211> LENGTH: 133
<212> TYPE: PRT
<213> ORGANISM: Homo sapiens

<400> SEQUENCE: 93

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Phe Lys Phe Ala Met Pro Lys
            35                  40                  45

Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

-continued

```
Thr Ile Val Glu Phe Leu Asn Arg Trp Ile Thr Phe Ser Gln Ser Ile
            115                 120                 125

Ile Ser Thr Leu Thr
    130

<210> SEQ ID NO 94
<211> LENGTH: 133
<212> TYPE: PRT
<213> ORGANISM: Homo sapiens

<400> SEQUENCE: 94

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Ala Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130

<210> SEQ ID NO 95
<211> LENGTH: 133
<212> TYPE: PRT
<213> ORGANISM: Homo sapiens

<400> SEQUENCE: 95

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Ala Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130

<210> SEQ ID NO 96
```

```
<211> LENGTH: 133
<212> TYPE: PRT
<213> ORGANISM: Homo sapiens

<400> SEQUENCE: 96

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 97
<211> LENGTH: 133
<212> TYPE: PRT
<213> ORGANISM: Homo sapiens

<400> SEQUENCE: 97

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 98
<211> LENGTH: 153
<212> TYPE: PRT
<213> ORGANISM: Homo sapiens

<400> SEQUENCE: 98

Met Tyr Arg Met Gln Leu Leu Ser Cys Ile Ala Leu Ser Leu Ala Leu
1               5                   10                  15
```

```
Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
 50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 99
<211> LENGTH: 551
<212> TYPE: PRT
<213> ORGANISM: Homo sapiens

<400> SEQUENCE: 99

Met Ala Ala Pro Ala Leu Ser Trp Arg Leu Pro Leu Leu Ile Leu Leu
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
 50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
210                 215                 220

Gln Pro Leu Ala Phe Arg Thr Lys Pro Ala Ala Leu Gly Lys Asp Thr
225                 230                 235                 240
```

```
Ile Pro Trp Leu Gly His Leu Val Gly Leu Ser Gly Ala Phe Gly
                245                 250                 255

Phe Ile Ile Leu Val Tyr Leu Ile Asn Cys Arg Asn Thr Gly Pro
            260                 265                 270

Trp Leu Lys Lys Val Leu Lys Cys Asn Thr Pro Asp Pro Ser Lys Phe
        275                 280                 285

Phe Ser Gln Leu Ser Ser Glu His Gly Gly Asp Val Gln Lys Trp Leu
    290                 295                 300

Ser Ser Pro Phe Pro Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe Phe His
        355                 360                 365

Leu Pro Asp Ala Leu Glu Ile Glu Ala Cys Gln Val Tyr Phe Thr Tyr
    370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430

Ser Leu Leu Gly Gly Pro Ser Pro Ser Thr Ala Pro Gly Gly Ser
        435                 440                 445

Gly Ala Gly Glu Glu Arg Met Pro Pro Ser Leu Gln Glu Arg Val Pro
450                 455                 460

Arg Asp Trp Asp Pro Gln Pro Leu Gly Pro Pro Thr Pro Gly Val Pro
465                 470                 475                 480

Asp Leu Val Asp Phe Gln Pro Pro Pro Glu Leu Val Leu Arg Glu Ala
                485                 490                 495

Gly Glu Glu Val Pro Asp Ala Gly Pro Arg Glu Gly Val Ser Phe Pro
            500                 505                 510

Trp Ser Arg Pro Pro Gly Gln Gly Glu Phe Arg Ala Leu Asn Ala Arg
        515                 520                 525

Leu Pro Leu Asn Thr Asp Ala Tyr Leu Ser Leu Gln Glu Leu Gln Gly
    530                 535                 540

Gln Asp Pro Thr His Leu Val
545                 550

<210> SEQ ID NO 100
<211> LENGTH: 369
<212> TYPE: PRT
<213> ORGANISM: Homo sapiens

<400> SEQUENCE: 100

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
                20                  25                  30

Asn Glu Asp Thr Thr Ala Asp Phe Phe Leu Thr Thr Met Pro Thr Asp
            35                  40                  45

Ser Leu Ser Val Ser Thr Leu Pro Leu Pro Glu Val Gln Cys Phe Val
```

```
            50                  55                  60
Phe Asn Val Glu Tyr Met Asn Cys Thr Trp Asn Ser Ser Glu Pro
 65                  70                  75                  80

Gln Pro Thr Asn Leu Thr Leu His Tyr Trp Tyr Lys Asn Ser Asp Asn
                 85                  90                  95

Asp Lys Val Gln Lys Cys Ser His Tyr Leu Phe Ser Glu Glu Ile Thr
                100                 105                 110

Ser Gly Cys Gln Leu Gln Lys Lys Glu Ile His Leu Tyr Gln Thr Phe
            115                 120                 125

Val Val Gln Leu Gln Asp Pro Arg Glu Pro Arg Arg Gln Ala Thr Gln
130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
            195                 200                 205

Ser Leu Pro Ser Val Asp Gly Gln Lys Arg Tyr Thr Phe Arg Val Arg
210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
            275                 280                 285

Arg Ile Pro Thr Leu Lys Asn Leu Glu Asp Leu Val Thr Glu Tyr His
            290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
            355                 360                 365
Thr
```

```
<210> SEQ ID NO 101
<211> LENGTH: 8
<212> TYPE: PRT
<213> ORGANISM: Artificial Sequence
<220> FEATURE:
<223> OTHER INFORMATION: Synthesized

<400> SEQUENCE: 101

Gly Ser Thr Trp Ser Ile Asn Thr
 1               5

<210> SEQ ID NO 102
<211> LENGTH: 7
<212> TYPE: PRT
<213> ORGANISM: Artificial Sequence
```

```
<220> FEATURE:
<223> OTHER INFORMATION: Synthesized

<400> SEQUENCE: 102

Ile Ser Ser Gly Gly Ser Thr
1               5

<210> SEQ ID NO 103
<211> LENGTH: 10
<212> TYPE: PRT
<213> ORGANISM: Artificial Sequence
<220> FEATURE:
<223> OTHER INFORMATION: Synthesized

<400> SEQUENCE: 103

Tyr Ala Gln Ser Thr Trp Tyr Pro Pro Ser
1               5                   10

<210> SEQ ID NO 104
<211> LENGTH: 25
<212> TYPE: PRT
<213> ORGANISM: Artificial Sequence
<220> FEATURE:
<223> OTHER INFORMATION: Synthesized

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 105
<211> LENGTH: 17
<212> TYPE: PRT
<213> ORGANISM: Artificial Sequence
<220> FEATURE:
<223> OTHER INFORMATION: Synthesized

<400> SEQUENCE: 105

Leu Ala Trp Tyr Arg Gln Ala Pro Gly Lys Gln Arg Asp Leu Val Ala
1               5                   10                  15

Arg

<210> SEQ ID NO 106
<211> LENGTH: 38
<212> TYPE: PRT
<213> ORGANISM: Artificial Sequence
<220> FEATURE:
<223> OTHER INFORMATION: Synthesized

<400> SEQUENCE: 106

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 107
<211> LENGTH: 11
<212> TYPE: PRT
<213> ORGANISM: Artificial Sequence
<220> FEATURE:
<223> OTHER INFORMATION: Synthesized
```

<400> SEQUENCE: 107

Ser Gly Gln Gly Thr Gln Val Thr Val Ser Ser
1               5                   10

<210> SEQ ID NO 108
<211> LENGTH: 116
<212> TYPE: PRT
<213> ORGANISM: Artificial Sequence
<220> FEATURE:
<223> OTHER INFORMATION: Synthesized

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Trp Ser Ile Asn
            20                  25                  30

Thr Leu Ala Trp Tyr Arg Gln Ala Pro Gly Lys Gln Arg Asp Leu Val
        35                  40                  45

Ala Arg Ile Ser Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Tyr
                85                  90                  95

Ala Gln Ser Thr Trp Tyr Pro Pro Ser Trp Gly Gln Gly Thr Leu Val
            100                 105                 110

Thr Val Ser Ser
        115

<210> SEQ ID NO 109
<211> LENGTH: 8
<212> TYPE: PRT
<213> ORGANISM: Artificial Sequence
<220> FEATURE:
<223> OTHER INFORMATION: Synthesized

<400> SEQUENCE: 109

Gly Phe Ala Phe Arg Gly Phe Gly
1               5

<210> SEQ ID NO 110
<211> LENGTH: 8
<212> TYPE: PRT
<213> ORGANISM: Artificial Sequence
<220> FEATURE:
<223> OTHER INFORMATION: Synthesized

<400> SEQUENCE: 110

Ile Asn Asn Gly Gly Ser Asp Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Synthesized

<400> SEQUENCE: 111

Ala Ile Gly Gly Pro Gly Ala Ser Pro
1               5

<210> SEQ ID NO 112
<211> LENGTH: 25
<212> TYPE: PRT
<213> ORGANISM: Artificial Sequence
<220> FEATURE:
<223> OTHER INFORMATION: Synthesized

<400> SEQUENCE: 112

Gln Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 113
<211> LENGTH: 17
<212> TYPE: PRT
<213> ORGANISM: Artificial Sequence
<220> FEATURE:
<223> OTHER INFORMATION: Synthesized

<400> SEQUENCE: 113

Met Ser Trp Val Arg Gln Ala Pro Gly Lys Gly Leu Glu Trp Val Ser
1               5                   10                  15

Ser

<210> SEQ ID NO 114
<211> LENGTH: 11
<212> TYPE: PRT
<213> ORGANISM: Artificial Sequence
<220> FEATURE:
<223> OTHER INFORMATION: Synthesized

<400> SEQUENCE: 114

Ser Gly Gln Gly Thr Gln Val Thr Val Ser Ser
1               5                   10

<210> SEQ ID NO 115
<211> LENGTH: 116
<212> TYPE: PRT
<213> ORGANISM: Artificial Sequence
<220> FEATURE:
<223> OTHER INFORMATION: Synthesized

<400> SEQUENCE: 115

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Ala Phe Arg Gly Phe
            20                  25                  30

Gly Met Ser Trp Val Arg Gln Ala Pro Gly Lys Gly Leu Glu Trp Val
        35                  40                  45

Ser Ser Ile Asn Asn Gly Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Gly Gly Pro Gly Ala Ser Pro Ser Gly Gln Gly Thr Gln Val
            100                 105                 110

Thr Val Ser Ser
        115

<210> SEQ ID NO 116

```
<211> LENGTH: 227
<212> TYPE: PRT
<213> ORGANISM: Homo sapiens

<400> SEQUENCE: 116

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 117
<211> LENGTH: 227
<212> TYPE: PRT
<213> ORGANISM: Homo sapiens

<400> SEQUENCE: 117

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 118
<211> LENGTH: 227
<212> TYPE: PRT
<213> ORGANISM: Homo sapiens

<400> SEQUENCE: 118

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225
```

<210> SEQ ID NO 119
<211> LENGTH: 227
<212> TYPE: PRT
<213> ORGANISM: Homo sapiens

<400> SEQUENCE: 119

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 120
<211> LENGTH: 227
<212> TYPE: PRT
<213> ORGANISM: Homo sapiens

<400> SEQUENCE: 120

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile

```
              100                 105                 110
Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 121
<211> LENGTH: 227
<212> TYPE: PRT
<213> ORGANISM: Homo sapiens

<400> SEQUENCE: 121

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225
```

```
<210> SEQ ID NO 122
<211> LENGTH: 228
<212> TYPE: PRT
<213> ORGANISM: Homo sapiens

<400> SEQUENCE: 122

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 123
<211> LENGTH: 229
<212> TYPE: PRT
<213> ORGANISM: Homo sapiens

<400> SEQUENCE: 123

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95
```

-continued

```
Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 124
<211> LENGTH: 6
<212> TYPE: PRT
<213> ORGANISM: Artificial Sequence
<220> FEATURE:
<223> OTHER INFORMATION: Synthesized

<400> SEQUENCE: 124

```
Gly Ser Gly Gly Ser Gly
1               5
```

<210> SEQ ID NO 125
<211> LENGTH: 9
<212> TYPE: PRT
<213> ORGANISM: Artificial Sequence
<220> FEATURE:
<223> OTHER INFORMATION: Synthesized

<400> SEQUENCE: 125

```
Gly Ser Gly Gly Ser Gly Gly Ser Gly
1               5
```

<210> SEQ ID NO 126
<211> LENGTH: 12
<212> TYPE: PRT
<213> ORGANISM: Artificial Sequence
<220> FEATURE:
<223> OTHER INFORMATION: Synthesized

<400> SEQUENCE: 126

```
Gly Ser Gly Gly Ser Gly Gly Ser Gly Gly Ser Gly
1               5                   10
```

<210> SEQ ID NO 127
<211> LENGTH: 4
<212> TYPE: PRT
<213> ORGANISM: Artificial Sequence
<220> FEATURE:
<223> OTHER INFORMATION: Synthesized

<400> SEQUENCE: 127

```
Gly Gly Gly Ser
1
```

```
<210> SEQ ID NO 128
<211> LENGTH: 8
<212> TYPE: PRT
<213> ORGANISM: Artificial Sequence
<220> FEATURE:
<223> OTHER INFORMATION: Synthesized

<400> SEQUENCE: 128

Gly Gly Gly Ser Gly Gly Gly Ser
1               5

<210> SEQ ID NO 129
<211> LENGTH: 12
<212> TYPE: PRT
<213> ORGANISM: Artificial Sequence
<220> FEATURE:
<223> OTHER INFORMATION: Synthesized

<400> SEQUENCE: 129

Gly Gly Gly Ser Gly Gly Gly Ser Gly Gly Gly Ser
1               5                   10

<210> SEQ ID NO 130
<211> LENGTH: 16
<212> TYPE: PRT
<213> ORGANISM: Artificial Sequence
<220> FEATURE:
<223> OTHER INFORMATION: Synthesized

<400> SEQUENCE: 130

Gly Gly Gly Ser Gly Gly Gly Ser Gly Gly Gly Ser Gly Gly Gly Ser
1               5                   10                  15

<210> SEQ ID NO 131
<211> LENGTH: 5
<212> TYPE: PRT
<213> ORGANISM: Artificial Sequence
<220> FEATURE:
<223> OTHER INFORMATION: Synthesized

<400> SEQUENCE: 131

Gly Gly Gly Gly Ser
1               5

<210> SEQ ID NO 132
<211> LENGTH: 10
<212> TYPE: PRT
<213> ORGANISM: Artificial Sequence
<220> FEATURE:
<223> OTHER INFORMATION: Synthesized

<400> SEQUENCE: 132

Gly Gly Gly Gly Ser Gly Gly Gly Gly Ser
1               5                   10

<210> SEQ ID NO 133
<211> LENGTH: 15
<212> TYPE: PRT
<213> ORGANISM: Artificial Sequence
<220> FEATURE:
<223> OTHER INFORMATION: Synthesized

<400> SEQUENCE: 133

Gly Gly Gly Gly Ser Gly Gly Gly Gly Ser Gly Gly Gly Gly Ser
1               5                   10                  15
```

```
<210> SEQ ID NO 134
<211> LENGTH: 20
<212> TYPE: PRT
<213> ORGANISM: Artificial Sequence
<220> FEATURE:
<223> OTHER INFORMATION: Synthesized

<400> SEQUENCE: 134

Gly Gly Gly Gly Ser Gly Gly Gly Ser Gly Gly Gly Gly Ser Gly
1               5                   10                  15

Gly Gly Gly Ser
            20

<210> SEQ ID NO 135
<211> LENGTH: 4
<212> TYPE: PRT
<213> ORGANISM: Artificial Sequence
<220> FEATURE:
<223> OTHER INFORMATION: Synthesized

<400> SEQUENCE: 135

Ser Gly Ser Gly
1

<210> SEQ ID NO 136
<211> LENGTH: 7
<212> TYPE: PRT
<213> ORGANISM: Artificial Sequence
<220> FEATURE:
<223> OTHER INFORMATION: Synthesized

<400> SEQUENCE: 136

Ser Gly Ser Gly Gly Ser Gly
1               5

<210> SEQ ID NO 137
<211> LENGTH: 10
<212> TYPE: PRT
<213> ORGANISM: Artificial Sequence
<220> FEATURE:
<223> OTHER INFORMATION: Synthesized

<400> SEQUENCE: 137

Ser Gly Ser Gly Gly Ser Gly Gly Ser Gly
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Synthesized

<400> SEQUENCE: 138

Ser Gly Ser Gly Gly Ser Gly Gly Ser Gly Gly Ser Gly
1               5                   10

<210> SEQ ID NO 139
<211> LENGTH: 5
<212> TYPE: PRT
<213> ORGANISM: Artificial Sequence
<220> FEATURE:
<223> OTHER INFORMATION: Synthesized

<400> SEQUENCE: 139

Ser Gly Gly Gly Ser
1               5
```

```
<210> SEQ ID NO 140
<211> LENGTH: 9
<212> TYPE: PRT
<213> ORGANISM: Artificial Sequence
<220> FEATURE:
<223> OTHER INFORMATION: Synthesized

<400> SEQUENCE: 140

Ser Gly Gly Gly Ser Gly Gly Gly Ser
1               5

<210> SEQ ID NO 141
<211> LENGTH: 13
<212> TYPE: PRT
<213> ORGANISM: Artificial Sequence
<220> FEATURE:
<223> OTHER INFORMATION: Synthesized

<400> SEQUENCE: 141

Ser Gly Gly Gly Ser Gly Gly Gly Ser Gly Gly Gly Ser
1               5                   10

<210> SEQ ID NO 142
<211> LENGTH: 17
<212> TYPE: PRT
<213> ORGANISM: Artificial Sequence
<220> FEATURE:
<223> OTHER INFORMATION: Synthesized

<400> SEQUENCE: 142

Ser Gly Gly Gly Ser Gly Gly Gly Ser Gly Gly Gly Ser Gly Gly Gly
1               5                   10                  15

Ser

<210> SEQ ID NO 143
<211> LENGTH: 6
<212> TYPE: PRT
<213> ORGANISM: Artificial Sequence
<220> FEATURE:
<223> OTHER INFORMATION: Synthesized

<400> SEQUENCE: 143

Ser Gly Gly Gly Gly Ser
1               5

<210> SEQ ID NO 144
<211> LENGTH: 11
<212> TYPE: PRT
<213> ORGANISM: Artificial Sequence
<220> FEATURE:
<223> OTHER INFORMATION: Synthesized

<400> SEQUENCE: 144

Ser Gly Gly Gly Gly Ser Gly Gly Gly Gly Ser
1               5                   10

<210> SEQ ID NO 145
<211> LENGTH: 16
<212> TYPE: PRT
<213> ORGANISM: Artificial Sequence
<220> FEATURE:
<223> OTHER INFORMATION: Synthesized

<400> SEQUENCE: 145

Ser Gly Gly Gly Gly Ser Gly Gly Gly Gly Ser Gly Gly Gly Gly Ser
```

-continued

```
1               5                   10                  15

<210> SEQ ID NO 146
<211> LENGTH: 21
<212> TYPE: PRT
<213> ORGANISM: Artificial Sequence
<220> FEATURE:
<223> OTHER INFORMATION: Synthesized

<400> SEQUENCE: 146

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 147
<211> LENGTH: 5
<212> TYPE: PRT
<213> ORGANISM: Artificial Sequence
<220> FEATURE:
<223> OTHER INFORMATION: Synthesized

<400> SEQUENCE: 147

Glu Ala Ala Ala Lys
1               5

<210> SEQ ID NO 148
<211> LENGTH: 10
<212> TYPE: PRT
<213> ORGANISM: Artificial Sequence
<220> FEATURE:
<223> OTHER INFORMATION: Synthesized

<400> SEQUENCE: 148

Glu Ala Ala Ala Lys Glu Ala Ala Ala Lys
1               5                   10

<210> SEQ ID NO 149
<211> LENGTH: 15
<212> TYPE: PRT
<213> ORGANISM: Artificial Sequence
<220> FEATURE:
<223> OTHER INFORMATION: Synthesized

<400> SEQUENCE: 149

Glu Ala Ala Ala Lys Glu Ala Ala Ala Lys Glu Ala Ala Ala Lys
1               5                   10                  15

<210> SEQ ID NO 150
<211> LENGTH: 20
<212> TYPE: PRT
<213> ORGANISM: Artificial Sequence
<220> FEATURE:
<223> OTHER INFORMATION: Synthesized

<400> SEQUENCE: 150

Glu Ala Ala Ala Lys Glu Ala Ala Ala Lys Glu Ala Ala Ala Lys Glu
1               5                   10                  15

Ala Ala Ala Lys
            20

<210> SEQ ID NO 151
<211> LENGTH: 5
<212> TYPE: PRT
<213> ORGANISM: Artificial Sequence
<220> FEATURE:
```

```
<223> OTHER INFORMATION: Synthesized

<400> SEQUENCE: 151

Pro Ala Pro Ala Pro
1               5

<210> SEQ ID NO 152
<211> LENGTH: 10
<212> TYPE: PRT
<213> ORGANISM: Artificial Sequence
<220> FEATURE:
<223> OTHER INFORMATION: Synthesized

<400> SEQUENCE: 152

Pro Ala Pro Ala Pro Pro Ala Pro Ala Pro
1               5                   10

<210> SEQ ID NO 153
<211> LENGTH: 15
<212> TYPE: PRT
<213> ORGANISM: Artificial Sequence
<220> FEATURE:
<223> OTHER INFORMATION: Synthesized

<400> SEQUENCE: 153

Pro Ala Pro Ala Pro Pro Ala Pro Ala Pro Pro Ala Pro Ala Pro
1               5                   10                  15

<210> SEQ ID NO 154
<211> LENGTH: 20
<212> TYPE: PRT
<213> ORGANISM: Artificial Sequence
<220> FEATURE:
<223> OTHER INFORMATION: Synthesized

<400> SEQUENCE: 154

Pro Ala Pro Ala Pro Pro Ala Pro Ala Pro Pro Ala Pro Ala Pro Pro
1               5                   10                  15

Ala Pro Ala Pro
            20

<210> SEQ ID NO 155
<211> LENGTH: 8
<212> TYPE: PRT
<213> ORGANISM: Artificial Sequence
<220> FEATURE:
<223> OTHER INFORMATION: Synthesized

<400> SEQUENCE: 155

Ile Lys Arg Thr Val Ala Ala Pro
1               5

<210> SEQ ID NO 156
<211> LENGTH: 133
<212> TYPE: PRT
<213> ORGANISM: Homo sapiens

<400> SEQUENCE: 156

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45
```

```
Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser
        130

<210> SEQ ID NO 157
<211> LENGTH: 133
<212> TYPE: PRT
<213> ORGANISM: Homo sapiens

<400> SEQUENCE: 157

Gln Gly Gln Asp Glu His Met Ile Arg Met Arg Gln Leu Ile Asp Ile
 1               5                  10                  15

Val Asp Gln Leu Lys Asn Tyr Val Asn Asp Leu Val Pro Glu Phe Leu
                 20                  25                  30

Pro Ala Pro Glu Asp Val Glu Thr Asn Cys Glu Trp Ser Ala Phe Ser
             35                  40                  45

Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser
        130

<210> SEQ ID NO 158
<211> LENGTH: 123
<212> TYPE: PRT
<213> ORGANISM: Homo sapiens

<400> SEQUENCE: 158

Gln Gly Gln Asp Arg His Met Ile Arg Met Arg Gln Leu Ile Asp Ile
 1               5                  10                  15

Val Asp Gln Leu Lys Asn Tyr Val Asn Asp Leu Val Pro Glu Phe Leu
                 20                  25                  30

Pro Ala Pro Glu Asp Val Glu Thr Asn Cys Glu Trp Ser Ala Phe Ser
             35                  40                  45

Cys Phe Gln Lys Ala Gln Leu Lys Ser Ala Asn Thr Gly Asn Asn Glu
 50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95
```

-continued

```
Asp Ser Tyr Glu Lys Lys Pro Pro Lys Glu Phe Leu Glu Arg Phe Lys
            100                 105                 110

Ser Leu Leu Gln Lys Met Ile His Gln His Leu
            115                 120

<210> SEQ ID NO 159
<211> LENGTH: 394
<212> TYPE: PRT
<213> ORGANISM: Homo sapiens

<400> SEQUENCE: 159

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
            115                 120                 125

Gly Ser Glu Asp Ser Glu Val Gln Leu Val Glu Ser Gly Gly Gly Leu
        130                 135                 140

Val Gln Pro Gly Gly Ser Leu Arg Leu Ser Cys Ala Ala Ser Gly Ser
145                 150                 155                 160

Thr Trp Ser Ile Asn Thr Leu Ala Trp Tyr Arg Gln Ala Pro Gly Lys
                165                 170                 175

Gln Arg Asp Leu Val Ala Arg Ile Ser Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Tyr Ala Gln Ser Thr Trp Tyr Pro Pro Ser Trp Gly
225                 230                 235                 240

Gln Gly Thr Leu Val Thr Val Ser Ser Gly Ser Gly Gly Ser Gly Gly
                245                 250                 255

Ser Gly Gly Ser Gly Ala Pro Thr Ser Ser Ser Thr Lys Lys Thr Gln
            260                 265                 270

Leu Gln Leu Glu His Leu Leu Leu Asp Leu Gln Met Ile Leu Asn Gly
        275                 280                 285

Ile Asn Asn Tyr Lys Asn Pro Lys Leu Thr Arg Met Leu Thr Phe Lys
    290                 295                 300

Phe Tyr Met Pro Lys Lys Ala Thr Glu Leu Lys His Leu Gln Cys Leu
305                 310                 315                 320

Glu Glu Glu Leu Lys Pro Leu Glu Glu Val Leu Asn Leu Ala Gln Ser
                325                 330                 335

Lys Asn Phe His Leu Arg Pro Arg Asp Leu Ile Ser Asn Ile Asn Val
            340                 345                 350
```

-continued

Ile Val Leu Glu Leu Lys Gly Ser Glu Thr Thr Phe Met Cys Glu Tyr
            355                 360                 365

Ala Asp Glu Thr Ala Thr Ile Val Glu Phe Leu Asn Arg Trp Ile Thr
        370                 375                 380

Phe Ser Gln Ser Ile Ile Ser Thr Leu Thr
385                 390

<210> SEQ ID NO 160
<211> LENGTH: 394
<212> TYPE: PRT
<213> ORGANISM: Homo sapiens

<400> SEQUENCE: 160

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser
    130                 135                 140

Gly Glu Val Gln Leu Val Glu Ser Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Ser Trp Gly Gln Gly Thr Leu
                245                 250                 255

Val Thr Val Ser Ser Gln Gly Gln Asp Arg His Met Ile Arg Met Arg
            260                 265                 270

Gln Leu Ile Asp Ile Val Asp Gln Leu Lys Asn Tyr Val Asn Asp Leu
        275                 280                 285

Val Pro Glu Phe Leu Pro Ala Pro Glu Asp Val Glu Thr Asn Cys Glu
    290                 295                 300

Trp Ser Ala Phe Ser Cys Phe Gln Lys Ala Gln Leu Lys Ser Ala Asn
305                 310                 315                 320

Thr Gly Asn Asn Glu Arg Ile Ile Asn Val Ser Ile Lys Lys Leu Lys

```
                    325                 330                 335
Arg Lys Pro Pro Ser Thr Asn Ala Gly Arg Arg Gln Lys His Arg Leu
                340                 345                 350

Thr Cys Pro Ser Cys Asp Ser Tyr Glu Lys Lys Pro Pro Lys Glu Phe
            355                 360                 365

Leu Glu Arg Phe Lys Ser Leu Leu Gln Lys Met Ile His Gln His Leu
        370                 375                 380

Ser Ser Arg Thr His Gly Ser Glu Asp Ser
385                 390

<210> SEQ ID NO 161
<211> LENGTH: 394
<212> TYPE: PRT
<213> ORGANISM: Homo sapiens

<400> SEQUENCE: 161

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Glu Val Gln Leu Val Glu Ser Gly Gly Gly Leu
    130                 135                 140

Val Gln Pro Gly Gly Ser Leu Arg Leu Ser Cys Ala Ala Ser Gly Ser
145                 150                 155                 160

Thr Trp Ser Ile Asn Thr Leu Ala Trp Tyr Arg Gln Ala Pro Gly Lys
                165                 170                 175

Gln Arg Asp Leu Val Ala Arg Ile Ser Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Tyr Ala Gln Ser Thr Trp Tyr Pro Pro Ser Trp Gly
225                 230                 235                 240

Gln Gly Thr Leu Val Thr Val Ser Ser Gly Ser Gly Gly Ser Gly Gly
                245                 250                 255

Ser Gly Gly Ser Gly Ala Pro Ala Ser Ser Ser Thr Lys Lys Thr Gln
            260                 265                 270

Leu Gln Leu Glu His Leu Leu Leu Asp Leu Gln Met Ile Leu Asn Gly
        275                 280                 285

Ile Asn Asn Tyr Lys Asn Pro Lys Leu Thr Asn Met Thr Thr Phe Lys
    290                 295                 300
```

-continued

```
Phe Tyr Met Pro Lys Lys Ala Thr Glu Leu Lys His Leu Gln Cys Leu
305                 310                 315                 320

Glu Glu Glu Leu Lys Pro Leu Glu Glu Val Leu Asn Leu Ala Gln Ser
            325                 330                 335

Lys Asn Phe His Leu Arg Pro Arg Asp Leu Ile Ser Asn Ile Asn Val
        340                 345                 350

Ile Val Leu Glu Leu Lys Gly Ser Glu Thr Thr Phe Met Cys Glu Tyr
    355                 360                 365

Ala Asp Glu Thr Ala Thr Ile Val Glu Phe Leu Asn Arg Trp Ile Thr
370                 375                 380

Phe Ser Gln Ser Ile Ile Ser Thr Leu Thr
385                 390

<210> SEQ ID NO 162
<211> LENGTH: 394
<212> TYPE: PRT
<213> ORGANISM: Homo sapiens

<400> SEQUENCE: 162

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser Gly Gly Ser
130                 135                 140

Gly Glu Val Gln Leu Val Glu Ser Gly Gly Gly Leu Val Gln Pro Gly
145                 150                 155                 160

Gly Ser Leu Arg Leu Ser Cys Ala Ala Ser Gly Ser Thr Trp Ser Ile
                165                 170                 175

Asn Thr Leu Ala Trp Tyr Arg Gln Ala Pro Gly Lys Gln Arg Asp Leu
            180                 185                 190

Val Ala Arg Ile Ser Ser Gly Gly Ser Thr Tyr Tyr Ala Asp Ser Val
        195                 200                 205

Lys Gly Arg Phe Thr Ile Ser Arg Asp Asn Ser Lys Asn Thr Leu Tyr
210                 215                 220

Leu Gln Met Asn Ser Leu Arg Ala Glu Asp Thr Ala Val Tyr Tyr Cys
225                 230                 235                 240

Tyr Ala Gln Ser Thr Trp Tyr Pro Pro Ser Trp Gly Gln Gly Thr Leu
                245                 250                 255

Val Thr Val Ser Ser Gln Gly Gln Asp Glu His Met Ile Arg Met Arg
            260                 265                 270

Gln Leu Ile Asp Ile Val Asp Gln Leu Lys Asn Tyr Val Asn Asp Leu
        275                 280                 285
```

```
Val Pro Glu Phe Leu Pro Ala Pro Glu Asp Val Glu Thr Asn Cys Glu
    290                 295                 300

Trp Ser Ala Phe Ser Cys Phe Gln Lys Ala Gln Leu Lys Ser Ala Asn
305                 310                 315                 320

Thr Gly Asn Asn Glu Arg Ile Ile Asn Val Ser Ile Lys Lys Leu Lys
                325                 330                 335

Arg Lys Pro Pro Ser Thr Asn Ala Gly Arg Arg Gln Lys His Arg Leu
                340                 345                 350

Thr Cys Pro Ser Cys Asp Ser Tyr Glu Lys Lys Pro Pro Lys Glu Phe
                355                 360                 365

Leu Glu Arg Phe Lys Ser Leu Leu Gln Lys Met Ile His Gln His Leu
            370                 375                 380

Ser Ser Arg Thr His Gly Ser Glu Asp Ser
385                 390
```

<210> SEQ ID NO 163
<211> LENGTH: 394
<212> TYPE: PRT
<213> ORGANISM: Homo sapiens

<400> SEQUENCE: 163

```
Gln Gly Gln Asp Glu His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Glu Val Gln Leu Val Glu Ser Gly Gly Gly Leu
130                 135                 140

Val Gln Pro Gly Gly Ser Leu Arg Leu Ser Cys Ala Ala Ser Gly Ser
145                 150                 155                 160

Thr Trp Ser Ile Asn Thr Leu Ala Trp Tyr Arg Gln Ala Pro Gly Lys
                165                 170                 175

Gln Arg Asp Leu Val Ala Arg Ile Ser Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Tyr Ala Gln Ser Thr Trp Tyr Pro Pro Ser Trp Gly
225                 230                 235                 240

Gln Gly Thr Leu Val Thr Val Ser Ser Gly Gly Gly Ser Gly Gly Gly
                245                 250                 255

Ser Gly Gly Ser Gly Ala Pro Ala Ser Ser Ser Thr Lys Lys Thr Gln
```

```
                 260              265              270
Leu Gln Leu Glu His Leu Leu Leu Asp Leu Gln Met Ile Leu Asn Gly
            275              280              285

Ile Asn Asn Tyr Lys Asn Pro Lys Leu Thr Asn Met Thr Thr Phe Lys
290              295              300

Phe Tyr Met Pro Lys Lys Ala Thr Glu Leu Lys His Leu Gln Cys Leu
305              310              315              320

Glu Glu Glu Leu Lys Pro Leu Glu Val Leu Asn Leu Ala Gln Ser
            325              330              335

Lys Asn Phe His Leu Arg Pro Arg Asp Leu Ile Ser Asn Ile Asn Val
            340              345              350

Ile Val Leu Glu Leu Lys Gly Ser Glu Thr Thr Phe Met Cys Glu Tyr
            355              360              365

Ala Asp Glu Thr Ala Thr Ile Val Glu Phe Leu Asn Arg Trp Ile Thr
            370              375              380

Phe Ser Gln Ser Ile Ile Ser Thr Leu Thr
385              390
```

<210> SEQ ID NO 164
<211> LENGTH: 413
<212> TYPE: PRT
<213> ORGANISM: Homo sapiens

<400> SEQUENCE: 164

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His Gly Ser Gly Gly Ser Gly Gly Ser
145                 150                 155                 160

Gly Gly Ser Gly Glu Val Gln Leu Val Glu Ser Gly Gly Leu Val
                165                 170                 175

Gln Pro Gly Gly Ser Leu Arg Leu Ser Cys Ala Ala Ser Gly Ser Thr
            180                 185                 190

Trp Ser Ile Asn Thr Leu Ala Trp Tyr Arg Gln Ala Pro Gly Lys Gln
        195                 200                 205

Arg Asp Leu Val Ala Arg Ile Ser Gly Gly Ser Thr Tyr Tyr Ala
    210                 215                 220

Asp Ser Val Lys Gly Arg Phe Thr Ile Ser Arg Asp Asn Ser Lys Asn
225                 230                 235                 240
```

```
Thr Leu Tyr Leu Gln Met Asn Ser Leu Arg Ala Glu Asp Thr Ala Val
                245                 250                 255

Tyr Tyr Cys Tyr Ala Gln Ser Thr Trp Tyr Pro Pro Ser Trp Gly Gln
            260                 265                 270

Gly Thr Leu Val Thr Val Ser Ser Gln Gly Gln Asp Glu His Met Ile
        275                 280                 285

Arg Met Arg Gln Leu Ile Asp Ile Val Asp Gln Leu Lys Asn Tyr Val
290                 295                 300

Asn Asp Leu Val Pro Glu Phe Leu Pro Ala Pro Glu Asp Val Glu Thr
305                 310                 315                 320

Asn Cys Glu Trp Ser Ala Phe Ser Cys Phe Gln Lys Ala Gln Leu Lys
            325                 330                 335

Ser Ala Asn Thr Gly Asn Asn Glu Arg Ile Ile Asn Val Ser Ile Lys
                340                 345                 350

Lys Leu Lys Arg Lys Pro Pro Ser Thr Asn Ala Gly Arg Arg Gln Lys
            355                 360                 365

His Arg Leu Thr Cys Pro Ser Cys Asp Ser Tyr Glu Lys Lys Pro Pro
            370                 375                 380

Lys Glu Phe Leu Glu Arg Phe Lys Ser Leu Leu Gln Lys Met Ile His
385                 390                 395                 400

Gln His Leu Ser Ser Arg Thr His Gly Ser Glu Asp Ser
                405                 410

<210> SEQ ID NO 165
<211> LENGTH: 413
<212> TYPE: PRT
<213> ORGANISM: Homo sapiens

<400> SEQUENCE: 165

Gln Gly Gln Asp Glu His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Glu Val Gln Leu Val Gln Ser Gly Gly Gly Leu
    130                 135                 140

Val Gln Pro Gly Gly Ser Leu Arg Leu Ser Cys Ala Ala Ser Gly Ser
145                 150                 155                 160

Thr Trp Ser Ile Asn Thr Leu Ala Trp Tyr Arg Gln Ala Pro Gly Lys
                165                 170                 175

Gln Arg Asp Leu Val Ala Arg Ile Ser Ser Gly Gly Ser Thr Tyr Tyr
            180                 185                 190

Ala Asp Ser Val Lys Gly Arg Phe Thr Ile Ser Arg Asp Asn Ser Lys
        195                 200                 205
```

```
Asn Thr Leu Tyr Leu Gln Met Asn Ser Leu Arg Ala Glu Asp Thr Ala
            210                 215                 220

Val Tyr Tyr Cys Tyr Ala Gln Ser Thr Trp Tyr Pro Pro Ser Trp Gly
225                 230                 235                 240

Gln Gly Thr Leu Val Thr Val Ser Ser Gly Gly Gly Ser Gly Gly Gly
                    245                 250                 255

Ser Gly Gly Ser Gly Asp Cys Asp Ile Glu Gly Lys Asp Gly Lys Gln
                260                 265                 270

Tyr Glu Ser Val Leu Met Val Ser Ile Asp Gln Leu Leu Asp Ser Met
            275                 280                 285

Lys Glu Ile Gly Ser Asn Cys Leu Asn Asn Glu Phe Asn Phe Lys
290                 295                 300

Arg His Ile Cys Asp Ala Asn Lys Glu Gly Met Phe Leu Phe Arg Ala
305                 310                 315                 320

Ala Arg Lys Leu Arg Gln Phe Leu Lys Met Asn Ser Thr Gly Asp Phe
                    325                 330                 335

Asp Leu His Leu Leu Lys Val Ser Glu Gly Thr Thr Ile Leu Leu Asn
                340                 345                 350

Cys Thr Gly Gln Val Lys Gly Arg Lys Pro Ala Ala Leu Gly Glu Ala
            355                 360                 365

Gln Pro Thr Lys Ser Leu Glu Glu Asn Lys Ser Leu Lys Glu Gln Lys
370                 375                 380

Lys Leu Asn Asp Leu Cys Phe Leu Lys Arg Leu Leu Gln Glu Ile Lys
385                 390                 395                 400

Thr Cys Trp Asn Lys Ile Leu Met Gly Thr Lys Glu His
                    405                 410

<210> SEQ ID NO 166
<211> LENGTH: 394
<212> TYPE: PRT
<213> ORGANISM: Homo sapiens

<400> SEQUENCE: 166

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Gly Gly Ser
        130                 135                 140

Gly Gln Val Gln Leu Val Glu Ser Gly Gly Gly Val Val Gln Pro Gly
145                 150                 155                 160

Gly Ser Leu Arg Leu Ser Cys Ala Ala Ser Gly Phe Ala Phe Arg Gly
```

```
            165                 170                 175
Phe Gly Met Ser Trp Val Arg Gln Ala Pro Gly Lys Gly Leu Glu Trp
            180                 185                 190

Val Ser Ser Ile Asn Asn Gly Gly Ser Asp Thr Tyr Tyr Ala Asp Ser
            195                 200                 205

Val Lys Gly Arg Phe Thr Ile Ser Arg Asp Asn Ser Lys Asn Thr Leu
        210                 215                 220

Tyr Leu Gln Met Asn Ser Leu Arg Ala Glu Asp Thr Ala Val Tyr Tyr
225                 230                 235                 240

Cys Ala Ile Gly Gly Pro Gly Ala Ser Pro Ser Gly Gln Gly Thr Gln
                245                 250                 255

Val Thr Val Ser Ser Gln Gly Gln Asp Arg His Met Ile Arg Met Arg
            260                 265                 270

Gln Leu Ile Asp Ile Val Asp Gln Leu Lys Asn Tyr Val Asn Asp Leu
                275                 280                 285

Val Pro Glu Phe Leu Pro Ala Pro Glu Asp Val Glu Thr Asn Cys Glu
        290                 295                 300

Trp Ser Ala Phe Ser Cys Phe Gln Lys Ala Gln Leu Lys Ser Ala Asn
305                 310                 315                 320

Thr Gly Asn Asn Glu Arg Ile Ile Asn Val Ser Ile Lys Lys Leu Lys
                325                 330                 335

Arg Lys Pro Pro Ser Thr Asn Ala Gly Arg Arg Gln Lys His Arg Leu
            340                 345                 350

Thr Cys Pro Ser Cys Asp Ser Tyr Glu Lys Lys Pro Pro Lys Glu Phe
            355                 360                 365

Leu Glu Arg Phe Lys Ser Leu Leu Gln Lys Met Ile His Gln His Leu
        370                 375                 380

Ser Ser Arg Thr His Gly Ser Glu Asp Ser
385                 390

<210> SEQ ID NO 167
<211> LENGTH: 397
<212> TYPE: PRT
<213> ORGANISM: Homo sapiens

<400> SEQUENCE: 167

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser Gln Val Gln Leu Val Glu Ser Gly Gly Gly Val
    130                 135                 140
```

-continued

Val Gln Pro Gly Gly Ser Leu Arg Leu Ser Cys Ala Ala Ser Gly Phe
145                 150                 155                 160

Ala Phe Arg Gly Phe Gly Met Ser Trp Val Arg Gln Ala Pro Gly Lys
                165                 170                 175

Gly Leu Glu Trp Val Ser Ser Ile Asn Asn Gly Gly Ser Asp Thr Tyr
            180                 185                 190

Tyr Ala Asp Ser Val Lys Gly Arg Phe Thr Ile Ser Arg Asp Asn Ser
        195                 200                 205

Lys Asn Thr Leu Tyr Leu Gln Met Asn Ser Leu Arg Ala Glu Asp Thr
    210                 215                 220

Ala Val Tyr Tyr Cys Ala Ile Gly Gly Pro Gly Ala Ser Pro Ser Gly
225                 230                 235                 240

Gln Gly Thr Gln Val Thr Val Ser Ser Gly Gly Gly Ser Gly Gly
                245                 250                 255

Gly Gly Ser Gly Gly Gly Ser Ala Pro Thr Ser Ser Ser Thr Lys
            260                 265                 270

Lys Thr Gln Leu Gln Leu Glu His Leu Leu Leu Asp Leu Gln Met Ile
            275                 280                 285

Leu Asn Gly Ile Asn Asn Tyr Lys Asn Pro Lys Leu Thr Arg Met Leu
    290                 295                 300

Thr Phe Lys Phe Tyr Met Pro Lys Lys Ala Thr Glu Leu Lys His Leu
305                 310                 315                 320

Gln Cys Leu Glu Glu Glu Leu Lys Pro Leu Glu Glu Val Leu Asn Leu
                325                 330                 335

Ala Gln Ser Lys Asn Phe His Leu Arg Pro Arg Asp Leu Ile Ser Asn
            340                 345                 350

Ile Asn Val Ile Val Leu Glu Leu Lys Gly Ser Glu Thr Thr Phe Met
        355                 360                 365

Cys Glu Tyr Ala Asp Glu Thr Ala Thr Ile Val Glu Phe Leu Asn Arg
    370                 375                 380

Trp Ile Thr Phe Ser Gln Ser Ile Ile Ser Thr Leu
385                 390                 395

<210> SEQ ID NO 168
<211> LENGTH: 394
<212> TYPE: PRT
<213> ORGANISM: Homo sapiens

<400> SEQUENCE: 168

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asn Met Thr Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Ser Gly Gly Ser Gly Gly Ser
        130                 135                 140

Gly Gln Val Gln Leu Val Glu Ser Gly Gly Val Val Gln Pro Gly
145                 150                 155                 160

Gly Ser Leu Arg Leu Ser Cys Ala Ala Ser Gly Phe Ala Phe Arg Gly
                165                 170                 175

Phe Gly Met Ser Trp Val Arg Gln Ala Pro Gly Lys Gly Leu Glu Trp
            180                 185                 190

Val Ser Ser Ile Asn Asn Gly Gly Ser Asp Thr Tyr Tyr Ala Asp Ser
        195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Ile Gly Gly Pro Gly Ala Ser Pro Ser Gly Gln Gly Thr Gln
                245                 250                 255

Val Thr Val Ser Ser Gln Gly Gln Asp Arg His Met Ile Arg Met Arg
            260                 265                 270

Gln Leu Ile Asp Ile Val Asp Gln Leu Lys Asn Tyr Val Asn Asp Leu
        275                 280                 285

Val Pro Glu Phe Leu Pro Ala Pro Glu Asp Val Glu Thr Asn Cys Glu
290                 295                 300

Trp Ser Ala Phe Ser Cys Phe Gln Lys Ala Gln Leu Lys Ser Ala Asn
305                 310                 315                 320

Thr Gly Asn Asn Glu Arg Ile Ile Asn Val Ser Ile Lys Lys Leu Lys
                325                 330                 335

Arg Lys Pro Pro Ser Thr Asn Ala Gly Arg Arg Gln Lys His Arg Leu
            340                 345                 350

Thr Cys Pro Ser Cys Asp Ser Tyr Glu Lys Lys Pro Pro Lys Glu Phe
        355                 360                 365

Leu Glu Arg Phe Lys Ser Leu Leu Gln Lys Met Ile His Gln His Leu
370                 375                 380

Ser Ser Arg Thr His Gly Ser Glu Asp Ser
385                 390

<210> SEQ ID NO 169
<211> LENGTH: 397
<212> TYPE: PRT
<213> ORGANISM: Homo sapiens

<400> SEQUENCE: 169

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys

```
            100                 105                 110
Ser Leu Leu Gln Lys Met Ile His Gln His Leu Ser Ser Arg Thr His
        115                 120                 125

Gly Ser Glu Asp Ser Gln Val Gln Leu Val Glu Ser Gly Gly Gly Val
    130                 135                 140

Val Gln Pro Gly Gly Ser Leu Arg Leu Ser Cys Ala Ala Ser Gly Phe
145                 150                 155                 160

Ala Phe Arg Gly Phe Gly Met Ser Trp Val Arg Gln Ala Pro Gly Lys
                165                 170                 175

Gly Leu Glu Trp Val Ser Ser Ile Asn Asn Gly Gly Ser Asp Thr Tyr
            180                 185                 190

Tyr Ala Asp Ser Val Lys Gly Arg Phe Thr Ile Ser Arg Asp Asn Ser
        195                 200                 205

Lys Asn Thr Leu Tyr Leu Gln Met Asn Ser Leu Arg Ala Glu Asp Thr
    210                 215                 220

Ala Val Tyr Tyr Cys Ala Ile Gly Gly Pro Gly Ala Ser Pro Ser Gly
225                 230                 235                 240

Gln Gly Thr Gln Val Thr Val Ser Ser Gly Gly Gly Ser Gly Gly
                245                 250                 255

Gly Gly Ser Gly Gly Gly Ser Ala Pro Ala Ser Ser Ser Thr Lys
            260                 265                 270

Lys Thr Gln Leu Gln Leu Glu His Leu Leu Leu Asp Leu Gln Met Ile
    275                 280                 285

Leu Asn Gly Ile Asn Asn Tyr Lys Asn Pro Lys Leu Thr Asn Met Thr
    290                 295                 300

Thr Phe Lys Phe Tyr Met Pro Lys Lys Ala Thr Glu Leu Lys His Leu
305                 310                 315                 320

Gln Cys Leu Glu Glu Glu Leu Lys Pro Leu Glu Val Leu Asn Leu
                325                 330                 335

Ala Gln Ser Lys Asn Phe His Leu Arg Pro Arg Asp Leu Ile Ser Asn
            340                 345                 350

Ile Asn Val Ile Val Leu Glu Leu Lys Gly Ser Glu Thr Thr Phe Met
        355                 360                 365

Cys Glu Tyr Ala Asp Glu Thr Ala Thr Ile Val Glu Phe Leu Asn Arg
    370                 375                 380

Trp Ile Thr Phe Ser Gln Ser Ile Ile Ser Thr Leu Thr
385                 390                 395

<210> SEQ ID NO 170
<211> LENGTH: 394
<212> TYPE: PRT
<213> ORGANISM: Homo sapiens

<400> SEQUENCE: 170

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Asn Met Thr Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80
```

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
        100                 105                 110

Thr Ile Val Glu Phe Leu Asn Arg Trp Ile Thr Phe Ser Gln Ser Ile
    115                 120                 125

Ile Ser Thr Leu Thr Gly Ser Gly Ser Gly Ser Gly Gly Ser
130                 135                 140

Gly Gln Val Gln Leu Val Glu Ser Gly Gly Val Val Gln Pro Gly
145                 150                 155                 160

Gly Ser Leu Arg Leu Ser Cys Ala Ala Ser Gly Phe Ala Phe Arg Gly
                165                 170                 175

Phe Gly Met Ser Trp Val Arg Gln Ala Pro Gly Lys Gly Leu Glu Trp
            180                 185                 190

Val Ser Ser Ile Asn Asn Gly Gly Ser Asp Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Ile Gly Gly Pro Gly Ala Ser Pro Ser Gly Gln Gly Thr Gln
                245                 250                 255

Val Thr Val Ser Ser Gln Gly Gln Asp Glu His Met Ile Arg Met Arg
            260                 265                 270

Gln Leu Ile Asp Ile Val Asp Gln Leu Lys Asn Tyr Val Asn Asp Leu
        275                 280                 285

Val Pro Glu Phe Leu Pro Ala Pro Glu Asp Val Glu Thr Asn Cys Glu
    290                 295                 300

Trp Ser Ala Phe Ser Cys Phe Gln Lys Ala Gln Leu Lys Ser Ala Asn
305                 310                 315                 320

Thr Gly Asn Asn Glu Arg Ile Ile Asn Val Ser Ile Lys Lys Leu Lys
                325                 330                 335

Arg Lys Pro Pro Ser Thr Asn Ala Gly Arg Arg Gln Lys His Arg Leu
            340                 345                 350

Thr Cys Pro Ser Cys Asp Ser Tyr Glu Lys Lys Pro Pro Lys Glu Phe
        355                 360                 365

Leu Glu Arg Phe Lys Ser Leu Leu Gln Lys Met Ile His Gln His Leu
    370                 375                 380

Ser Ser Arg Thr His Gly Ser Glu Asp Ser
385                 390

<210> SEQ ID NO 171
<211> LENGTH: 397
<212> TYPE: PRT
<213> ORGANISM: Homo sapiens

<400> SEQUENCE: 171

Gln Gly Gln Asp Glu His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Gln Lys His Arg Leu Thr Cys Pro Ser Cys
            85                  90                  95

Asp Ser Tyr Glu Lys Lys Pro Pro Lys Glu Phe Leu Glu Arg Phe Lys
                100                 105                 110

Ser Leu Leu Gln Lys Met Ile His Gln His Leu Ser Ser Arg Thr His
            115                 120                 125

Gly Ser Glu Asp Ser Gln Val Gln Leu Val Glu Ser Gly Gly Gly Val
            130                 135                 140

Val Gln Pro Gly Gly Ser Leu Arg Leu Ser Cys Ala Ala Ser Gly Phe
145                 150                 155                 160

Ala Phe Arg Gly Phe Gly Met Ser Trp Val Arg Gln Ala Pro Gly Lys
                165                 170                 175

Gly Leu Glu Trp Val Ser Ser Ile Asn Asn Gly Gly Ser Asp Thr Tyr
            180                 185                 190

Tyr Ala Asp Ser Val Lys Gly Arg Phe Thr Ile Ser Arg Asp Asn Ser
            195                 200                 205

Lys Asn Thr Leu Tyr Leu Gln Met Asn Ser Leu Arg Ala Glu Asp Thr
210                 215                 220

Ala Val Tyr Tyr Cys Ala Ile Gly Gly Pro Gly Ala Ser Pro Ser Gly
225                 230                 235                 240

Gln Gly Thr Gln Val Thr Val Ser Ser Gly Gly Gly Ser Gly Gly
                245                 250                 255

Gly Gly Ser Gly Gly Gly Gly Ser Ala Pro Ala Ser Ser Ser Thr Lys
            260                 265                 270

Lys Thr Gln Leu Gln Leu Glu His Leu Leu Leu Asp Leu Gln Met Ile
            275                 280                 285

Leu Asn Gly Ile Asn Asn Tyr Lys Asn Pro Lys Leu Thr Asn Met Thr
            290                 295                 300

Thr Phe Lys Phe Tyr Met Pro Lys Lys Ala Thr Glu Leu Lys His Leu
305                 310                 315                 320

Gln Cys Leu Glu Glu Glu Leu Lys Pro Leu Glu Val Leu Asn Leu
            325                 330                 335

Ala Gln Ser Lys Asn Phe His Leu Arg Pro Arg Asp Leu Ile Ser Asn
            340                 345                 350

Ile Asn Val Ile Val Leu Glu Leu Lys Gly Ser Glu Thr Thr Phe Met
            355                 360                 365

Cys Glu Tyr Ala Asp Glu Thr Ala Thr Ile Val Glu Phe Leu Asn Arg
370                 375                 380

Trp Ile Thr Phe Ser Gln Ser Ile Ile Ser Thr Leu Thr
385                 390                 395

<210> SEQ ID NO 172
<211> LENGTH: 114
<212> TYPE: PRT
<213> ORGANISM: Homo sapiens

<400> SEQUENCE: 172

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln

```
                35                  40                  45
Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```